United States Patent
Tamai et al.

(10) Patent No.: US 12,421,498 B2
(45) Date of Patent: Sep. 23, 2025

(54) ECTODERMAL MESENCHYMAL STEM CELLS AND METHOD FOR PRODUCING SAME

(71) Applicants: STEMRIM INC., Osaka (JP); OSAKA UNIVERSITY, Osaka (JP)

(72) Inventors: Katsuto Tamai, Suita (JP); Takashi Shimbo, Suita (JP); Eiji Sasaki, Suita (JP); Takehiko Yamazaki, Toyonaka (JP)

(73) Assignees: STEMRIM INC., Osaka (JP); OSAKA UNIVERSITY, Osaka (JP)

( * ) Notice: Subject to any disclaimer, the term of this patent is extended or adjusted under 35 U.S.C. 154(b) by 321 days.

(21) Appl. No.: 16/768,203

(22) PCT Filed: Nov. 30, 2018

(86) PCT No.: PCT/JP2018/044282
§ 371 (c)(1),
(2) Date: May 29, 2020

(87) PCT Pub. No.: WO2019/107566
PCT Pub. Date: Jun. 6, 2019

(65) Prior Publication Data
US 2020/0291359 A1    Sep. 17, 2020

Related U.S. Application Data

(60) Provisional application No. 62/593,310, filed on Dec. 1, 2017.

(51) Int. Cl.
| C12N 5/0775 | (2010.01) |
| A61K 35/28 | (2015.01) |
| C07K 14/47 | (2006.01) |
| G01N 33/50 | (2006.01) |
| A61K 38/00 | (2006.01) |

(52) U.S. Cl.
CPC ............ *C12N 5/0663* (2013.01); *A61K 35/28* (2013.01); *C07K 14/47* (2013.01); *G01N 33/5073* (2013.01); *A61K 38/00* (2013.01)

(58) Field of Classification Search
CPC ... C12N 5/0663; A61K 35/28; G01N 33/5073
See application file for complete search history.

(56) References Cited

U.S. PATENT DOCUMENTS

| | | |
|---|---|---|
| 3,896,810 A | 7/1975 | Akiyama |
| 4,732,155 A | 3/1988 | Zetter et al. |
| 5,133,755 A | 7/1992 | Brekke |
| 5,661,127 A | 8/1997 | Bhatnagar et al. |
| 5,760,261 A | 6/1998 | Guttag |
| 5,851,986 A | 12/1998 | Takada et al. |
| 5,902,799 A | 5/1999 | Herrmann et al. |
| 6,586,185 B2 | 7/2003 | Wolf et al. |
| 6,905,874 B2 | 6/2005 | Berenson et al. |
| 7,160,904 B2 | 1/2007 | Cooke et al. |
| 7,220,723 B2 | 5/2007 | Tracey et al. |
| 7,288,250 B2 | 10/2007 | Newman et al. |
| 7,446,100 B2 | 11/2008 | Pilarski |
| 7,470,538 B2 | 12/2008 | Laughlin et al. |
| 7,632,802 B2 | 12/2009 | Tessier et al. |
| 7,749,959 B2 | 7/2010 | Tracey et al. |
| 7,754,217 B2 | 7/2010 | Bianchi et al. |
| 7,833,975 B2 | 11/2010 | Okazawa |
| 7,939,057 B2 | 5/2011 | Battista et al. |
| 8,119,121 B2 | 2/2012 | Fraser et al. |
| 8,546,547 B2 | 10/2013 | Traversa et al. |
| 8,551,470 B2 | 10/2013 | Son et al. |
| 9,623,078 B2 | 4/2017 | Tamai et al. |
| 9,688,733 B2 | 6/2017 | Tamai et al. |
| 9,707,298 B2 | 7/2017 | Traversa et al. |
| 10,364,276 B2 | 7/2019 | Tamai et al. |
| 10,393,762 B2 | 8/2019 | Fuhrmann et al. |
| 10,550,165 B2 | 2/2020 | Tamai et al. |
| 10,595,530 B2 | 3/2020 | Goodman et al. |
| 10,626,153 B2 | 4/2020 | Bianchi et al. |
| 11,298,403 B2 | 4/2022 | Tamai et al. |
| 2003/0003482 A1 | 1/2003 | Halle et al. |

(Continued)

FOREIGN PATENT DOCUMENTS

| AU | 2003228099 | 1/2004 |
| AU | 2004203732 | 7/2004 |

(Continued)

OTHER PUBLICATIONS

Baer et al. Comprehensive Phenotypic Characterization of Human Adipose-Derived Stromal/Stem Cells and Their Subsets by a High Throughput Technology. Stem Cells and Development vol. 22, No. 2, p. 330-339 (Year: 2013).*
Sidney et al. Concise Review: Evidence for CD34 as a Common Marker for Diverse Progenitors. Stem Cells 2014;32:1380-1389 (Year: 2014).*
Suchacki et al. Bone marrow adipose tissue: formation, function and regulation. Curr Opin Pharmacol. Jun. 2016 ; 28: 50-56 (Year: 2016).*
PROCR gene—Protein C Receptor. downloaded from https://www.genecards.org/cgi-bin/carddisp.pl?gene=PROCR (Year: 2022).*

(Continued)

*Primary Examiner* — Taeyoon Kim
(74) *Attorney, Agent, or Firm* — Wenderoth, Lind & Ponack, L.L.P.

(57) ABSTRACT

The inventors discovered that ectodermal mesenchymal stem cells circulating in peripheral blood that are induced by necrotic tissue damage contribute to the regeneration of damaged tissue. On the basis of this discovery, provided are ectodermal mesenchymal stem cells, a method for producing the same, and a screening method for a substance having pluripotent stem cell inductive activity, the screening method using cells induced by necrotic tissue damage in peripheral blood as an index.

9 Claims, 19 Drawing Sheets
Specification includes a Sequence Listing.

(56) References Cited

U.S. PATENT DOCUMENTS

| | | |
|---|---|---|
| 2003/0060410 A1 | 3/2003 | Tracey et al. |
| 2004/0031072 A1 | 2/2004 | La Rosa et al. |
| 2004/0053841 A1 | 3/2004 | Tracey et al. |
| 2004/0156851 A1 | 8/2004 | Newman |
| 2004/0191246 A1 | 9/2004 | Connelly et al. |
| 2004/0242481 A1 | 12/2004 | Bianchi et al. |
| 2004/0249448 A1 | 12/2004 | Gault |
| 2004/0265971 A1 | 12/2004 | Sato et al. |
| 2005/0014255 A1 | 1/2005 | Tang et al. |
| 2005/0101564 A1 | 5/2005 | Pilarski |
| 2008/0038309 A1 | 2/2008 | Fumero et al. |
| 2009/0028832 A1 | 1/2009 | Chung et al. |
| 2009/0053277 A1 | 2/2009 | Nagaya et al. |
| 2009/0105341 A1 | 4/2009 | Stanton |
| 2009/0324677 A1 | 12/2009 | Traversa et al. |
| 2010/0040608 A1 | 2/2010 | Wahren-Herlenius et al. |
| 2012/0178676 A1 | 7/2012 | Barrack et al. |
| 2012/0237504 A1 | 9/2012 | Brooks et al. |
| 2014/0065094 A1 | 3/2014 | Traversa et al. |
| 2014/0206619 A1 | 7/2014 | Tamai et al. |
| 2015/0273017 A1 | 10/2015 | Tamai et al. |
| 2015/0274792 A1 | 10/2015 | Tamai et al. |
| 2016/0032248 A1 | 2/2016 | Short et al. |
| 2017/0304398 A1 | 10/2017 | Traversa et al. |
| 2018/0055886 A1 | 3/2018 | Tamai et al. |
| 2018/0072785 A1 | 3/2018 | Tamai et al. |
| 2019/0343924 A1 | 11/2019 | Tamai et al. |
| 2020/0038486 A1 | 2/2020 | Tamai et al. |
| 2020/0291359 A1 | 9/2020 | Tamai et al. |
| 2020/0369736 A1 | 11/2020 | Tamai et al. |
| 2021/0024594 A1 | 1/2021 | Tamai et al. |
| 2021/0163552 A1 | 6/2021 | Nihashi et al. |
| 2021/0347839 A1 | 11/2021 | Tamai et al. |
| 2022/0009976 A1 | 1/2022 | Tamai et al. |

FOREIGN PATENT DOCUMENTS

| | | |
|---|---|---|
| CA | 2 325 226 | 5/2001 |
| CA | 2 512 512 | 7/2004 |
| CA | 2 636 788 | 5/2008 |
| CN | 1516739 | 7/2004 |
| CN | 1193092 | 3/2005 |
| CN | 1671742 | 9/2005 |
| CN | 100447154 | 12/2008 |
| CN | 101366728 | 2/2009 |
| CN | 101374538 | 2/2009 |
| CN | 102076350 | 5/2011 |
| CN | 102247392 | 11/2011 |
| CN | 102443064 | 5/2012 |
| CN | 102711777 | 10/2012 |
| CN | 105026553 | 11/2015 |
| EP | 1 114 862 | 7/2001 |
| EP | 1 459 759 | 9/2004 |
| EP | 0 791 601 | 4/2005 |
| EP | 2 039 367 | 3/2009 |
| EP | 2 055 308 | 5/2009 |
| EP | 2 284 255 | 2/2011 |
| EP | 2 301 559 | 3/2011 |
| EP | 2 301 560 | 3/2011 |
| EP | 2 703 487 | 3/2014 |
| EP | 2 913 058 | 9/2015 |
| EP | 3 556 378 | 10/2019 |
| EP | 3 719 117 | 10/2020 |
| EP | 3 750 553 | 12/2020 |
| JP | 3018313 | 3/2000 |
| JP | 2003-505506 | 2/2003 |
| JP | 3421741 | 6/2003 |
| JP | 2005-508913 | 4/2005 |
| JP | 2005-512507 | 5/2005 |
| JP | 2005-537253 | 12/2005 |
| JP | 2006-510619 | 3/2006 |
| JP | 2006-517537 | 7/2006 |
| JP | 2006-523085 | 10/2006 |
| JP | 2007-320919 | 12/2007 |
| JP | 2008-507505 | 3/2008 |
| JP | 2008-511300 | 4/2008 |
| JP | 2010-503630 | 2/2010 |
| JP | 4982739 | 7/2012 |
| JP | 5134772 | 1/2013 |
| JP | 5814549 | 11/2015 |
| KR | 10-2009-0078304 | 7/2009 |
| RU | 2005 102 593 | 10/2005 |
| RU | 2 410 125 | 4/2009 |
| RU | 2010 148 785 | 6/2012 |
| RU | 2 599 448 | 10/2016 |
| WO | 01/08683 | 2/2001 |
| WO | 02/074337 | 9/2002 |
| WO | 02/088181 | 11/2002 |
| WO | 02/092004 | 11/2002 |
| WO | 03/026691 | 4/2003 |
| WO | 03/043651 | 5/2003 |
| WO | 2004/004763 | 1/2004 |
| WO | 2004/004770 | 1/2004 |
| WO | 2004/044001 | 5/2004 |
| WO | 2004/046345 | 6/2004 |
| WO | 2004/061456 | 7/2004 |
| WO | 2005/025604 | 3/2005 |
| WO | 2005/074984 | 8/2005 |
| WO | 2005/087797 | 9/2005 |
| WO | 2006/008779 | 1/2006 |
| WO | 2006/010628 | 2/2006 |
| WO | 2006/024547 | 3/2006 |
| WO | 2006/080434 | 3/2006 |
| WO | 2006/047820 | 5/2006 |
| WO | 2006/077614 | 7/2006 |
| WO | 2006/100651 | 9/2006 |
| WO | 2006/114805 | 11/2006 |
| WO | 2007/015546 | 2/2007 |
| WO | 2007/031100 | 3/2007 |
| WO | 2007/061762 | 5/2007 |
| WO | 2007/076200 | 7/2007 |
| WO | 2007/130725 | 11/2007 |
| WO | 2008/018641 | 2/2008 |
| WO | 2008/031612 | 3/2008 |
| WO | 2008/053892 | 5/2008 |
| WO | 2008/155659 | 12/2008 |
| WO | 2009/133939 | 11/2009 |
| WO | 2009/133940 | 11/2009 |
| WO | 2009/133943 | 11/2009 |
| WO | 2011/046570 | 4/2011 |
| WO | 2011/052668 | 5/2011 |
| WO | 2012/147470 | 11/2012 |
| WO | 2014/065347 | 5/2014 |
| WO | 2014/065348 | 5/2014 |
| WO | 2014/191364 | 12/2014 |
| WO | 2016/184795 | 11/2016 |
| WO | 2018/139562 | 8/2018 |
| WO | 2018/186480 | 10/2018 |
| WO | 2018/199107 | 11/2018 |
| WO | 2019/107530 | 6/2019 |
| WO | 2019/107566 | 6/2019 |
| WO | 2019/156137 | 8/2019 |
| WO | 2020/071519 | 4/2020 |
| WO | 2020/071520 | 4/2020 |

OTHER PUBLICATIONS

Morikawa et al. Prospective identification, isolation, and systemic transplantation of multipotent mesenchymal stem cells in murine bone marrow. J. Exp. Med. vol. 206 No. 11 2483-2496. (Year: 2009).*

Ahrens et al. Mesenchymal Stem Cell Content of Human Vertebral Bone Marrow. Transplantation • vol. 78, No. 6, p. 925-929 (Year: 2004).*

Akashi et al. A clonogenic common myeloid progenitor that gives rise to all myeloid lineages. Nature. vol. 404, p. 193-197 (Year: 2000).*

Pimanda. Mesoderm-Derived PDGFRA+ Cells Regulate Emergence of Hematopoietic Stem Cells in the Dorsal Aorta. Experimental Hematology 64 (2018) S41-S51 (Year: 2018).*

Betsholtz et al. Developmental roles of platelet-derived growth factors. BioEssays 23:494-507, 2001. (Year: 2001).*

(56) References Cited

OTHER PUBLICATIONS

Dominici et al. Minimal criteria for defining multipotent mesenchymal stromal cells. The International Society for Cellular Therapy position statement. Cytotherapy (2006) vol. 8, No. 4, 315-317 (Year: 2006).*
Extended European Search Report issued Sep. 30, 2021 in corresponding European Patent Application No. 18883298.4, 8 pages.
Alden et al., "In Vivo Endochondral Bone Formation Using a Bone Morphogenetic Protein 2 Adenoviral Vector", Human Gene Therapy, 1999, vol. 10, pp. 2245-2253, 9 pages.
Andersson et al., "HMGB1 as a DNA-binding cytokine", Journal of Leukocyte Biology, 2002, vol. 72, pp. 1084-1091, 8 pages.
Armiñán, et al., "Mesenchymal Stem Cells Provide Better Results Than Hematopoietic Precursors for the Treatment of Myocardial Infarction", Journal of American College of Cardiology, 2010, vol. 55, No. 20, pp. 2244-2253, 10 pages.
Arnau et al., "Current strategies for the use of affinity tags and tag removal for the purification of recombinant proteins", Protein Expression and Purification, 2006, vol. 48, pp. 1-13, 13 pages.
Asch et al., "Lack of sensitivity of the electrocardiogram for detection of old myocardial infarction: A cardiac magnetic resonance imaging study", American Heart Journal, 2006, vol. 152, No. 4, pp. 742-748, 7 pages.
Ball et al., "Mesenchymal stem cells and neovascularization: role of platelet-derived growth factor receptors", J. Cell. Mol. Med., vol. 11, No. 5, 2007, pp. 1012-1030, 19 pages.
Basso et al., "Basso Mouse Scale for Locomotion Detects Differences in Recovery after Spinal Cord Injury in Five Common Mouse Strains", Journal of Neurotrauma, 2006, vol. 23, No. 5, pp. 635-659, 19 pages.
Berry et al., "Mesenchymal stem cell injection after myocardial infarction improves myocardial compliance", Am J. Physiol Heart Circ Physiol, 2006, vol. 290, pp. H2196-H2203, 8 pages.
M. E. Bianchi, "High mobility group 1 protein (HMGB1) N-terminal peptide", ADO80180 standard; peptide; 62 AA, 2004, 1 page.
Bittira et al., "Mobilization and homing of bone marrow stromal cells in myocardial infarction", European Journal of Cardio-thoracic Surgery, 2003, vol. 24, pp. 393-398, 6 pages.
Blain et al., "δ-Sarcoglycan-deficient muscular dystrophy: from discovery to therapeutic approaches", Blain and Straub Skeletal Muscle, 2011, vol. 1, pp. 1-12, 12 pages.
Brunner et al., "Erythropoietin administration after myocardial infarction in mice attenuates ischemic cardiomyopathy associated with enhanced homing of bone marrow-derived progenitor cells via the CXCR-4/SDF-1 axis", The FASEB Journal, 2009, vol. 23, pp. 351-361, 11 pages.
Zheng et al., BTF3 Nucleotide Sequence from "Sequencing and expression of complementary DNA for the general transcription factor BTF3", Nature, 1990, vol. 344, pp. 556-559, 6 pages.
Cairo et al., "Results of a Phase I/II Trial of Recombinant Human Granulocyte-Macrophage Colony-Stimulating Factor in Very Low Birthweight Neonates: Significant Induction of Circulatory Neutrophils, Monocytes, Platelets, and Bone Marrow Neutrophils", Blood, 1995, vol. 86, No. 7, pp. 2509-2515, 8 pages.
"Cardiomegaly", Medical Definition and More from Merriam-Webster, https://www.merriam-webster.com/medical/cardiomegaly, 2020, 2 pages.
"Cardiomyopathy: Symptoms, diagnosis and treatment", Harvard Health Publishing, Harvard Medical School, 2014, 3 pages.
Castro et al., "Failure of Bone Marrow Cells to Transdifferentiate into Neural Cells in Vivo", Science, 2002, vol. 297, p. 1299, 1 page.
Chen et al., "Human Bone Marrow Stromal Cell Cultures Conditioned by Traumatic Brain Tissue Extracts: Growth Factor Production", Journal of Neuroscience Research, 2002, vol. 69, pp. 687-691, 5 pages.
Chen et al., "Coaxing bone marrow stromal mesenchymal stem cells towards neuronal differentiation: progress and uncertainties", Cellular and Molecular Life Sciences, 2006, vol. 63, pp. 1649-1657, 9 pages.
J. Cole, III, "Pharmacologic Mobilization of Mesenchymal Stem Cells for Enhanced Bone Formation", Master of Sciences Thesis submitted to Rush University, 2009, pp. 1-68, 82 pages.
DelaRosa et al., "Modulation of Adult Mesenchymal Stem Cells Activity by Toll-Like Receptors: Implications on Therapeutic Potential", Mediators of Inflammation, 2010, vol. 2010, Article ID 865601, pp. 1-9, 9 pages.
Desai et al., "Tissue response to intraperitoneal implants of polyethylene oxide-modified polyethylene terephthalate", Biomaterials, 1992, vol. 13, No. 8, pp. 505-510, Abstract, 1 page.
De Santis et al., "TNFα deficiency results in increased IL-1β in an early onset of spontaneous murine colitis", Cell Death and Disease, 2017, vol. 8, e2993, pp. 1-7, 7 pages.
Eckert et al., "S100 Proteins in the Epidermis", The Journal of Investigative Dermatology, 2004, vol. 123, pp. 23-33, 11 pages.
Erlandsson et al., "The nuclear protein HMGB 1 as a proinflammatory mediator", Eur. J. Immunol., 2004, vol. 34, pp. 1503-1512, 10 pages.
Frankel et al., "Characterization of diphtheria fusion proteins targeted to the human interleukin-3 receptor", Protein Engineering, 2000, vol. 13, No. 8, pp. 575-581, 7 pages.
Fritsch et al., "A hypomorphic mouse model of dystrophic epidermolysis bullosa reveals mechanisms of disease and response to fibroblast therapy", The Journal of Clinical Investigation, 2008, vol. 118, No. 5, pp. 1669-1679, 11 pages.
Fukushima et al., "Registry Report on Heart Transplantation in Japan", Circulation Journal, 2017, vol. 81, pp. 298-303, 6 pages.
Gallina et al., "A New Paradigm in Cardiac Regeneration: The Mesenchymal Stem Cell Secretome", Stem Cells International, 2015, vol. 2015, Article ID 765846, pp. 1-10, 10 pages.
Goto et al., "Investigation of the application of myocardial regeneration inducing therapy using HMGB1 to cardiac infarction", ISSN 1347-7919, 2017, vol. 16, p. 289, with English translation, 4 pages.
Gudjonsson et al., "Chapter 18 Psoriasis", pp. 197-217, 21 pages.
S.A. Gueukdjian, "Intra-Arterial Injections in the Treatment of Peripheral Vascular Disease", Postgrad Med J, 1955, vol. 31, pp. 30-31, 3 pages.
Guillot et al., "Response of Human Pulmonary Epithelial Cells to Lipopolysaccharide Involves Toll-like Receptor 4 (TLR4)-dependent Signaling Pathways", The Journal of Biological Chemistry, 2004, vol. 279, No. 4, pp. 2712-2718, 8 pages.
Guo et al., "Monocyte Chemotactic Protein-1 Promotes the Myocardial Homing of Mesenchymal Stem Cells in Dilated Cardiomyopathy", International Journal of Molecular Sciences, 2013, vol. 14, pp. 8164-8178, 15 pages.
Harrison et al., "Oxidation Regulates the Inflammatory Properties of the Murine S100 Protein S100A8", J. Biol. Chem., 1998, vol. 274, No. 13, pp. 8561-8569, 10 pages.
Healthwise Staff, "Age-related Macular Degeneration", University of Michigan Health System, 2015, http://www.uofmhealth.org/health-library/hw176039, 3 pages.
He et al., "HMGB1 Ameliorates Inflammatory Bowel Disease by Inducing Circulating Mesenchymal Stem Cells", The 17th Congress of the Japanese Society for Regenerative Medicine, 2018, vol. 34, Abstract, 1 page.
Heil et al., "An engineered heparin-binding form of VEGF-E (hbVEGF-E)", Angiogenesis, 2003, vol. 6, No. 3, pp. 201-211, 11 pages.
Herrera et al., "Exogenous mesenchymal stem cells localize to the kidney by means of CD44 following acute tubular injury", Kidney International, 2007, vol. 72, pp. 430-441, 12 pages.
Hiratsuka et al., "Tumour-mediated upregulation of chemoattractants and recruitment of myeloid cells predetermines lung metastasis", Nature Cell Biology, 2006, vol. 8, No. 12, pp. 1369-1375, 15 pages.
HMGBiotech, "BoxA from HMGB1, human & mouse, LPS-free", Product Nos. HM-012, HM-013, HM-014, HMGBiotech Srl, 2008, http://www.hmgbiotech.com/products.php?ID=91, accessed 2017 from internet, 2 pages.
HMGBiotech, "BoxA from HMGB1, human & mouse, LPS-free-Datasheet", Product Nos. HM-012, HM-013, HM-014, HMGBiotech Srl, 2008, http://www.hmgbiotech.com/upload/documenti/0515122144_boxa, 1 page.

(56) References Cited

OTHER PUBLICATIONS

Matunis et al., HNRPK_HUMAN Seqeunce from "Cahracterization and primary structure of the poly©-binding heterogeneous nuclear ribonucleoprotein complex K protein", Mol. Cell. Biol., 1992, vol. 12, pp. 164-171; UNiProt, NCBI_TaxID=9606, Accession No. P61978, 2004, 15 pages.

Hori et al., "The Receptor for Advanced Glycation End Products (RAGE) Is a Cellular Binding Site for Amphoterin", Journal of Biological Chemistry, 1995, vol. 270, No. 43, pp. 25752-25761, 10 pages.

Hornef et al., "Toll-like Receptor 4 Resides in the Golgi Apparatus and Colocalizes with Internalized Lipopolysaccharide in Intestinal Epithelial Cells", J. Exp. Med., 2002, vol. 195, No. 5, pp. 559-570, 12 pages.

V.J. Hruby, "Designing Peptide Receptor Agonists and Antagonists", Nature Reviews Drug Discovery, 2002, vol. 1, pp. 847-858, 15 pages.

Hu et al., "Role of high-mobility group box 1 protein in inflammatory bowel disease", Inflamm. Res., 2015, vol. 64, pp. 557-563, 7 pages.

Ichinose et al., "Antiangiogenic Endostatin Peptide Ameliorates Renal Alternations in the Early Stage of a Type 1 Diabetic Nephropathy Model", Diabetes, 2005, vol. 54, No. 10, pp. 2891-2903, 13 pages.

Instruction Manual of HiTrap Chelating HP, Amersham Biosciences, 2003, pp. 1-6, 6 pages.

Ishikane et al., "Therapeutic application of allogenic fetal membrane-derived mesenchymal stem cells transplantation in regenerative medicine", Pharmaceutical Bulletin of Fukuoka University, 2011, vol. 11, with English Translation, pp. 17-25, 22 pages.

Ishikane et al., Development of multi-growth factor secreted fetal membrane-derived mesenchymal stem cell sheets, Grants-in-Aid for Scientific Research, 2014, with English Translation, pp. 1-6, 14 pages.

Jansen et al., "Transplantation of hematopoietic stem cells from the peripheral blood", Journal of Cellular and Molecular Medicine, 2005, vol. 9, No. 1, pp. 37-50, 14 pages.

Jiang et al., "Pluripotency of mesenchymal stem cells derived from adult marrow", Nature, 2002, vol. 418, pp. 41-49, 9 pages.

Jiao et al., "Researchers find nerve damage may precede diabetic retinopathy", EurekAlert! Science News, 2016, https://www.eurekalert.org/pub-releases/2016-04/uoih-rfv042616.php, 2 pages.

Jin et al., "Isolating culture and induced differentiation of marrow mesenchyma stem cells", Principles and Protocols of Tissue Engineering, 2004, pp. 277-278, with English Translation, 6 pages.

Kaneda et al., "Tissue repair mechanism by bone-marrow-derived stem cells", Experimental Mediciner, 2013, vol. 31, No. 5, pp. 655-661, with English Translation, 17 pages.

Kassis et al., "Isolation of mesenchymal stem cells from G-CSF mobilized human peripheral blood using fibrin microbeads", Bone Marrow Transplantation, 2006, vol. 37, No. 10, pp. 967-976, 10 pages.

Kido et al., "Abstract 15756: The Administration of High-morbidity Group Box 1 Fragment Prevents Deterioration of Cardiac Performance by Enhancement of Bone-marrow Mesenchymal Stem Cells Homing in the Delta-sarcoglycan-deficient Hamster", Circulation, 2017, vol. 136, Suppl. 1, Abstract, 1 page.

Kikuchi et al., "Systemic administration of HMGB1 improves bleomycin-induced skin fibrosis by locally accumulating bone marrow mesenchymal stem cells", Regenerative Medicine, 2017, vol. 16, p. 422, with English Translation, 4 pages.

Kim et al., "Skin Regeneration Using Keratinocytes and Dermal Fibroblasts Cultured on Biodegradable Microspherical Polymer Scaffolds", Journal of Biomedical Materials Research Part B: Applied Biomaterials, 2005, vol. 75, No. 2, pp. 369-377, 9 pages.

Kirov, et al., "In Vivo 2-Photon Microscopy Reveals G-CSF Enhanced Mobilization and Targeting of Neo-Endogenous Bone Marrow Stromal Cells to Stroke Injury Sites", Stroke, 2009, vol. 40, No. 4, pp. 1-2, e133, Abstract No. 107, 2 pages.

Kohno et al., "High Mobility Group Box 1 Protein is Associated with Post-Infarction Healing Process and Left Ventricular Remodeling", Circulation Journal., 2008, vol. 72, Suppl. 1, P J-004, pp. 510-511, 2 pages.

Komurasaki, et al., "555 Systemic HMGB1 Administration Ameliorated Bleomycin-Induced Skin Fibrosis by Promoting Accumulation of Bone Marrow-Derived Mesenchymal Stem Cells to the Lesion", Journal of Investigative Dermatology, 2016, vol. 136, No. 9, S255, 1 page.

Komurasaki, et al., "HMGB1 Ameliorates Bleomycin-Induced Skin Fibrosis by Promoting Accumulation of Mesenchymal Stem Cells to the Lesion", The 48$^{th}$ Annual Meetings of the Japanese Society of Matrix Biology and Medicine, 2016, p. 78, with English Translation, 3 pages.

Koren-Morag et al., "White Blood Cell Count and the Incidence of Ischemic Stroke in Coronary Heart Disease Patients", The American Journal of Medicine, 2005, vol. 118, pp. 1004-1009, 6 pages.

Lanza et al., "Essentials of Stem Cell Biology—Chapter 27, Mesenchymal Stem Cells", Elsevier Academic Press, 2006, pp. 205-210, 8 pages.

LaRosa et al., "Glycine max protein SEQ ID No. 211221", Geneseq Accession No. AFQ20044, 2007, 1 page.

Lemp et al., "The Definition and Classification of Dry Eye Disease: Report of the Definition and Classification Subcommittee of the International Dry Eye Workshop (2007)", The Ocular Surface, 2007, vol. 5, No. 2, pp. 75-92, 3 pages.

Li, et al., "Nonviral gene therapy: promises and challenges", Gene Therapy, 2000, vol. 7, pp. 31-34, 4 pages.

Li et al., "Heat-Shock Proteins", Current Protocols in Immunology, 2003, Supplement 58, A.IT.1-A.IT.6, 6 pages.

Li et al., "Advancement of Human Multiply, Sex health and Reproductive Medical Science", Peking University Medical Press, 2007, 1$^{st}$ Edition, pp. 270-271, with English Translation, 9 pages.

Limana et al., "HMGB1 Attenuates Cardiac Remodelling in the Failing Heart via Enhanced Cardiac Regeneration and miR-206-Mediated Inhibition of TIMP-3", PLoS ONE, 2011, vol. 6, No. 6, e19845, pp. 1-11, 11 pages.

Liotta et al., "Toll-Like Receptors 3 ad 4 are Expressed by Human Bone Marrow-Derived Mesenchymal Stem Cells and Can Inhibit Their T-Cell Modulatory Activity by Impairing Notch Signaling", Stem Cells, 2008, vol. 26, pp. 279-289, 11 pages.

Liu et al., "Human Placental Extract Stimulates Liver Regeneration in Rats", Biol. Pharm. Bull., 1998, vol. 21, No. 1, pp. 44-49, 6 pages.

Lonza BenchGuides, "Poietics hMSC Human Mesenchymal Stem Cells and Media", Document #TS-PT-212-7, 2008, 2 pages.

Lund et al., "The Registry of the International Society for Heart and Lung Transplantation: Thirty-Third Adult Heart Transplantation Report—2016; Focus Theme: Primary Diagnostic Indications for Transplant", The Journal of Heart and Lung Transplantation, 2016, vol. 35, No. 10, pp. 1158-1169, 7 pages.

Mansbridge et al., "Skin Tissue Engineering", J. Biomater, Sci. Polymer, Edn, 2008, vol. 19, No. 8, pp. 955-968, 15 pages.

Maron et al., "Contemporary Definitions and Classification of the Cardiomyopathies", Circulation, 2006, vol. 113, pp. 1807-1816, 10 pages.

Maruyama et al., "Inflammation and HMGB1/RAGE system", Kekkan Igaku, 2005, vol. 6, No. 5, pp. 519-525, with English Translation, 15 pages.

Matsumoto et al., "Up-Regulation of Hepatocyte Growth Factor Gene Expression by Inerleukin-1 in Human Skin Fibrosis", Biochemical and Biophysical Research Communications, 1992, vol. 188, No. 1, pp. 235-243, 9 pages.

Meng et al., "HMGB1 induces migration of human bone marrow-derived mesenchymal stem cells", Bulletin of the Academy of Military Medical Sciences, 2006, vol. 30, No. 3, pp. 213-216, with English Translation, 11 pages.

Meng et al., "High Mobility Group Box 1 Protein Inhibits the Proliferation of Human Mesenchymal Stem Cells and Promotes Their Migration and Differentiation along Osteoblastic Pathway", Stem Cells and Development, 2008, vol. 17, No. 4, pp. 805-814, 9 pages.

(56) References Cited

OTHER PUBLICATIONS

Mori et al., "Stem Cells/ES Cells—Mesenchymal Stem Cells—Human Bone Marrow Derived Mesenchymal Stem Cells", Saisei Iryou—Regenerative Medicine, 2005, vol. 4, No. 3, pp. 421-429, 24 pages.
Morosetti et al., "MyoD expression restores defective myogenic differentiation of human mesoangioblasts from inclusion-body myositis muscle", PNAS, 2006, vol. 103, No. 45, pp. 16995-17000, 6 pages.
"Blood Collection: The Mouse", Mouse care guidance from the Institutional Animal Care and Use Committee (IACUC) at University of California, San Francisco; iacuc.ucsf.edu/Policies/BloodCollectionMice.doc; accessed 2014, 2 pages.
Muhamed et al., "Phenotypic Modulation of Cell Types around Implanted Polyethylene Terephthalate Fabric in Rabbit Muscle", Toxicologic Pathology, 2013, vol. 41, pp. 497-507, 11 pages.
Musumeci et al., "An overview of HMGB 1 inhibitors as potential therapeutic agents in HMGB1-related pathologies", Pharmacology & Therapeutics, 2014, vol. 141, pp. 347-357, 11 pages.
Nakajima et al., "Dynamics and Role of High Mobility Group Box-1 (HMGB-1) in Injured Spinal Cord", Nihon Seikei Geka Gakkai Zasshi, J. Jpn. Orthop. Assoc., 2010, vol. 84, No. 8, p. S0150, with English Translation, 2 pages.
Nakanishi et al., "Membrane Potential-Regulated $Ca^{2+}$Signalling in Development and Maturation of Mammalian Cerebellar Granule Cells", J. Physiol., 2006, vol. 575, No. 2, pp. 389-395, 7 pages.
Narumi et al., "High-mobility Group Box 1 Attenuates Mitochondrial Dysfunction and Apoptosis via Heat Shock Protein Beta 1 Induction in Doxorubicin-induced Cardiomyopathy", Bulletin of Yamagata University (Medical Science), 2015, vol. 33, No. 2, pp. 126-127, 2 pages, http:/www.lib.yamagata-u.ac.jp/alllib/elib/kiyon/kiyoum/kiyoum-33-2/image/kiyoum-33-2-125to131.pdf.
NCBI, "Old myocardial infarction", MedGen UID: 57612, retrieved from internet Jan. 19, 2022, 4 pages, https://www.ncbi.nlm.nih.gov/medgen/57612.
Nickoloff et al., "Recent insights into the immunopathogenesis of psoriasis provide new therapeutic opportunities", Journal of Clinical Investigation, 2004, vol. 113, No. 12, pp. 1664-1675, 12 pages.
O'Callaghan et al., "HMGB1 as a key mediator of tissue response to injury: roles in inflammation and tissue repair", European Surgery, 2006, vol. 38, pp. 283-292, 18 pages.
Opitz et al., "Toll-Like Receptor Engagement Enhances the Immunosuppressive Properties of Human Bone Marrow-Derived Mesenchymal Stem Cells by Inducing Indoleamine-2,3-dioxygenase-1 via Interferon-β and Protein Kinase R" Stem Cells, 2009, vol. 27, pp. 909-919, 11 pages.
Otsuru et al., BMP-2 mobilizes robust bone marrow mesenchymal progenitor cells to the circulating blood in bone regeneration, The $28^{th}$ Meeting of the Molecular Biology Society of Japan, 2005, p. 773 (3P-1012), with English Translations, 3 pages.
Ozaki et al. "Comprehensive Analysis of Chemotactic Factors for Bone Marrow Mesenchymal Stem Cells", Stem Cells and Development, 2007, vol. 16, pp. 119-129, 11 pages.
PA2G4_HUMAN Sequence, Accession No. Q9UQ80, Apr. 2001, 9 pages.
Panepucci et al., "Abstract #4427: Comparison of Gene Expression of Mesenchymal Stem Cells from the Umbilical Cord and from the Bone Marrow", Blood, 2003, vol. 16, No. 102, Abstract, 1 page.
Panepucci et al., "Comparison of Gene Expression of Umbilical Cord Vein and Bone Marrow-Derived Mesenchymal Stem Cells", Stem Cells, 2004, vol. 22 No. 7, pp. 1263-1278, 16 pages.
Paul et al., "Stromal Cell-Associated Hematopoiesis: Immortalization and Characterization of a Primate Bone Marrow-Derived Stromal Cell Line", Blood, 1991, vol. 77, No. 8, pp. 1723-1733, 11 pages.
Pevsner-Fischer et al., "Toll-like receptors and their ligands control mesenchymal stem cell functions", Blood, 2007, vol. 109, No. 4, pp. 1422-1432, 11 pages.
PFD5_HUMAN Sequence, Accession No. Q99471, Nov. 1997, 6 pages.
NPM_HUMAN Sequence, Accession No. P06748, Jan. 1988, 15 pages.
PRS6A_HUMAN Sequence, Accession No. P17980, Nov. 1990, 9 pages.
Pusterla et al., "High mobility group B2 is secreted by myeloid cells and has mitogenic and chemoattractant activities similar to high mobility group B1", Autoimmunity, 2009, vol. 42, No. 4, pp. 308-310, 27 pages.
Quertainmont et al., "Mesenchymal Stem Cell Graft Improves Recovery after Spinal Cord Injury in Adult Rats through Neurotrophic and Pro-Angiogenic Actions", PLoS ONE, 2012, vol. 7, No. 6, pp. 1-15, 15 pages.
Racanelli et al., "The Liver as an Immunological Organ", Hepatology, 2006, vol. 43, No. 2, pp. S54-S62, 9 pages.
Rahimi-Movaghar et al., "Effect of Decompression on Complete Spinal Cord Injury in Rats", International Journal of Neuroscience, 2008, vol. 118, pp. 1359-1373, 15 pages.
Raicevic et al., "Inflammation modified the pattern and the function of Toll-like receptors expressed by human mesenchymal stromal cells", Human Immunology, 2010, vol. 71, pp. 235-244, 10 pages.
Robinson et al., "The S100 Family Heterodimer, MRP-8/14, Binds with High Affinity to Heparin and Heparan Sulfate Glycosaminoglycans on Endothelial Cells", The Journal of Biological Chemistry, 2002, vol. 277, No. 5, pp. 3658-3665, 8 pages.
Ross et al., "Histology: A Text and Atlas: With Correlated Cell and Molecular Biology", https://books.google.com/books?id=5vx9DwAAQBAJ&lr=source=gbs_navlinks_s[Jan. 19, 2022], 2 pages.
Ryckman et al., "Proinflammatory Activities of S100: Proteins S100A8, S100A9, and S100A8/A9 Induced Neutrophil Chemotaxis and Adhesion", The Journal of Immunology, 2003, vol. 170, pp. 3233-3242, 10 pages.
Santamaria-Kisiel et al., "Calcium-dependent and -independent interactions of the S100 protein family", Biochem. J., 2006, vol. 396, pp. 201-214, 14 pages.
J. Saver, "Time is Brain—Quantified", Stroke, 2006, vol. 37, pp. 263-266, 4 pages.
Schäffer et al., "Wound Fluid Inhibits Wound Fibroblast Nitric Oxide Synthesis", Journal of Surgical Research, 2004, vol. 122, pp. 43-48, 6 pages.
Schön et al., "Psoriasis", New England Journal of Medicine, 2005, vol. 352, No. 18, pp. 1899-1912, 14 pages.
Scoote et al., "Pathophysiology of Heart Failure", Chapter 19, Essential Cardiology: Principles and Practice, $2^{nd}$ Ed., pp. 347-369, 23 pages.
Seffernick et al., "Melamine Deaminase and Atrazine Chlorohydrolase: 98 Percent Identical but Functionally Different", Journal of Bacteriology, 2001, vol. 183, No. 8, pp. 2405-2410, 6 pages.
Selected cardiac diagnoses and ICD-10 codes, 1 page.
Seong et al., "Hydrophobicity: an ancient damage-associated molecular pattern that initiates innate immune responses", Nature Reviews, Immunology, 2004, vol. 4, pp. 469-478, 10 pages.
Shibata et al., Fibroblast growth-stimulating activity of S100A9 (MRP-14), Eur. J. Biochem., 2004, vol. 271, pp. 2137-2143, 7 pages.
Shing et al., "Heparin Affinity: Purification of a Tumor-Derived Capillary Endothelial Cell Growth Factor", Science, 1984, vol. 223, pp. 1296-1299, 4 pages.
Simard et al., "Bone Marrow-Derived Microglia Play a Critical Role in Restricting Senile Plaque Formation in Alzheimer's Disease", Neuron, 2006, vol. 49, pp. 489-502, 14 pages.
Slater et al., "Endometriotic cells exhibit metaplastic change and oxidative DNA damage as well as decreased function, compared to normal endometrium", Journal of Molecular Histology, 2005, vol. 36, pp. 257-263, 7 pages.
Somia et al., "Gene Therapy: Trials and Tribulations", Nature Reviews, Genetics, 2000, vol. 1, pp. 91-99, 9 pages.
Soo et al., "Heat Shock Proteins as Novel Therapeutic Targets in Cancer", in vivo, 2008, vol. 22, pp. 311-316, 5 pages.
SP16H_HUMAN Sequence, Accession No. Q9Y5B9, Jul. 2006, 10 pages.
Takahashi et al., "Effects of HMGB1 on Postinfarction Chronic Heart-Failure—Novel Mechanism Regarding Therapeutic Effects

(56) References Cited

OTHER PUBLICATIONS of Cell Therapy", 2001, William Harvey Research Institute, with English Translation, I-E-19, 3 pages.

Takami et al., "Synergistic induction of hepatocyte growth factor in human skin fibroblasts by the inflammatory cytokines interleukin-1 and interferon-γ" Biochemical and Biophysical Research Communications, 2005, vol. 327, pp. 212-217, 6 pages.

Takeishi et al., "Importance of inflammation and immune response in heart failure—Toll-like receptor-mediated signaling pathway and ventricular remodeling after myocardial infarction", Journal of Clinical and Experimental Medicine, 2010, vol. 232, No. 5, with English Translation, 19 pages.

Tamai et al., "New Wave of Wound Healing", Japanese Journal of Dermatology, 2008, vol. 118, No. 4, EL28-3-4, with English Translation, 2 pages.

Tamai et al., "Supporting Information", www.pnas.org/egi/content/short/1016753108, pp. 1-12, 12 pages.

U.S. Appl. No. 11/997,475, "Mesenchymal Stem Cell Inducer, Tissue Regeneration Promotor and Method of Preparing Mesenchymal Stem Cell", Abandoned—Incomplete Application (Pre-examination), 37 pages.

U.S. Appl. No. 17/517,967, filed Nov. 3, 2021, "Agents for Promoting Tissue Regeneration by Recruiting Bone Marrow Mesenchymal Stem Cells and/or Pluripotent Stem Cells into Blood", 113 pages.

Tamilselvi et al., "Association of Disease Severity with IL-1 levels in Methotrexate-treated Psoriasis Patients", Scandinavian Journal of Immunology, 2013, vol. 78, pp. 545-553, 9 pages.

Tang et al., "Fibrin(ogen) Mediates Acute Inflammatory Responses to Biomaterials", J. Exp. Med, 1993, vol. 178, pp. 2147-2156, 10 pages.

Tatsumi et al., "HGF/SF Is Present in Normal Adult Skeletal Muscle and Is Capable of Activating Satellite Cells", Developmental Biology, 1998, vol. 194, pp. 114-128, 15 pages.

Teoh et al., "Low-Dose TNF-α Protects Against Hepatic Ischemia-Reperfusion Injury in Mice: Implications for Preconditioning", Hepatology, 2003, vol. 37, No. 1, pp. 118-128, 11 pages.

Thorey et al., "The $Ca^{2+}$-binding Proteins S100A8 and S100A9 are Encoded by Novel Injury-regulated Genes", The Journal of Biological Chemistry, 2001, vol. 276, No. 38, pp. 35818-35825, 8 pages.

Tokuriki et al., "Stability effects of mutations and protein evolvability", Current Opinion in Structural Biology, 2009, vol. 19, pp. 596-604, 9 pages.

Türker et al., "Nasal route and drug delivery systems", Pharmacy World and Science, 2004, vol. 26, pp. 137-142, 6 pages.

Uchida et al., "The chemotactic activity of PDGF-bb BMP-2, and FGF-2 towards committed and uncommitted mesenchymal stem cells", The Journal of Japanese Orthopedic Surgical Society, 2005, vol. 79, No. 8, S832, 1-P6-6., with English translation, 3 pages.

Ueta et al., "Intracellularly Expressed TLR2s and TLR4s Contribution to an Immunosilent Environment at the Ocular Mucosal Epithelium", The Journal of Immunology, 2004, vol. 173, No. 5, pp. 3337-3347, 12 pages.

Uronen-Hansson et al., "Toll-like Receptor 2 (TLR2) and TLR4 are Present Inside Human Dendritic Cells, Associates with Microtubules and the Golgi Apparatus but are not Detectable on the Cell Surface: Integrity of Microtubules is Required for Interleukin-12 Production in Response in Internalized Bacteria", Immunology, 2004, vol. 11, pp. 173-178, 6 pages.

User Manual for StemCell Technologies, "Enumeration, Expansion, and Differentiation of Human Mesenchymal Progenitor Cells Using MesenCult", StemCell Technologies, 2007, Version 2.2.0., 24 pages.

Vandal et al., "Blockade of S100A8 and S100A9 Suppresses Neutrophil Migration in Response to Lipopolysaccharide", The Journal of Immunology, 2003, vol. 171, No. 5, pp. 2602-2609, 8 pages.

Walfish et al., "Pathophysiology of Crohn Disease", Merck Manual Professional Version, Merck Sharp & Dohme Corp., 2020, 7 pages.

Walfish et al., "Overview of Inflammatory Bowel Disease", Merck Manual Professional Version, Merck Sharp & Dohme Corp., 2020, 3 pages.

Walfish et al., "Ulcerative Colitis", Merck Manual Professional Version, Merck Sharp & Dohme Corp., 2020, 8 pages.

Wang et al., "High mobility group protein B1 and research progress of its biological effect", Journal of Chinese Modern Surgery, 2006, vol. 3, No. 22, pp. 1806-1809, with English translation, 15 pages.

Wang et al., "Ischemic cerebral tissue and MCP-1 enhance rat bone marrow stromal cell migration in interface culture", Experimental Hematology, 2002, vol. 30, pp. 831-836, 6 pages.

Wang et al., "Theories and Technologies for Stem Cells", Series of the 21st Century Biotechnologies, Science Press, 2005, vol. 5, pp. 58-61, with English translation, titled 16 pages.

Wang et al., "Rate of Evolution in Brain-Expressed Genes in Humans and Other Primates", PLoS Biol., 2007, vol. 5, No. 2: e13, pp. 0335-0342, 8 pages.

Wang et al., "Intravenous administration of bone marrow mesenchymal stromal cells is safe for the lung in a chronic myocardial infarction model", Regen. Med., 2011, vol. 6, No. 2, pp. 179-190, 12 pages.

Y. Wang, "Biology of hematopoietic stem cell and the research method thereof", Science Press, 2007, $1^{st}$ Edition, pp. 56-58, with English translation, 10 pages.

Weintraub et al., "Dilated cardiomyopathy", Lancet, 2017, vol. 390, pp. 400-414, 15 pages.

Wexler et al., "Adult Bone Marrow is a Rich Source of Human Mesenchymal 'Stem' Cells but Umbilical Cord and Mobilized Adult Blood are Not", British Journal of Haematology, 2003, vol. 121, No. 2, pp. 368-374, 7 pages.

Whisstock et al., "Prediction of Protein Function from Protein Sequence and Structure", Quarterly Reviews of Biophysics, 2003, vol. 36, No. 3, pp. 307-340, 34 pages.

Witkowski et al., "Conversion of a β-Ketoacyl Synthase to a Malonyl Decarboxylase by Replacement of the Active-Site Cysteine with Glutamine", Biochemistry, 1999, vol. 38, pp. 11643-11650, 8 pages.

Wolf et al., "From the Periphery of the Glomerular Capillary Wall Toward the Center of Disease", Diabetes, 2005, vol. 54, pp. 1626-1634, 9 pages.

Woodbury et al., "Adult Rat and Human Bone Marrow Stromal Cells Differentiate into Neurons", Journal of Neuroscience Research, 2000, vol. 61, pp. 364-370, 7 pages.

Wu et al., "Mesenchymal Stem Cells Enhance Wound Healing Through Differentiation and Angiogenesis", Stem Cells, 2007, vol. 25, pp. 2648-2659, 12 pages.

Yamaoka et al., "1043 Systemic delivery of HMGB1 peptide ameliorates imiquimod-induced psoriasis-like dermatitis", Journal of Investigative Dermatology, 2018, vol. 138, No. 5, S177, 2 pages.

YBOX1_HUMAN Sequence, Accession No. P67809, Oct. 2004, 11 pages.

Yuan et al., "Differentiation of Mesenchymal Stem Cells in Cardiomyogenic Cells Under the Induction of Myocardial Cell Lysate", Chinese Journal of Cardiology, 2005, vol. 33, No. 2, pp. 170-173, with English Translation, 12 pages.

Yu et al., "Impact of Repeated Intravenous Bone Marrow Mesenchymal Stem Cells Infusion on Myocardial Collagen Network Remodeling in a Rat Model of Doxorubicin-Induced Dilated Cardiomyopathy", Molecular and Cellular Biochemistry, 2014, vol. 387, pp. 279-285, 13 pages.

Zhou et al., "Section 2 The translation process of genetic information", Molecular Genetics, 1992, pp. 141-143, 7 pages.

Zhou et al., "High mobility group box 1 protein attenuates myocardial ischemia reperfusion injury via inhibition of the p38 mitogen-activated protein kinase signaling pathway", Experimental and Therapeutic Medicine, 2017, vol. 14, pp. 1582-1588, 7 pages.

International Preliminary Report on Patentability issued Apr. 27, 2021 in International (PCT) Application No. PCT/JP2019/042015.

International Search Report issued Jan. 1, 2020 in International (PCT) Application No. PCT/JP2019/042015.

Taniguchi et al., "Stage-Specific Secretion of HMG1 in Cartilage Regulates Endochondral Ossification", Molecular and Cellular Biology, 2007, vol. 27. No. 16, pp. 5650-5663, 14 pages.

(56) References Cited

OTHER PUBLICATIONS

Tamai et al., "Chapter 2 Various disease models and drug discovery research, 7. Skin and inflammatory disease, 2) Prospects for the development of in vivo regenerative induction drug using in vivo bone marrow mesenchymal stem/progenitor cell mobilzation factor", Gene & medicine, Mook, 2012, vol. 22, pp. 207-212, (with partial English translation), 11 pages.

Lee et al., "Fully reduced HMGB1 accelerates the regeneration of multiple tissues by transitioning stem cells to $G_{Alert}$", PNAS, 2018, vol. 115, No. 19, pp. E4463-E4472, 10 pages.

Sugawara et al., "Artificial organ—Recent advanced, Recent advanced in cartilage loss treatment by cultured cartilage", Jinko Zoki, 2013, vol. 42, No. 3, pp. 198-200, (with partial English Translation) 4 pages.

Freitag et al., "The effect of autologous adipose derived mesenchymal stem cell therapy in the treatment of a large osteochondral defect of the knee following unsuccessful surgical intervention of osteochondritis dissecans—a case study", BMC Musuculoskelet Disord., 2017, vol. 18, No. 1, p. 298 (p. 1-11), 11 pages.

Bianchi et al., "The DNA binding site of HMG1 protein is composed of two similar segments (HMG boxes), both of which have counterparts in other eukaryotic regulatory proteins", EMBO Journal, 1992, vol. 11, No. 3, pp. 1055-1063, 9 pages.

Michael Bustin, Regulation of DNA-Dependent Activities by the Functional Motifs of the High-Mobility Group Chromosomal Proteins, Molecular and Cellular Biology, 1999, vol. 19, No. 8, pp. 5237-5246, 10 pages.

Chamberlain et al., "Concise Review: Mesenchymal Stem Cells: Their Phenotype, Differentiation Capacity, Immunological Features, and Potential for Homing", Stem Cells, 2007, vol. 11, No. 11, pp. 2739-2749, 11 pages.

Charoonpatrapong et al., "HMGB1 Expression and Release by Bone Cells", Journal of Cellular Physiology, 2006, vol. 270, pp. 480-490, 11 pages.

Chen et al., "Involvement of high mobility group box-1 in imiquimod-induced psoriasis-like mice model", Journal of Dermatology, 2017, vol. 44, pp. 573-581, 9 pages.

Chopp et al., "Treatment of neural injury with marrow stromal cells", The Lancet Neurology, 2002, vol. 1, pp. 92-100, 9 pages.

Chou et al., "Identity of nuclear high-mobility-group protein, HMG-1, and sulfoglucuronyl carbohydrate-binding protein, SBP-1, in brain", Journal of Neurochemistry, 2001, vol. 77, pp. 120-131, 12 pages.

De Souza et al., "HMGB1 in vascular diseases: Its role in vascular inflammation and atherosclerosis", Autoimmunity Reviews, 2012, vol. 11, pp. 909-917, 9 pages.

Degryse et al., "The High Mobility Group (HMG) Boxes of the Nuclear Protein HMG1 Induce Chemotaxis and Cytoskeleton Reorganization in Rat Smooth Muscle Cells", Journal of Cell Biology, 2001, vol. 52, No. 6, pp. 1197-1206, 10 pages.

Dong et al., "HMGB1 Protein Does Not Mediate the Inflammatory Response in Spontaneous Spinal Cord Regeneration", Journal of Biological Chemistry, 2013, vol. 288, No. 25, pp. 18204-18218, 15 pages.

Ehrchen et al., "The endogenous Toll-like receptor 4 agonist S100A8/S100A9 (calprotectin) as innate amplifier of infection, autoimmunity, and cancer", Journal of Leukocyte Biology, 2009, vol. 86, No. 3, pp. 557-566, 11 pages.

Esposito et al., "Melatonin reduces stress-activated/mitogen-activated protein kinases in spinal cord injury", Journal of Pineal Research, 2009, vol. 46. No. 1, pp. 79-86, 8 pages.

Fang et al., "HMGB1 Contributes to Regeneration After Spinal Cord Injury in Adult Zebrafish", Mol Neurobiol, 2014, vol. 49, pp. 472-483, 12 pages.

Forte et al., "Hepatocyte Growth Factor Effects on Mesenchymal Stem Cells: Proliferation, Migration, and Differentiation", Stem Cells, 2006, vol. 24, pp. 23-33, 11 pages.

Fujii et al., "Roles of Bone Morphogenetic Protein Type I Receptors and Smad Protein in Osteoblast and Chondroblast Differentiation", Molecular Biology of the Cell, 1999, vol. 10, pp. 3801-3813, 13 pages.

Germani et al., "Pivotal Advance: High-mobility group box 1 protein—a cytokine with a role in cardiac repair", Journal of Leukocyte Biology, 2007, vol. 81, pp. 41-45, 6 pages.

Gong et al., "The Anti-Inflammatory Activity of HMGB1 A Box Is Enhanced When Fused with C-Terminal Acidic Tail", Journal of Biomedicine and Biotechnology, vol. 2010, Article ID 915234, 6 pages.

Granero-Molto et al., "Role of mesenchymal stem cells in regenerative medicine: application to bone and cartilage repair", Expert Opinion on Biological Therapy, 2008, vol. 8, No. 3, pp. 255-268, 14 pages.

Harris et al., "The nuclear protein HMGB1 as a proinflammatory mediator", Eur. J. Immunol., 2004, vol. 34, pp. 1503-1512, 10 pages.

Harris et al., "Alarmin (g) news about danger, Workshop on Innate Danger Signals and HMGB1", EMBO reports, 2006, vol. 7, pp. 774-778, 5 pages.

Huttunen et al., "Receptor for Advanced Glycation End Products-binding COOH-Terminal Motif of Amphoterin Inhibits Invasive Migration and Metastasis", Cancer Research, 2002, vol. 62, pp. 4805-4811, 8 pages.

Jayaraman et al. "High mobility group protein-1 (HMG-1) is a unique activator of p53", Genes & Development, 1998, vol. 12, pp. 462-472, 11 pages.

Kawabata et al., "High Mobility Group Box 1 Is Upregulated After Spinal Cord Injury and Is Associated With Neuronal Cell Apoptosis", Spine, vol. 35 No. 11, pp. 1109-1115, 7 pages.

Kern et al., "Comparative Analysis of Mesenchymal Stem Cells from Bone Marrow, Umbilical Cord Blood, or Adipose Tissue", Stem Cells, 2006, vol. 26, pp. 1294-1301, 8 pages.

Kessler et al., "Tissue engineering and cartilage", Organogenesis, 2008, vol. 4, No. 1, pp. 28-32, 5 pages.

Kikuchi et al., "HMGB1 as a therapeutic target in spinal cord injury: A hypothesis for novel therapy development (Review)", Experimental and Therapeutic Medicine, 2011, vol. 2, pp. 767-770, 4 pages.

Kitahara et al., "High-mobility group box 1 restores cardiac function after myocardial infarction in transgenic mice", Cardiovascular Research, 2008, vol. 80, pp. 40-46, 7 pages.

Koc et al., "Mesenchymal stem cells: heading into the clinic", Bone Marrow Transplantation, 2001, vol. 27, pp. 235-239, 5 pages.

Kokkola et al., "RAGE is the Major Receptor for the Proinflammatory Activity of HMGB1 in Rodent Marcophages", Scandinavian Journal of Immunology, 2005, vol. 61, pp. 1-9; 9 pages.

Laflamme et al., "Regenerating the heart", Nature Biotechnology, 2005, vol. 23, No. 7, pp. 845-856, 12 pages.

Li et al., "Emerging role of HMGB1 in fibrotic diseases", J. Cell. Mol. Med., 2014, vol. 18, No. 12, pp. 2231-2339, 9 pages.

Limana et al., "Exogenous High-Mobility Group Box 1 Protein Induces Myocardial Regeneration After Infarction via Enhanced Cardiac C-Kit$^+$Cell Proliferation and Differentiation", Circulation Research, 2005, No. 97, pp. e73-e83, 11 pages.

Lin et al., "The Isolation of Novel Mesenchymal Stromal Cell Chemotactic Factors from the Conditioned Medium of Tumor Cells", Exp Cell Res., 2008, vol. 314, No. 17, pp. 3107-3117, 20 pages.

Martin-Murphy et al., "The Role of Damage Associated Molecular Pattern Molecules in Acetaminophen-Induced Liver Injury in Mice", Toxicol Lett., 2010, vol. 192, No. 3, pp. 387-394, 20 pages.

Merenmies et al., "30-kDa Heparin-binding Protein of Brain (Amphoterin) Involved in Neurite Outgrowth", Journal of Biological Chemistry, 1991, vol. 226, No. 25, pp. 16722-16729, 8 pages.

Mistry et al., "Recombinant HMG1 Protein Produced in Pichia pastoris: A Nonviral Gene Delivery Agent" BioTechniques, 1997, vol. 22, pp. 718-729, 11 pages.q Muhammad et al., "The HMGB1 Receptor RAGE Medicates Ischemic Brain Damage", Journal of Neuroscience, 2008, vol. 28, No. 46, pp. 12023-12031, 9 pages.

(56) References Cited

OTHER PUBLICATIONS

Müller et al., The double life of HMGB1 chromatin protein: architectural factor and extracellular signal, EMBO Journal, 2001, vol. 20, No. 16, pp. 4337-4340, 4 pages.
Nakamura et al., "p38 Mitogen-Activated Protein Kinase Functionally Contributes to Chondrogenesis Induced by Growth/Differentiation Factor-5 in ATDC5 Cells", Experimental Cell Research, 1999, vol. 250, pp. 351-363, 13 pages.
Narumi et al., "High-Mobility group box 1-mediated heat shock protein beta 1 expression attenuates mitochondrial dysfunction and apoptosis", Journal of Molecular and Cellular Cardiology, 2015, vol. 82, pp. 1-12, 12 pages.
Palumbo et al., "Cells migrating to sites of tissue damage in response to the danger signal HMGB1 require NF-κB activation", Journal of Cell Biology, 2007, vol. 179, No. 1, pp. 33-40, 8 pages.
Palumbo et al., "Extracellular HMGB1, a signal of tissue damage, induces mesoangioblast migration and proliferation", Journal of Cell Biology, 2004, vol. 164, No. 2, pp. 441-449, 9 pages.
Palumbo et al., "High mobility group box 1 protein, a cue for stem cell recruitment", Biochemical Pharmacology, 2004, vol. 68, pp. 1165-1170, 6 pages.
Pandya et al., "Angiogenesis—a new target for future therapy", Vascular Pharmacology, 2006, vol. 44, pp. 265-274, 10 pages.
Pankov et al., "Fibronectin at a glance", Journal of Cell Science, 2002, vol. 115, pp. 3861-3863, 3 pages.
Park et al., "Involvement of Toll-like Receptors 2 and 4 in Cellular Activation by High Mobility Group Box 1 Protein", Journal of Biological Chemistry, 2004, vol. 279, No. 9, pp. 7370-7377, 8 pages.
Pittenger et al., "Multilineage Potential of Adult Human Mesenchymal Stem Cells", Science, 1999, vol. 284, pp. 143-147; 6 pages.
Popovic et al., "Increased Expression of the Novel Proinflammatory Cytokine High Mobility Group Box Chromosomal Protein 1 in Skin Lesions of Patients With Lupus Erythematosus", Arthritis & Rheumatism, 2005, vol. 52, No. 11, pp. 3369-3645, 7 pages.
Raucci et al., "The Janus face of HMGB1 in heart disease: a necessary update", Cellular and Molecular Life Sciences, 2019, vol. 76, pp. 211-229, 19 pages.
Sasaki et al., "Mesenchymal Stem Cells are Recruited into Wounded Skin and Contribute to Wound Repair by Transdifferentiation into Multiple Skin Cell Type", Journal of Immunology, 2008, vol. 180, pp. 2581-2587, 8 pages.
Straino et al., "High-Mobility Group Box 1 Protein in Human and Murine Skin: Involvement in Wound Healing", Society for Investigative Dermatology, 2008, vol. 128, pp. 1545-1553, 9 pages.
Sun et al., "Isolation of Mouse Marrow Mesenchymal Progenitors by a Novel and Reliable Method", Stem Cells, 2003, vol. 21, pp. 527-535, 9 pages.
Tagami et al., "Elevation of serum high-mobility group box 1 protein during granulocyte colony-stimulating factor-induced peripheral blood stem cell mobilisation", British Journal of Haematology, 2006, vol. 135, pp. 567-569, 3 pages.
Tagliafico et al., "TGFβ/BMP activate the smooth muscle/bone differentiation programs in mesoangioblasts, Journal of Cell Science, 2004, vol. 117, pp. 4377-4388, 12 pages.
Takahashi et al., "Modulated Inflammation by Injection of High-Mobility Group Box 1 Recovers Post-Infarction Chronically Failing Heart", Circulation, 2008, vol. 118, pp. S106-S114, 9 pages.
Tang et al., "High-Mobility Group Box 1, Oxidative Stress, and Disease", Antioxidants & Redox Signaling, 2011, vol. 14, No. 7, pp. 1315-1335, 22 pages.
Tao et al., "Cardiomyocyte-fibroblast interaction contributes to diabetic cardiomyopathy in mice: Role of HMGB1/TLR4/IL-33 axis", Biochimica et Biophysica Acta, 2015, vol. 1852, pp. 2075-2085, 11 pages.
Telusma et al., "Dendritic cell activating peptides induce distinct cytokine profiles", International Immunology, 2006, vol. 18, No. 11, pp. 1563-1573, 11 pages.
Tsung et al., "Hepatic Ischemia/Reperfusion Injury Involves Functional TLR4 Signaling in Nonparenchymal Cells", Journal of Immunology, 2005, vol. 175, pp. 7661-7668, 9 pages.
Ulloa et al., "High-mobility group box 1 (HMGB1) protein: Friend and foe", Cytokine & Growth Factor Reviews, 2006, vol. 17, pp. 189-201, 13 pages.
Venereau et al., "Mutually exclusive redox forms of HMGB1 promote cell recruitment or proinflammatory cytokine release", J. Exp. Med. 2012, vol. 209, No. 9, pp. 1519-1528, 10 pages.
Wang et al., "Overexpression of HMGB1 A-box reduced lipopolysaccharide-induced intestinal inflammation via HMGB1/TLR4 signaling in vitro", World Journal of Gastroenterology, 2015, vol. 21, No. 25, pp. 7764-7776, 14 pages.
Wang et al., "HMG-1 as a Late Mediator of Endotoxin Lethality in Mice", Science, 1999, vol. 285, pp. 248-251, 5 pages.
Watanabe et al., "The Role of HMGB-1 on the Development of Necrosis During Hepatic Ischemia and Hepatic Ischemia/Reperfusion Injury in Mice", Journal of Surgical Research, 2005, vol. 124, pp. 59-66, 8 pages.
Yamada et al., "Regulation of osteoclast development by Notch signaling directed to osteoclast precursors and through stromal cells", Blood, 2003, vol. 101, pp. 2227-2234, 8 pages.
Yang et al., "High mobility group box-1 protein induces the migration and activation of human dendritic cells and acts as an alarmin", Journal of Leukocyte Biology, 2007, vol. 81, pp. 59-66, 9 pages.
Yang et al., "Reversing established sepsis with antagonists of endogenous high-mobility group box 1", PNAS, 2004, vol. 101, No. 1, pp. 296-301, 6 pages.
Yang et al., "Does pretreatment of bone marrow mesenchymal stem cells with 5-azacytidine or double intravenous infusion improve their therapeutic potential for dilated cardiomyopathy?", Medical Science Monitor Basic Research, 2013, vol. 19, pp. 20-31, 12 pages.
Youn et al., "High Mobility Group Box 1 Protein Binding to Lipopolysaccharide Facilitates Transfer of Lipopolysaccharide to CD14 and Enhances Lipopolysaccharide-Medicated TNF-α Production in Human Monocytes", Journal of Immunology, 2008, vol. 180, pp. 5067-5074, 9 pages.
Zheng et al., "Adeno-associated virus-mediated colonic secretory expression of HMGB1 A box attenuates experimental colitis in mice", J Gene Med, 2016, vol. 18, pp. 261-272, 12 pages.
Zhou et al., "Exogenous High-Mobility Group Box 1 Protein Injection Improves Cardiac Function after Myocardial Infarction: Involvement of Wnt Signaling Activation", Journal of Biomedicine and Biotechnology, 2012, Article ID 743879, pp. 1-5, 5 pages.
Extended European Search Report issued Jun. 28, 2022 in corresponding European Patent Application No. 19875071.3, 9 pages.
Tamai, Katsuto et al., "PDGFRα-positive cells in bone marrow are mobilized by high mobility group box 1 (HMGB1) to regenerate injured epithelia", PNAS, 2011, vol. 108, No. 16, pp. 6609-6614.
Tamai, Katsuto, "Development of regeneration-inducing medicine using biological damaged tissue regeneration mechanism of peripheral circulatory mesenchymal cells", BIO Clinica, 2016, vol. 31, No. 10, pp. 34-38, with English Translation.
Tamai, Katsuto et al., "179 Systemic administration of HMGB1 peptide drastically improves survival of the RDEB model mice by mobilizing multipotent stem/progenitor cells from bone marrow", Journal of Investigative Dermatology, 2017, vol. 137, No. 10, Supplement 2, p. S223.
Tamai, Katsuto, "Study on the practical application of new drugs for epidermolysis bullosa", 2014 Outsourcing performance report, MHLW Grants System [online], with its Partial English Translation of pp. 155-157 & Fig. 4-1.
Sawa, Yoshiki, "Drug discovery research for corresponding to unmet needs in the brain and cardiovascular area", 2012 Research report on generalization and allotment, MHLW Grants System [online], with its Partial English Translation of pp. 7-8.
Shimbo, Takashi et al., "Characterization analysis of peripheral circulating PDGFRα-positive mesenchymal stem cells by comprehensive gene expression analysis", The Japanese Society for Regenerative Medicine [online], with English Translation, 4 pages.
International Search Report issued Feb. 19, 2019 in corresponding International (PCT) Patent Application No. PCT/JP2018/044282.

(56) References Cited

OTHER PUBLICATIONS

International Preliminary Report on Patentability (Chapter I of the Patent Cooperation Treaty) issued Feb. 19, 2019 in corresponding International (PCT) Patent Application No. PCT/JP2018/044282.
Office Action and Search Report issued Apr. 12, 2023, in the corresponding Chinese Patent Application No. 201880088377.3, with English translation.
Dongjie et al., "Research progress on the mechanism and induction methods for the differentiation of mesenchymal stem cells", Infection, Inflammation, Repair, 2011, vol. 12, No. 1, pp. 62-64.
Office Action and Search Report issued Feb. 9, 2023, in corresponding Russian Patent Application No. 2021114359, with English translation, 16 pages.
Yang et al., "The many faces of HMGB1: molecular structure-functional activity in inflammation, apoptosis, and chemotaxis", Journal of Leukocyte Biology, 2013, vol. 93, No. 6, pp. 865-873, 9 pages.
Preliminary Office Action issued Sep. 19, 2023 in corresponding Brazilian Patent Application No. BR112021007732-4, with English translation, 8 pages.
Office Action and Search Report issued Sep. 19, 2023 in corresponding Chinese Patent Application No. 201880088377.3, with English translation, 30 pages.
Katsuto Tamai, "Cross-talk between bone marrow mesenchymal stem cells and injured tissue", 2016, Ann Jpn Prosthodont Soc; vol. 8, pp. 342-345, with partial English translation, 5 pages.
Office Action issued Aug. 8, 2023 in corresponding Japanese Patent Application No. 2020-552636, with English machine translation, 8 pages.
Office Action issued Dec. 4, 2023 in Japanese Patent Application No. 2023-007554, with English machine translation, 11 pages.
Zhao et al., "The Study Progression of the Role of HMGB1 in Ischemic Heart Failure", pp. 1169-1171.
Kaneko et al., "Bone Marrow Mononuclear Cell Transplantation Improves Cardiac Function in Ischemic Cardiomyopathy via High Mobility Group Box 1 Released from Dead Donor Cells: Abstract 11250", Circulation, 2012, vol. 126, Issue 21, Supplement, 20, pp. 1-2.
Narumi et al., "Cardiac-Specific Overexpression of High-Mobility Group Box 1 Protects Cardiomyocyte from Apoptosis During the Pathogenesis of Doxorubicin Cardiomyopathy: Abstract 15265", Circulation, 2012, vol. 126, Issue 21, Supplement, 20, pp. 1-2.
Funayama et al., "Cardiac nuclear high mobility group box 1 prevents the development of cardiac hypertrophy and heart failure", Cardiovascular Research, 2013, vol. 99, pp. 657-664.
Lotze et al., "High-Mobility Group Box 1 Protein (HMGB1): Nuclear Weapon in the Immune Arsenal", Nature Reviews, Immunology, 2005, vol. 5, pp. 331-342.
Fenton et al., "Rheostat positions: A new classification of protein positions relevant to pharmacogenomics", Medicinal Chemistry Research, 2020, vol. 29, pp. 1133-1146.
Bhattacharya et al., "Impact of genetic variation on three-dimensional structure and function of proteins", PLoS ONE, 2017, vol. 12, No. 3, e0171355, pp. 1-22.
Guo et al., "Protein tolerance to random amino acid change", PNAS, 2004, vol. 101, No. 25, pp. 9205-9210.
Bigazzi. "Introduction to Review Series on Animal Models of Human Disease", Clinical Immunology and Immunopathology, 1995, vol. 74, No. 1, p. 1.
Bretag, "Too much hype, not enough hope: Are balanced reporting and proper controls too much to expect from therapeutic studies in animal models of neuromuscular diseases that presage clinical trials in humans?", Neuromuscular Disorders, 2007, vol. 17, pp. 203-205.
Sisakian et al., "Dilated Cardiomyopathy: Evolution of Pathogenesis Concepts and Potential for New Therapies", The New Armenian Medical Journal, 2015, vol. 9, No. 1, p. 4-18.
Justice et al., "Using the mouse to model human disease: increasing validity and reproducibility", Disease Models & Mechanisms, 2016, vol. 9, pp. 101-103.

Del Buono et al., "Ischemic Cardiomyopathy and Heart Failure After Acute Myocardial Infarction", Current Cardiology Reports, 2022, vol. 24, pp. 1505-1515.
Office Action issued Oct. 28, 2022 in corresponding Chinese Patent Application No. 201880008721.3, with English language translation, 35 pages.
Office Action issued Jan. 18, 2023 in corresponding U.S. Appl. No. 16/477,878, 26 pages.
Office Action issued Dec. 15, 2022 in corresponding Singapore Patent Application No. 11202104015Y, 9 pages.
Office Action issued Nov. 16, 2023 in Israeli Patent Application No. 282377, 4 pages.
Office Action issued Nov. 15, 2022 in corresponding Japanese Patent Application No. 2019-556765, with English translation, 14 pages.
Office Action issued Dec. 6, 2023 in corresponding Canadian Patent Application No. 3,084,013, 6 pages.
Yan et al. "Migration of Dorsal Aorta Mesenchymal Stem Cells Induced by Mouse Embryonic Circulation", Developmental Dynamics, 2011, vol. 240, pp. 65-74, 10 pages.
Office Action issued Apr. 30, 2024 in corresponding Korean Patent Application No. 10-2020-7018355, with English-language Translation.
Hiroshi Kawada, et al., "Nonhematopoietic mesenchymal stem cells can be mobilized and differentiate into cardiomyocytes after myocardial infarction", Blood, vol. 104, No. 12, pp. 3581-3587, (2004).
Ryo Ukai, et al., "Mesenchymal Stem Cells Derived from Peripheral Blood Protects against Ischemia", Journal of Neurotrauma, vol. 24, No. 3, pp. 508-520, (2007).
Office Action issued Jan. 15, 2024 in corresponding Canadian Patent Application No. 3,117,107, 4 pages.
Office Action issued Apr. 23, 2024 in U.S. Appl. No. 17/287,636, pp. 1-93.
Hsu et al., "Knee Osteoarthritis", StatPearls [Internet], Treasure Island (FL): StatPearls Publishing; Available from: https://www.ncbi.nlm.nih.gov/books/NBK507884/, Jan. 2024, pp. 1-13.
Andersson et al., "HMGB1 is a potent trigger of arthritis", Journal of Internal Medicine, 2004, vol. 255, pp. 344-350.
Kokkola et al., "Successful Treatment of Collagen-Induced Arthritis in Mice and Rats by Targeting Extracellular High Mobility Group Box Chromosomal Protein 1 Activity", Arthritis & Rheumatism, Jul. 2023, vol. 48, No. 7, pp. 2052-2058.
Kokkola et al., "Successful Treatment of Collagen-Induced Arthritis in Mice and Rats by Targeting Extracellular High Mobility Group Box Chromosomal Protein 1 Activity", Arthritis & Rheumatism, Jul. 2003, vol. 48, No. 7, pp. 2052-2058.
David D Brand et al., "Collagen-induced arthritis", Nature Protocols, 2007, vol. 2, No. 5, pp. 1269-1275.
Sheila L. Arvikar et al., "Inflammatory bowel disease associated arthopathy", Curr Rev Musculoskelet Med, 2011, vol. 4, pp. 123-131.
Yamaguchi Igaku, "Establishment of canine liver fibrosis model and evaluation of the efficacy of cultured autologous bone marrow-derived mesenchymal stem cell infusion", (Yamaguchi Medical Journal) (2016), vol. 65, Issue 4, p. 196, with English translation.
First Office Action issued Jan. 6, 2024 in corresponding Chinese Patent Application No. 201980085703.X, with English language translation.
Office Action issued Dec. 31, 2024, in the corresponding Korean Patent Application No. 10-2021-7015301 with English-language translation.
Andersson, et al., "The role of HMGB1 in the pathogenesis of rheumatic Disease", Biochimica et Biophysica Acta, 2010, vol. 1799, pp. 141-148.
Stros, "HMGB proteins: Interactions with DNA and chromatin", Biochimica et Biophysica Acta, 2010, vol. 1799, pp. 101-113.
Office Action issued Oct. 2, 2024 in related U.S. Appl. No. 17/287,636.
B. Vanwanseele et al., "Knee Cartilage of Spinal Cord-Injured Patients Displays Progressive Thinning in the Absence of Normal Joint Loading and Movement", Arthritis & Rheumatism, vol. 46, No. 8 (Aug. 2002), pp. 2073-2078.

(56) References Cited

OTHER PUBLICATIONS

S. Hinteiwimmer et al., "Cartilage Atrophy in the Knees of Patients After Seven Weeks of Partial Load Bearing", Arthritis & Rheumatism, vol. 50, No. 8 (Aug. 2004), pp. 2516-2520.

Nicolas V. Jaumard et al., "Spinal Facet Joint Biomechanics and Mechanotransduction in Normal, Injury and Degenerative Conditions", Journal of Biomechanical Engineering (Jul. 2011), vol. 133, pp. 071010-1-071010-31.

J. Anderson et al., "Cartilage Atrophy Following Spinal Cord Damage", Australasian Radiology, vol. XXV, No. 1 (Mar. 1981), pp. 98-103.

James R. Taylor, MD, PhD, "Neck Sprain", British Columbia Medical Journal, vol. 44, No. 5, Jun. 2002, pp. 252-256.

\* cited by examiner

Fig. 27
a
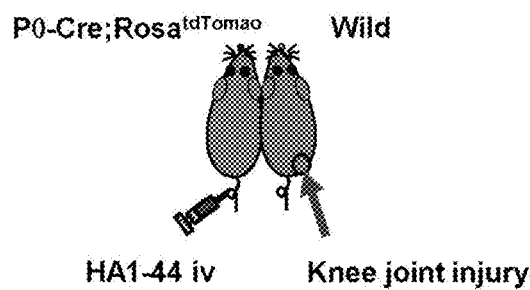
b
Control HA1-44
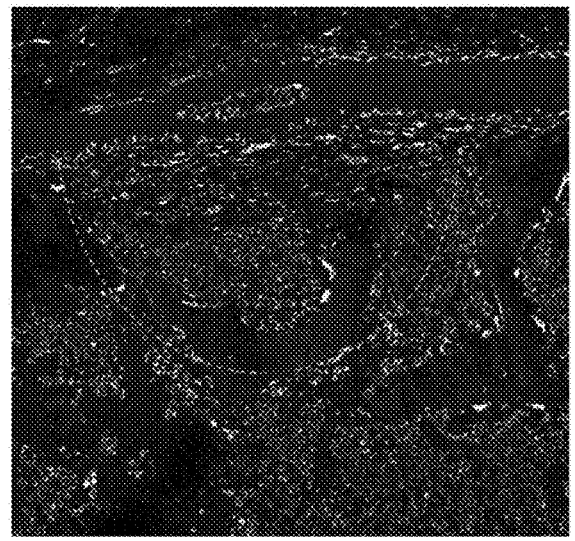

Fig. 29

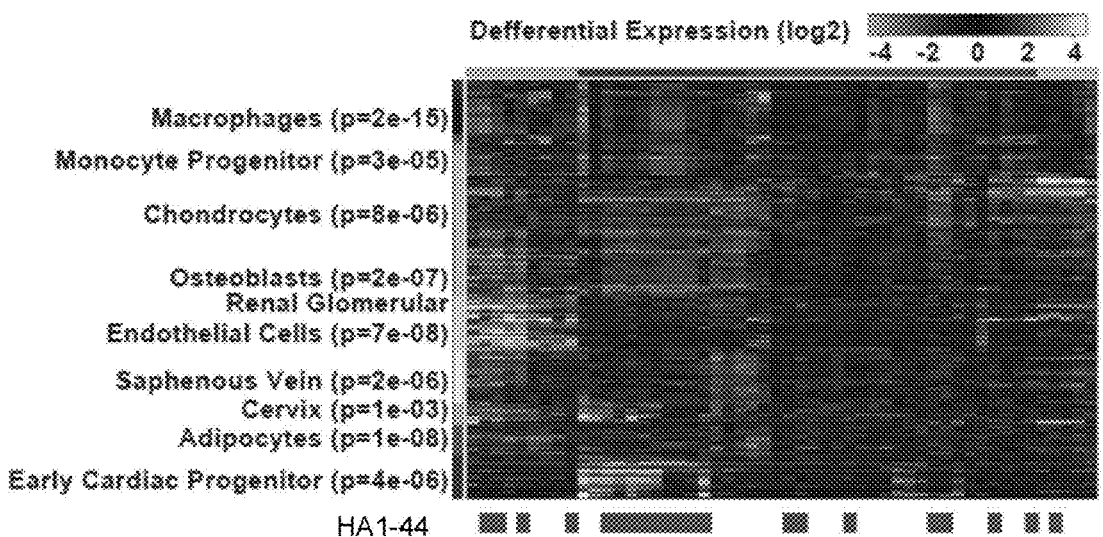

Fig. 30

| | | Cluster | | | |
|---|---|---|---|---|---|
| | | 1 | 2 | 3 | 4 |
| Predicted cell types | Macrophages and the like | − | − | + | − |
| | Monocyte Progenitor and the like | − | − | + | − |
| | Chondrocytes and the like | − | − | + | + |
| | Osteoblasts and the like | + | − | − | + |
| | Renal Glomerular Endothelial Cells and the like | + | − | − | + |
| | Saphenous Vein and the like | + | − | − | + |
| | Cervix and the like | + | + | − | + |
| | Adipocytes and the like | − | + | − | + |
| | Early Cardiac Progenitor and the like | − | + | − | − |
| | The number of colonies in HA1-44 group | 4 | 9 | 7 | 1 |
| | The number of colonies in saline group | 5 | 5 | 17 | 4 |

+: High expression
−: Low expression

ECTODERMAL MESENCHYMAL STEM CELLS AND METHOD FOR PRODUCING SAME

TECHNICAL FIELD

The present invention relates to an ectomesenchymal stem cell and a method for producing the same. The present invention also relates to a method for screening for a multipotent stem cell inducer.

BACKGROUND ART

Mesenchymal stem cells (MSCs) contained in bone marrow fluids and the like have differentiation potency into various tissues, such as bone, cartilage, fat, muscle, nerve, and epithelium (multi-lineage differentiation potency). Thus, attempts to provide regenerative medicine (cell transplant therapy) using MSCs have become widespread in recent years. However, it is known that MSCs previously used in regenerative medicine gradually lose their proliferation ability and multi-lineage differentiation potency when they are continuously passaged in vitro. It is thus required to find a cell that has higher ability to promote tissue regeneration than common MSCs or a substance that has the effect of activating/inducing the cell in vivo, and to provide a therapeutic method that is more effective than conventional regenerative medicine.

CITATION LIST

Patent Literature

Patent Literature 1: WO 2012/147470

Non Patent Literature

Non Patent Literature 1: PNAS 2011 Apr. 19; 108(16): 6609-14

SUMMARY OF INVENTION

Technical Problem

An object of the present invention is to provide an ectomesenchymal stem cell and a method for producing the same. Another object of the present invention is to provide a method for screening for a multipotent stem cell inducer.

Solution to Problem

The present inventors have found that ectomesenchymal stem cells (EMSCs) induced by necrotic tissue injury and circulating in peripheral blood contribute to the regeneration of injured tissues. This finding is based on the discovery, previously reported by the present inventors (PNAS 2011 Apr. 19; 108(16): 6609-14), of a mechanism whereby "HMGB1 released from necrotic tissue in the exfoliated epidermis in epidermolysis bullosa causes bone marrow mesenchymal stem cells to accumulate in the exfoliated epidermis site via peripheral blood circulation to induce regeneration of the injured skin," and further based on the results obtained this time, that are "when a skin of an epidermolysis bullosa mouse is grafted on one side of the parabiosis model and a fragment peptide of HMGB1 is administered on the other side, PDGFRα lineage-positive cells accumulate in the skin graft site to regenerate epidermis" and "when a cartilage injury is created in a mouse and a fragment peptide of HMGB1 is administered, P0 lineage-positive cells accumulate in the cartilage injury site via peripheral blood circulation to regenerate a cartilage tissue", and the like. The present inventors also obtained experimental results suggesting that the source of EMSC in peripheral blood may be a certain PDGFRα-positive cell in the bone marrow and that EMSC in peripheral blood may be a cell whose embryological origin is ectomesenchyme generated from the epidermal side of the cranial neural fold. Based on such discoveries, the present inventors have completed the inventions of an ectomesenchymal stem cell, a method for producing the same, and a method for screening for a substance having multipotent stem cell inducing activity, using a cell in peripheral blood induced by a necrotic tissue injury as an indicator.

The present inventors have previously found that a peptide consisting of the amino acid sequence of positions 1-44 (MGKGDPKKPRGKMSSYAFFVQTCREEHKKKHP-DASVNFSEFSKK) (SEQ ID NO:1) (hereinafter referred to as "HA1-44 peptide") at the N-terminus of A-box of HMGB1 protein mobilizes multipotent stem cells such as mesenchymal stem cells (MSCs) from bone marrow into peripheral blood to exert a therapeutic effect in various disease models. This time, the present inventors have newly found that administration of the HA1-44 peptide causes reactions in an organism ((i) a change in the configuration of the PDGFRα-positive cell population in peripheral blood, (ii) an increase in the number of PDGFRα-positive cells in peripheral blood, and (iii) a change in gene expression of PDGFRα-positive cells in vertebral bone marrow). Then, the present inventors have found a method for screening for a substance having similar activity to the HA1-44 peptide, i.e., a multipotent stem cell inducer, using these reactions as an indicator, and completed the present invention. That is, the present invention provides a method for determining whether a test substance has similar activity to an HA1-44 peptide (the activity of promoting induction and/or mobilization of multipotent stem cells and/or promoting tissue regeneration), based on whether the same reaction as any of (i) to (iii) above occurs by administering a test substance to a subject such as an animal.

The present inventors have also analyzed details of cells that are mobilized by the HA1-44 peptide into peripheral blood and injured tissues and contribute to regeneration of the tissues. As a result, the present inventors have found that (i) cells in peripheral blood that contribute to promoting tissue regeneration by the HA1-44 peptide are PDGFRα-positive cells derived from vertebral bone marrow, (ii) PDGFRα-positive cells derived from vertebral bone marrow have greater differentiation potency into bone, cartilage, and/or fat than PDGFRα-positive cells derived from bone marrows of other bones, and (iii) a small amount of PDGFRα-positive cells having the developmental lineage (Prx1 lineage-negative) same as PDGFRα-positive cells derived from vertebral bone marrow are also present in bone marrows from other bones. Based on these findings, the present inventors have found that, by culturing a cell population derived from a biological tissue containing MSCs, such as a bone marrow or peripheral blood on a dish to form a colony, subcloning each colony, and selecting a cell clone exhibiting high differentiation potency to bone, cartilage, and/or fat, multipotent stem cells having a higher ability to promote tissue regeneration than MSCs obtained by conventional methods (which collect a bone marrow and culture on a dish) can be obtained, and have completed the present invention.

Specifically, the present invention relates to the followings:
A) An ectomesenchymal stem cell.
B) A method for producing an ectomesenchymal stem cell.
C) A cell obtained by the method according to item B).
D) A cell or cell population in peripheral blood, induced by an MSC in-blood-mobilizing substance.
E) A cell or cell population in the vertebral bone marrow, induced by a peptide consisting of the amino acid sequence of positions 1-44 (SEQ ID NO: 1) at the N-terminus of A-box of the high-mobility group box 1 (HMGB1) protein (hereinafter also referred to as "HA1-44 peptide").
F) A method for producing the cell or cell population according to item D) or E).
G) A method for obtaining, isolating, and/or enriching a cell having a high tissue regeneration promoting ability similar to a PDGFRα-positive cell in a vertebral bone marrow, from a biological tissue containing a mesenchymal stem cell (MSC).
H) A cell or cell population obtained by the method according to item G).
I) A composition for use in promoting tissue regeneration, containing an ectomesenchymal stem cell.
J) A method for screening for a substance having inducing activity of a multipotent stem cell, using a cell in peripheral blood induced by a necrotic tissue injury as an indicator.
K) A method for screening for a substance having inducing activity of a multipotent stem cell, using an HA1-44 peptide as a positive control and a reaction of multipotent stem cells that contribute to tissue regeneration in vivo as an indicator.
L) A method for determining an expected tissue regeneration promoting effect in a subject to which an MSC in-blood-mobilizing substance has been administered, using a colony-forming Pα cell in peripheral blood as an indicator.

More specifically, the present invention relates to the followings.
a) A colony-forming PDGFR-positive cell having characteristic i) and characteristics ii) and/or iii) below:
   i) having differentiation potency into an osteoblast, an adipocyte, and a chondrocyte;
   ii) having differentiation potency into an epidermal cell;
   iii) being P0 lineage-positive.
b) The cell according to item a), wherein the cell is PDGFRα-positive.
c) A cell according to item a) or b), wherein the cell has one or more characteristics selected from $P\alpha^+$, $P\alpha^{lin+}$, $P0^{lin+}$, $Prx1^{lin-}$, $Sox1^{lin-}$, $LepR^{lin-}$, $CD34^+$, and $Sca1^-$.
d) A vertebral bone marrow-derived cell that is PDGFRα-positive, CD34-positive, and Sca1-negative.
e) A method for producing a colony-forming PDGFR-positive cell, comprising any one of steps 1) to 4) below:
   1) collecting peripheral blood from a subject having a necrotic tissue injury, and culturing the peripheral blood on a solid phase;
   2) collecting peripheral blood from a subject having a necrotic tissue injury, culturing the peripheral blood on a solid phase, and then selectively recovering a cell having one or more characteristics selected from $P\alpha^+$, $P\alpha^{lin+}$, $P0^{lin+}$, $Prx1^{lin-}$, $Sox1^{lin-}$, $LepR^{lin-}$, $CD34^+$, and $Sca1^-$;
   3) collecting peripheral blood from a subject having a necrotic tissue injury, and selectively recovering a cell having one or more characteristics selected from $P\alpha^+$, $P\alpha^{lin+}$, $P0^{lin+}$, $Prx1^{lin-}$, $Sox1^{lin-}$, $LepR^{lin-}$, $CD34^+$, and $Sca1^-$ from the peripheral blood;
   4) collecting peripheral blood from a subject having a necrotic tissue injury, selectively recovering a cell having one or more characteristics selected from $P\alpha^+$, $P\alpha^{lin+}$, $P0^{lin+}$, $Prx1^{lin-}$, $Sox1^{lin-}$, $LepR^{lin-}$, $CD34^+$, and $Sca1^-$ from the peripheral blood, and culturing the cell on a solid phase.
f) A method for producing a colony-forming PDGFR-positive cell, comprising any one of steps 1) to 4) below:
   1) culturing peripheral blood collected from a subject having a necrotic tissue injury on a solid phase;
   2) culturing peripheral blood collected from a subject having a necrotic tissue injury on a solid phase, and then selectively recovering a cell having one or more characteristics selected from $P\alpha^+$, $P\alpha^{lin+}$, $P0^{lin+}$, $Prx1^{lin-}$, $Sox1^{lin-}$, $LepR^{lin-}$, $CD34^+$, and $Sca1^-$;
   3) selectively recovering a cell having one or more characteristics selected from $P\alpha^+$, $P\alpha^{lin+}$, $P0^{lin+}$, $Prx1^{lin-}$, $Sox1^{lin-}$, $LepR^{lin-}$, $CD34^+$, and $Sca1^-$ from peripheral blood collected from a subject having a necrotic tissue injury;
   4) selectively recovering a cell having one or more characteristics selected from $P\alpha^+$, $P\alpha^{lin+}$, $P0^{lin+}$, $Prx1^{lin-}$, $Sox1^{lin-}$, $LepR^{lin-}$, $CD34^+$, and $Sca1^-$ from peripheral blood collected from a subject having a necrotic tissue injury, and culturing the cell on a solid phase.
g) A method for producing a colony-forming PDGFR-positive cell, comprising any one of steps 1) to 4) below:
   1) collecting a vertebral bone marrow from a subject, and culturing the vertebral bone marrow on a solid phase;
   2) collecting a vertebral bone marrow from a subject, culturing the vertebral bone marrow on a solid phase, and then selectively recovering a cell having one or more characteristics selected from $P\alpha^+$, $P0^{lin+}$, $Prx1^{lin-}$, and $Sox1^{lin-}$;
   3) collecting a vertebral bone marrow from a subject, and selectively recovering a cell having one or more characteristics selected from $P\alpha^+$, $P0^{lin+}$, $Prx1^{lin-}$, and $Sox1^{lin-}$ from the vertebral bone marrow;
   4) collecting a vertebral bone marrow from a subject, selectively recovering a cell having one or more characteristics selected from $P\alpha^+$, $P0^{lin+}$, $Prx1^{lin-}$, and $Sox1^{lin-}$ from the vertebral bone marrow, and culturing the cell on a solid phase.
h) A method for producing a colony-forming PDGFR-positive cell, comprising any one of steps 1) to 4) below:
   1) culturing a vertebral bone marrow collected from a subject on a solid phase;
   2) culturing a vertebral bone marrow collected from a subject on a solid phase, and then selectively recovering a cell having one or more characteristics selected from $P\alpha^+$, $P0^{lin+}$, $Prx1^{lin-}$, and $Sox1^{lin-}$;
   3) selectively recovering a cell having one or more characteristics selected from $P\alpha^+$, $P0^{lin+}$, $Prx1^{lin-}$, and $Sox1^{lin-}$ from a vertebral bone marrow collected from a subject;
   4) selectively recovering a cell having one or more characteristics selected from $P\alpha^+$, $P0^{lin+}$, $Prx1^{lin-}$, and $Sox1^{lin-}$ from a vertebral bone marrow collected from a subject, and culturing the cell on a solid phase.
i) A cell population obtained by administering an MSC in-blood-mobilizing substance to a subject, collecting peripheral blood from the subject, and culturing the collected peripheral blood on a solid phase.
j) The cell population according to item i), wherein the MSC in-blood-mobilizing substance is an HA1-44 peptide.
k) A method for producing a cell, comprising a step of administering an MSC in-blood-mobilizing substance to a subject, collecting peripheral blood from the subject, and culturing the collected peripheral blood on a solid phase.

l) A method for producing a cell, comprising a step of culturing peripheral blood collected from a subject to which an MSC in-blood-mobilizing substance has been administered on a solid phase.

m) The method according to item k) or l), wherein the MSC in-blood-mobilizing substance is an HA1-44 peptide.

n) A cell population obtained by 1) administering an HA1-44 peptide to a subject, 2) collecting a vertebral bone marrow from the subject, and 3) culturing the collected bone marrow on a solid phase or sorting a PDGFRα-positive cell from the collected bone marrow.

o) A method for producing a cell, comprising the steps of 1) administering an HA1-44 peptide to a subject, 2) collecting a vertebral bone marrow from the subject, and 3) culturing the collected bone marrow on a solid phase or sorting a PDGFRα-positive cell from the collected bone marrow.

p) A method for producing a cell, comprising a step of culturing a vertebral bone marrow collected from a subject to which an HA1-44 peptide has been administered on a solid phase or sorting a PDGFRα-positive cell from the collected bone marrow.

q) A method for producing a cell population, comprising the steps of:
  1) culturing a cell population from a biological tissue containing MSC on a solid phase;
  2) subcloning a colony obtained in step 1);
  3) culturing a portion of cells obtained by the subcloning in a differentiation-inducing medium into bone, cartilage, and/or fat, and measuring an expression level of a differentiation marker of bone, cartilage, and/or fat; and
  4) selecting a cell clone showing a high expression level compared to the expression level of a differentiation marker of bone, cartilage, and/or fat in case that MSC obtained by culturing a femoral bone marrow on a solid phase are cultured in a differentiation-inducing medium into bone, cartilage, and/or fat.

r) A method for producing a cell population, comprising the steps of:
  1) culturing a cell population derived from a biological tissue containing MSC on a solid phase; and
  2) selecting a colony having one or more characteristics selected from $P\alpha^+$, $P\alpha^{lin+}$, $P0^{lin+}$, $Prx1^{lin-}$, $Sox1^{lin-}$, $LepR^{lin-}$, $CD34^+$, and $Sca1^-$.

s) The method according to item r), wherein step 2) is a step of selecting a Prx1 lineage-negative colony.

t) A method for producing a cell population, comprising a step of selectively recovering a cell having one or more characteristics selected from $P\alpha^+$, $P\alpha^{lin+}$, $P0^{lin+}$, $Prx1^{lin-}$, $Sox1^{lin-}$, $LepR^{lin-}$, $CD34^+$, and $Sca1^-$ from a cell population derived from a biological tissue containing MSC.

u) A method for producing a cell population, comprising the steps of:
  1) selectively recovering a cell having one or more characteristics selected from $P\alpha^+$, $P\alpha^{lin+}$, $P0^{lin+}$, $Prx1^{lin-}$, $Sox1^{lin-}$, $LepR^{lin-}$, $CD34^+$, and $Sca1^-$ from a cell population derived from a biological tissue containing MSC; and
  2) culturing the cell recovered in step 1) on a solid phase.

v) A cell or cell population obtained by the method according to claims *to*.

w) A composition for use in promoting tissue regeneration, comprising a colony-forming PDGFR-positive cell having characteristic i) and characteristics ii) and/or iii) below:

i) having differentiation potency into an osteoblast, an adipocyte and a chondrocyte;
  ii) having differentiation potency into an epidermal cell;
  iii) being P0 lineage-positive.

x) The composition according to claim*, for use in promoting regeneration of a tissue derived from mesoderm or ectoderm.

y) A method for screening for a multipotent stem cell inducer, comprising the steps of:
  1) collecting peripheral blood from a subject, and counting a cell having one or more characteristics selected from $P\alpha^+$, $P\alpha^{lin+}$, $P0^{lin+}$, $Prx1^{lin-}$, $Sox1^{lin-}$, $LepR^{lin-}$, $CD34^+$, and $Sca1^-$ contained in the peripheral blood;
  2) collecting peripheral blood from a subject to which a test substance has been administered, and counting a cell having one or more characteristics selected from $P\alpha^+$, $P\alpha^{lin+}$, $P0^{lin+}$, $Prx1^{lin-}$, $Sox1^{lin-}$, $LepR^{lin-}$, $CD34^+$, and $Sca1^-$ contained in the peripheral blood; and
  3) selecting the test substance as a candidate for a substance having multipotent stem cell-inducing activity when the number of cells counted in step 2) is larger than the number of cells counted in step 1).

z) A method for screening for a multipotent stem cell inducer, comprising the steps of:
  1) counting a cell having one or more characteristics selected from $P\alpha^+$, $P\alpha^{lin+}$, $P0^{lin+}$, $Prx1^{lin-}$, $Sox1^{lin-}$, $LepR^{lin-}$, $CD34^+$, and $Sca1^-$ contained in peripheral blood collected from a subject;
  2) counting a cell having one or more characteristics selected from $P\alpha^+$, $P\alpha^{lin+}$, $P0^{lin+}$, $Prx1^{lin-}$, $Sox1^{lin-}$, $LepR^{lin-}$, $CD34^+$, and $Sca1^-$ contained in peripheral blood collected from a subject to which a test substance has been administered; and
  3) selecting the test substance as a candidate for a substance having multipotent stem cell-inducing activity when the number of cells counted in step 2) is larger than the number of cells counted in step 1).

aa) A method for screening for a multipotent stem cell inducer, comprising the steps of:
  1) collecting peripheral blood from a subject, and culturing the peripheral blood on a solid phase to obtain an adhesive cell population;
  2) performing an exhaustive gene expression analysis on the cell population obtained in step 1 on a colony or single-cell basis;
  3) administering a peptide consisting of an amino acid sequence of SEQ ID NO: 1 (HA1-44 peptide) to a subject, collecting peripheral blood, and culturing the peripheral blood on a solid phase to obtain an adhesive cell population;
  4) performing an exhaustive gene expression analysis on the cell population obtained in step 3 on a colony or single-cell basis;
  5) administering a test substance to a subject, collecting peripheral blood, and culturing the peripheral blood on a solid phase to obtain an adhesive cell population;
  6) performing an exhaustive gene expression analysis on the cell population obtained in step 5 on a colony or single-cell basis;
  7) pooling gene expression data obtained in steps 2 and 4, and performing a clustering analysis;
  8) pooling gene expression data obtained in steps 2 and 6, and performing a clustering analysis; and
  9) comparing an analysis result of step 7 to an analysis result of step 8, and selecting the test substance as a candidate for a substance having multipotent stem cell-inducing activity when the cell population obtained in step 5 (test substance administration group) has the same cluster configuration as the cell population obtained in step 3 (HA1-44 peptide administration group).

ab) The method according to item aa), wherein the test substance is administered in place of the HA1-44 peptide in step 3 and the HA1-44 peptide is administered in place of the test substance in step 5.

ac) The method according to item aa) or ab), wherein the exhaustive gene expression analysis is RNA sequencing (RNA-seq).

ad) The method according to any one of items aa) to ac), wherein clustering analysis is performed using an iterative clustering and guide-gene selection (ICGS) algorithm.

ae) A method for screening for a multipotent stem cell inducer, comprising the steps of:
1) culturing peripheral blood collected from a subject on a solid phase to obtain an adhesive cell population;
2) performing an exhaustive gene expression analysis on the cell population obtained in step 1) on a colony or single-cell basis;
3) culturing peripheral blood collected from a subject to which a peptide consisting of an amino acid sequence of SEQ ID NO: 1 (HA1-44 peptide) has been administered on a solid phase to obtain an adhesive cell population;
4) performing an exhaustive gene expression analysis on the cell population obtained in step 3) on a colony or single-cell basis;
5) culturing peripheral blood collected from a subject to which a test substance has been administered on a solid phase to obtain an adhesive cell population;
6) performing an exhaustive gene expression analysis on the cell population obtained in step 5) on a colony or single-cell basis;
7) pooling gene expression data obtained in steps 2) and 4), and performing a clustering analysis;
8) pooling gene expression data obtained in steps 2) and 6), and performing a clustering analysis; and
9) comparing an analysis result of step 7) to an analysis result of step 8), and selecting the test substance as a candidate for a substance having multipotent stem cell-inducing activity when the cell population obtained in step 5) has the same cluster configuration as the cell population obtained in step 3).

af) A method for screening for a multipotent stem cell inducer, comprising the steps of:
1) collecting peripheral blood from a subject, and culturing the peripheral blood on a solid phase to obtain an adhesive cell population;
2) counting the number of colonies obtained in step 1);
3) administering a test substance to a subject, collecting peripheral blood, and culturing the peripheral blood on a solid phase to obtain an adhesive cell population;
4) counting the number of colonies obtained in step 3); and
5) selecting the test substance as a candidate for a substance having multipotent stem cell-inducing activity when the number of colonies counted in step 4) is larger than the number of colonies counted in step 2).

ag) A method for screening for a multipotent stem cell inducer, comprising the steps of:
1) culturing peripheral blood collected from a subject on a solid phase to obtain an adhesive cell population;
2) counting the number of colonies obtained in step 1);
3) culturing peripheral blood collected from a subject to which a test substance has been administered on a solid phase to obtain an adhesive cell population;
4) counting the number of colonies obtained in step 3); and
5) selecting the test substance as a candidate for a substance having multipotent stem cell-inducing activity when the number of colonies counted in step 4) is larger than the number of colonies counted in step 2).

ah) The screening method according to item ae) or af), wherein the colony counted in steps 2) and 4) is a colony having one or more characteristics selected from $P\alpha^+$, $P\alpha^{lin+}$, $P0^{lin+}$, $Prx1^{lin-}$, $Sox1^{lin-}$, $LepR^{lin-}$, $CD34^+$, and $Sca1^-$.

ai) A method for screening for a multipotent stem cell inducer, comprising the steps of:
1) collecting a bone marrow from a vertebra of a subject, and obtaining a PDGFRα-positive cell population by culturing on a solid phase or cell-sorting;
2) performing an exhaustive gene expression analysis on the cell population obtained in step 1 on a colony or single-cell basis;
3) administering a test substance to a subject, collecting a bone marrow from vertebra, and obtaining a PDGFRα-positive cell population by culturing on a solid phase or cell-sorting;
4) performing an exhaustive gene expression analysis on the cell population obtained in step 3 on a colony or single-cell basis;
5) pooling gene expression data obtained in steps 2 and 4, and performing a pathway analysis; and
6) selecting the test substance as a candidate for a substance having multipotent stem cell-inducing activity when, as a result of the analysis of step 5, (i) a pathway associated with EIF2 signaling, regulation of eIF4 and p70S6K signaling, and/or mTOR signaling is activated or (ii) expression of a cell death-related gene is suppressed, in the cell population obtained in step 3 (test substance administration group) compared to the cell population obtained in step 1 (untreated group).

aj) A method for screening for a multipotent stem cell inducer, comprising the steps of:
1) obtaining a PDGFRα-positive cell population by culturing on a solid phase or cell-sorting from a bone marrow collected from a vertebra of a subject;
2) performing an exhaustive gene expression analysis on the cell population obtained in step 1) on a colony or single-cell basis;
3) obtaining a PDGFRα-positive cell population by culturing on a solid phase or cell-sorting from a bone marrow collected from a vertebra of a subject to which a test substance has been administered;
4) performing an exhaustive gene expression analysis on the cell population obtained in step 3) on a colony or single-cell basis;
5) pooling gene expression data obtained in steps 2) and 4), and performing a pathway analysis; and
6) selecting the test substance as a candidate for a substance having multipotent stem cell-inducing activity when, as a result of the analysis of step 5), (i) a pathway associated with EIF2 signaling, regulation of eIF4 and p70S6K signaling, and/or mTOR signaling is activated or (ii) expression of a cell death-related gene is suppressed, in the cell population obtained in step 3) compared to the cell population obtained in step 1).

ak) The method according to item ai) or aj), wherein the exhaustive gene expression analysis is RNA sequencing (RNA-seq).

al) A method for determining a tissue regeneration-promoting effect of an MSC in-blood-mobilizing substance, comprising the steps of:
1) counting a cell having one or more characteristics selected from P$\alpha^+$, P$\alpha^{lin+}$, P0$^{lin+}$, Prx1$^{lin-}$, Sox1$^{lin-}$, LepR$^{lin-}$, CD34$^+$, and Sca1$^-$ contained in peripheral blood collected from a subject before administering an MSC in-blood-mobilizing substance; and
2) counting a cell having one or more characteristics selected from P$\alpha^+$, P$\alpha^{lin+}$, P0$^{lin+}$, Prx1$^{lin-}$, Sox1$^{lin-}$, LepR$^{lin-}$, CD34$^+$, and Sca1$^-$ contained in peripheral blood collected from the subject after administering an MSC in-blood-mobilizing substance,
wherein tissue regeneration is suggested to be promoted in the subject when the number of cells counted in step 2) is larger than the number of cells counted in step 1).

Advantageous Effects of Invention

According to the present invention, an ectomesenchymal stem cell and a method for producing the same can be provided. Furthermore, a method for screening for a multipotent stem cell inducer can be provided.

BRIEF DESCRIPTION OF DRAWINGS

FIG. 27 is (a) a diagram showing a schematic of the parabiosis model, and (b) photographs showing the tissue observation results of the knee cartilage injury site in the control group (saline administration) and the HA1-44 peptide administration group. Cells of P0$^{lin+}$ were detected with fluorescence of reporter protein tdTomato.

FIG. 29 is a diagram showing the results of performing transcriptome analysis on cells obtained by culturing peripheral blood of mice and performing clustering analysis, on a colony basis. The cell types shown on the left are predicted cell types based on gene expression profiles (such as high expression of a particular gene set). One column corresponds to one colony. Squares were displayed under columns corresponding to colonies derived from mice in the HA1-44 peptide administration group.

FIG. 30 is a table simplifying clustering analysis results of colonies derived from mouse peripheral blood.

DESCRIPTION OF EMBODIMENTS

Figure 1:
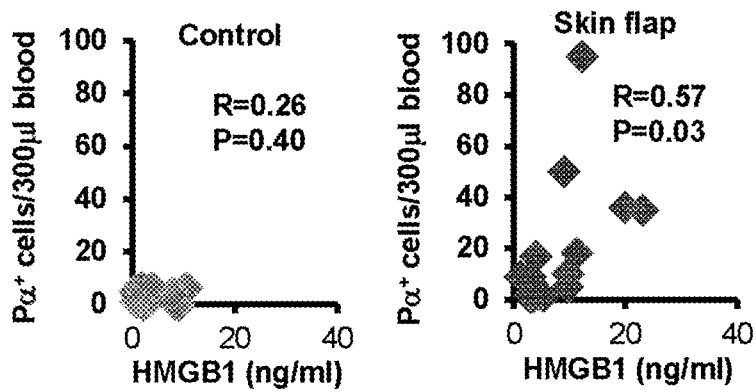
FIG. 1 is a diagram plotting the number of P$\alpha$ cells in peripheral blood and HMGB1 concentration for each of the skin flap-created mouse and the skin flap-not created mouse.

As used herein, the "cell" means one cell or plural cells depending on the context. For example, a cell in the present application may be a cell population consisting of one type of cell or a cell population containing plural types of cells. For example, the expression "cells having differentiation potency into an osteoblast, an adipocyte and a chondrocyte" includes not only a case where one cell/one type of cell (or a homogeneous cell population derived from the cell) has differentiation potency into these three cell types, but also a case where a cell population containing plural cells exerts differentiation potency into the three cell types as a whole cell population.

In the present application, an ectomesenchymal stem cell (EMSC) means a PDGFR-positive cell having colony-forming ability and differentiation potency into mesenchymal three lineages (osteoblasts, adipocytes, chondrocytes) and being suggested to be an ectoderm-derived cell. The cell is suggested to be an ectoderm-derived cell, when, for example, the cell is P0$^{lin+}$. In one aspect, EMSC has also differentiation potency into an epidermal cell (specifically, K5-positive keratinocyte). Examples of the epidermal cells into which EMSC can differentiate include, but are not limited to, keratinocytes, cells expressing keratin 5 (K5) (K5-positive cells), and keratinocytes expressing K5 (K5-positive keratinocytes). For example, whether or not the cell has the differentiation potency into K5-positive keratinocytes can be determined by whether or not the cell can be differentiated into a cell expressing K5 when the cell is cultured under a differentiation-inducing condition into keratinocytes.

Examples of markers (including cell lineage markers) which characterize EMSCs include Pα$^+$, Pα$^{lin+}$, P0$^{lin+}$, Prx1$^{lin-}$, Sox1$^{lin-}$, LepR$^{lin-}$, CD34$^+$, and Sca1$^-$.

Examples of EMSC include:

(a) a colony-forming Pα cell whose amount of presence in peripheral blood increases in response to necrotic tissue injury (such as a skin flap), in other words, a necrotic injury-induced colony-forming Pα cell (hereinafter, the cell is also referred to as "iCFPα cell"); and (b) a colony-forming Pα cell contained in the vertebral bone marrow (hereinafter, the cell is also referred to as a "vertebral CFPα cell" or a "vertebra-derived CFPα cell").

The iCFPα cell has i) colony-forming ability and ii) differentiation potency into osteoblasts, adipocytes and chondrocytes. Thus, it can be said that the iCFPα cell has properties of a mesenchymal stem cell. Furthermore, the iCFPα cell has differentiation potency into an epidermal cell (K5-positive keratinocyte) and is P0$^{lin+}$. Thus, it can be said that the iCFPα cell is an ectomesenchymal stem cell.

Examples of markers that characterize iCFPα cells include Pα$^+$, Pα$^{lin+}$, P0$^{lin+}$, Prx1$^{lin-}$, Sox1$^{lin-}$, LepR$^{lin-}$, CD34$^+$, and Sca1$^-$.

The vertebra-derived CFPα cell has i) colony-forming ability and ii) differentiation potency into osteoblasts, adipocytes and chondrocytes. Thus, it can be said that the vertebra-derived CFPα cell has properties of a mesenchymal stem cell. Furthermore, the vertebra-derived CFPα cell has differentiation potency into an epidermal cell (K5-positive keratinocyte) and is P0$^{lin+}$. Thus, it can be said that the vertebra-derived CFPα cell is an ectomesenchymal stem cell.

Examples of markers that characterize the vertebra-derived CFPα cell include Pα$^+$, P0$^{lin+}$, Prx1$^{lin-}$, and Sox1$^{lin-}$. In addition, the vertebra-derived CFPα cell includes a LepR$^{lin+}$ cell and a LepR$^{lin-}$ cell. Of these, the LepR$^{lin-}$ cell is considered to exhibit properties closer to the iCFPα cell in peripheral blood.

The present application provides, as one aspect of EMSC, a colony-forming PDGFR-positive cell having characteristic i) and characteristics ii) and/or iii) below:
  i) having differentiation potency into an osteoblast, an adipocyte and a chondrocyte;
  ii) having differentiation potency into an epidermal cell;
  iii) being P0 lineage-positive.

In one embodiment, the colony-forming PDGFR-positive cell is a PDGFRα-positive cell. In another embodiment, the colony-forming PDGFR-positive cell is a cell having one or more characteristics selected from Pα$^+$, Pα$^{lin+}$, P0$^{lin+}$, Prx1$^{lin-}$, Sox1$^{lin-}$, LepR$^{lin-}$, CD34$^+$, and Sca1$^-$.

Examples of further characteristics of the colony-forming PDGFR-positive cell include the following:
  being Pα$^+$;
  being CD34$^+$;
  being Sca1$^-$;

being CD34$^+$, and Sca1$^-$;
being CD34$^+$, and having one or more characteristics selected from Pα$^{lin+}$, P0$^{lin+}$, Prx1$^{lin-}$, Sox1$^{lin-}$, and LepR$^{lin-}$;
being Sca1$^-$, and having one or more characteristics selected from Pα$^{lin+}$, Pα$^{lin+}$, Prx1$^{lin-}$, Sox1$^{lin-}$, and LepR$^{lin-}$;
being CD34$^+$, and Sca1$^-$, and having one or more characteristics selected from Pα$^{lin+}$, P0$^{lin+}$, Prx1$^{lin-}$, Sox1$^{lin-}$, and LepR$^{lin-}$;
having one or more characteristics selected from Pα$^{lin+}$, P0$^{lin+}$, Prx1$^{lin-}$, Sox1$^{lin-}$, and LepR$^{lin-}$;
being P0$^{lin+}$, and Prx1$^{lin-}$;
being P0$^{lin+}$, Prx1$^{lin-}$, and Sox1$^{lin-}$;
being P0$^{lin+}$, Prx1$^{lin-}$, and LepR$^{lin-}$;
being P0$^{lin+}$, Prx1$^{lin-}$, Sox1$^{lin-}$, and LepR$^{lin-}$;
being Pα$^{lin+}$, P0$^{lin+}$, and Prx1$^{lin-}$;
being Pα$^{lin+}$, P0$^{lin+}$, Prx1$^{lin-}$, and Sox1$^{lin-}$;
being Pα$^{lin+}$, P0$^{lin+}$, Prx1$^{lin-}$, and LepR$^{lin-}$;
being Pα$^{lin+}$, P0$^{lin+}$, Prx1$^{lin-}$, Sox1$^{lin-}$, and LepR$^{lin-}$;
being Pα$^{lin+}$, P0$^{lin+}$, Prx1$^{lin-}$, Sox1$^{lin-}$, and CD34$^+$;
being Pα$^{lin+}$, P0$^{lin+}$, Prx1$^{lin-}$, Sox1$^{lin-}$, LepR$^{lin-}$, and Sca1$^-$;
being Pα$^{lin+}$, P0$^{lin+}$, Prx1$^{lin-}$, Sox1$^{lin-}$, LepR$^{lin-}$, CD34$^+$, and Sca1$^-$;
being Pα$^+$, and CD34$^+$;
being Pα$^+$, and Sca1$^-$;
being Pα$^+$, CD34$^+$, and Sca1$^-$;
being Pα$^+$, and CD34$^+$, and having one or more characteristics selected from Pα$^{lin+}$, P0$^{lin+}$, Prx1$^{lin-}$, Sox1$^{lin-}$, and LepR$^{lin-}$;
being Pα$^+$, and Sca1$^-$, and having one or more characteristics selected from Pα$^{lin+}$, P0$^{lin+}$, Prx1$^{lin-}$, Sox1$^{lin-}$, and LepR$^{lin-}$;
being Pα$^+$, CD34$^+$, and Sca1$^-$, and having one or more characteristics selected from Pα$^{lin+}$, P0$^{lin+}$, Prx1$^{lin-}$, Sox1$^{lin-}$, and LepR$^{lin-}$;
being Pα$^+$, and having one or more characteristics selected from Pα$^{lin+}$, P0$^{lin+}$, Prx1$^{lin-}$, Sox1$^{lin-}$, and LepR$^{lin-}$;
being Pα$^{lin+}$, P0$^{lin+}$, and Prx1$^{lin-}$;
being Pα$^{lin+}$, P0$^{lin+}$, Prx1$^{lin-}$, and Sox1$^{lin-}$;
being Pα$^{lin+}$, P0$^{lin+}$, Prx1$^{lin-}$, and LepR$^{lin-}$;
being Pα$^{lin+}$, P0$^{lin+}$, Prx1$^{lin-}$, Sox1$^{lin-}$, and LepR$^{lin-}$;
being Pα$^+$, Pα$^{lin+}$, P0$^{lin+}$, and Prx1$^{lin-}$;
being Pα$^+$, Pα$^{lin+}$, P0$^{lin+}$, Prx1$^{lin-}$, and Sox1$^{lin-}$;
being Pα$^+$, Pα$^{lin+}$, P0$^{lin+}$, Prx1$^{lin-}$, and LepR$^{lin-}$;
being Pα$^+$, Pα$^{lin+}$, P0$^{lin+}$, Prx1$^{lin-}$, Sox1$^{lin-}$, and LepR$^{lin-}$;
being Pα$^+$, Pα$^{lin+}$, P0$^{lin+}$, Prx1$^{lin-}$, Sox1$^{lin-}$, LepR$^{lin-}$, and CD34$^+$;
being Pα$^+$, Pα$^{lin+}$, P0$^{lin+}$, Prx1$^{lin-}$, Sox1$^{lin-}$, LepR$^{lin-}$, and Sca1$^-$;
being Pα$^+$, Pα$^{lin+}$, P0$^{lin+}$, Prx1$^{lin-}$, Sox1$^{lin-}$, LepR$^{lin-}$, and CD34$^+$, and Sca1$^-$.

In one embodiment, the present invention relates to a vertebral bone marrow-derived cell that is PDGFRα-positive, CD34-positive, and Sca1-negative. The cell is presumed as a cell equivalent to an iCFPα cell in peripheral blood due to marker commonality. It is thus expected that the vertebral bone marrow-derived cell exhibits properties similar to those of the iCFPα cell. The vertebral bone marrow-derived cell can be obtained, for example, by collecting vertebral bone marrow from a subject and selectively recovering a cell of Pα$^+$, CD34$^+$, and Sca1$^-$.

The present application also provides a bone marrow-derived Pα+CD34$^+$Sca1$^+$ cell. Furthermore, the present application provides a method for producing a cell, comprising a step of selectively recovering a cell of Pα$^+$, CD34$^+$, and Sca1$^+$ from a bone marrow.

Examples of the bone marrow that may be used as a source of Pα$^+$CD34$^+$Sca1$^+$ cells include a bone marrow of vertebra (cervical, thoracic, or lumbar vertebra) and femur. In one aspect, the bone marrow that may be used as a source of Pα$^+$CD34$^+$Sca1$^+$ cells is a bone marrow of vertebra. In another aspect, the bone marrow that may be used as a source of Pα$^+$CD34$^+$Sca1$^+$ cells is a bone marrow of cervical vertebra.

The present inventors have also found that many Pα$^+$CD34$^+$Sca1$^+$ cells are also present in bone marrow of the bone whose embryological origin is ectomesenchyme. Accordingly, the present application provides a Pα$^+$CD34$^+$Sca1$^+$ cell derived from bone marrow of the bone whose embryological origin is ectomesenchyme. The present application also provides a method for producing a cell, comprising a step of selectively recovering a cell of Pα$^+$, CD34$^+$, and Sca1$^+$ from bone marrow of the bone whose embryological origin is ectomesenchyme. Examples of the bone whose embryological origin is ectomesenchyme include frontal skull, nasal bone, zygomatic bone, maxillary bone, palate bone, and mandibular bone.

In one embodiment, the present invention relates to a method for producing a colony-forming PDGFR-positive cell, comprising any one of steps 1) to 4) below:
1) collecting peripheral blood from a subject having a necrotic tissue injury, and culturing the peripheral blood on a solid phase;
2) collecting peripheral blood from a subject having a necrotic tissue injury, and culturing the peripheral blood on a solid phase, and then selectively recovering a cell having one or more characteristics selected from Pα$^+$, Pα$^{lin+}$, P0$^{lin+}$, Prx1$^{lin-}$, Sox1$^{lin-}$, LepR$^{lin-}$, CD34$^+$, and Sca1$^-$;
3) collecting peripheral blood from a subject having a necrotic tissue injury, and selectively recovering a cell having one or more characteristics selected from Pα$^+$, Pα$^{lin+}$, P0$^{lin+}$, Prx1$^{lin-}$, Sox1$^{lin-}$, LepR$^{lin-}$, CD34$^+$, and Sca1$^-$ from the peripheral blood;
4) collecting peripheral blood from a subject having a necrotic tissue injury, selectively recovering a cell having one or more characteristics selected from Pα$^+$, Pα$^{lin+}$, P0$^{lin+}$, Prx1$^{lin-}$, Sox1$^{lin-}$, LepR$^{lin-}$, CD34$^+$, and Sca1$^-$ from the peripheral blood, and culturing the cell on a solid phase.

In one embodiment, the present invention relates to a method for producing a colony-forming PDGFR-positive cell, comprising any one of steps 1) to 4) below:
1) culturing peripheral blood collected from a subject having a necrotic tissue injury on a solid phase;
2) culturing peripheral blood collected from a subject having a necrotic tissue injury on a solid phase, and then selectively recovering a cell having one or more characteristics selected from Pα$^+$, Pα$^{lin+}$, P0$^{lin+}$, Prx1$^{lin-}$, Sox1$^{lin-}$, LepR$^{lin-}$, CD34$^+$, and Sca1$^-$;
3) selectively recovering a cell having one or more characteristics selected from Pα$^+$, Pα$^{lin+}$, P0$^{lin+}$, Prx1$^{lin-}$, Sox1$^{lin-}$, LepR$^{lin-}$, CD34$^+$, and Sca1$^-$ from peripheral blood collected from a subject having a necrotic tissue injury;
4) selectively recovering a cell having one or more characteristics selected from Pα$^+$, Pα$^{lin+}$, P0$^{lin+}$, Prx1$^{lin-}$, Sox1$^{lin-}$, LepR$^{lin-}$, CD34$^+$, and Sca1$^-$ from peripheral blood collected from a subject having a necrotic tissue injury, and culturing the cell on a solid phase.

Examples of the necrotic tissue injury include, but are not limited to, a skin flap, and an epidermis exfoliation in epidermolysis bullosa. In the skin flap, blood supply to the tip part of the flap is insufficient to lead to an ischemic state, resulting in necrosis of the cell/tissue. In epidermolysis bullosa, necrosis occurs in an exfoliated epidermal tissue.

When culturing peripheral blood on a solid phase, red blood cells may be removed from peripheral blood before culturing. Removal of red blood cells may be carried out by a method using a hemolysis reagent known to those skilled in the art, a method for treating peripheral blood with hetastarch and recovering supernatant containing a nuclear cell, or the like.

Examples of the cells to be selectively recovered in step 2), 3) or 4) of the method for producing a colony-forming PDGFR-positive cell include the following:

Cells being $P\alpha^+$
Cells being $CD34^+$
Cells being $Sca1^-$
Cells being $CD34^+$, and $Sca1^-$
Cells being $CD34^+$, and having one or more characteristics selected from $P\alpha^{lin+}$, $P0^{lin+}$, $Prx1^{lin-}$, $Sox1^{lin-}$ and $LepR^{lin-}$
Cells being $Sca1^-$, and having one or more characteristics selected from $P\alpha^{lin+}$, $P0^{lin+}$, $P0^{lin+}$, $Prx1^{lin-}$, $Sox1^{lin-}$ and $LepR^{lin-}$
Cells being $CD34^+$, and $Sca1^-$, and having one or more characteristics selected from $P0^{lin+}$, $P0^{lin+}$, $Prx1^{lin-}$, $Sox1^{lin-}$ and $LepR^{lin-}$
Cells having one or more characteristics selected from $P\alpha^{lin+}$, $P0^{lin+}$, $P0^{lin+}$, $Prx1^{lin-}$, $Sox1^{lin-}$ and $LepR^{lin-}$
Cells being $P0^{lin+}$, and $Prx1^{lin-}$
Cells being $P0^{lin+}$, and $Prx1^{lin-}$, and $Sox1^{lin-}$
Cells being $P0^{lin+}$, and $Prx1^{lin-}$, and $LepR^{lin-}$
Cells being $P0^{lin+}$, $P0^{lin+}$, $Prx1^{lin-}$, $Sox1^{lin-}$ and $LepR^{lin-}$
Cells being $P\alpha^{lin+}$, $P0^{lin+}$, and $Prx1^{lin-}$
Cells being $P\alpha^{lin+}$, $P0^{lin+}$, $Prx1^{lin-}$, and $Sox1^{lin-}$
Cells being $P\alpha^{lin+}$, $P0^{lin+}$, $Prx1^{lin-}$, and $LepR^{lin-}$
Cells being $P\alpha^{lin+}$, $P0^{lin+}$, $P0^{lin+}$, $Prx1^{lin-}$, $Sox1^{lin-}$ and $LepR^{lin-}$
Cells being $P\alpha^{lin+}$, $P0^{lin+}$, $P0^{lin+}$, $Prx1^{lin-}$, $Sox1^{lin-}$ and $LepR^{lin-}$, and $CD34^+$
Cells being $P\alpha^{lin+}$, $P0^{lin+}$, $P0^{lin+}$, $Prx1^{lin-}$, $Sox1^{lin-}$, $LepR^{lin-}$, and $Sca1^-$
Cells being $P\alpha^{lin+}$, $P0^{lin+}$, $P0^{lin+}$, $Prx1^{lin-}$, $Sox1^{lin-}$, $LepR^{lin-}$, $CD34^+$, and $Sca1^-$
Cells being $P\alpha^+$, and $CD34^+$
Cells being $P\alpha^+$, and $Sca1^-$
Cells being $P\alpha^+$, $CD34^+$, and $Sca1^-$
Cells being $P\alpha^+$, and $CD34^+$, and having one or more characteristics selected from $P\alpha^{lin+}$, $P0^{lin+}$, $P0^{lin+}$, $Prx1^{lin-}$, $Sox1^{lin-}$, and $LepR^{lin-}$
Cells being $P\alpha^+$, and $Sca1^-$, and having one or more characteristics selected from $P\alpha^{lin+}$, $P0^{lin+}$, $P0^{lin+}$, $Prx1^{lin-}$, $Sox1^{lin-}$, and $LepR^{lin-}$
Cells being $P\alpha^+$, $CD34^+$, and $Sca1^-$, and having one or more characteristics selected from $P\alpha^{lin+}$, $P0^{lin+}$, $P0^{lin+}$, $Prx1^{lin-}$, $Sox1^{lin-}$, and $LepR^{lin-}$
Cells being $P\alpha^+$, and having one or more characteristics selected from $P\alpha^{lin+}$, $P0^{lin+}$, $Prx1^{lin-}$, $Sox1^{lin-}$, and $LepR^{lin-}$
Cells being $P\alpha^+$, $P0^{lin+}$, and $Prx1^{lin-}$
Cells being $P\alpha^+$, $P0^{lin+}$, $Prx1^{lin-}$, and $Sox1^{lin-}$
Cells being $P\alpha^+$, $P0^{lin+}$, $Prx1^{lin-}$, and $LepR^{lin-}$
Cells being $P\alpha^+$, $P0^{lin+}$, $Prx1^{lin-}$, $Sox1^{lin-}$, and $LepR^{lin-}$
Cells being $P\alpha^+$, $P\alpha^{lin+}$, $P0^{lin+}$, and $Prx1^{lin-}$
Cells being $P\alpha^+$, $P\alpha^{lin+}$, $P0^{lin+}$, $Prx1^{lin-}$, and $Sox1^{lin-}$
Cells being $P\alpha^+$, $P\alpha^{lin+}$, $P0^{lin+}$, $Prx1^{lin-}$, and $LepR^{lin-}$
Cells being $P\alpha^+$, $P\alpha^{lin+}$, $P0^{lin+}$, $Prx1^{lin-}$, $Sox1^{lin-}$, and $LepR^{lin-}$
Cells being $P\alpha^+$, $P\alpha^{lin+}$, $P0^{lin+}$, $Prx1^{lin-}$, $Sox1^{lin-}$, $LepR^{lin-}$, and $CD34^+$
Cells being $P\alpha^+$, $P\alpha^{lin+}$, $P0^{lin+}$, $Prx1^{lin-}$, $Sox1^{lin-}$, $LepR^{lin-}$, and $Sca1^-$
Cells being $P\alpha^+$, $P\alpha^{lin+}$, $P0^{lin+}$, $Prx1^{lin-}$, $Sox1^{lin-}$, $LepR^{lin-}$, $CD34^+$, and $Sca1^-$.

Herein, examples of the method for "selectively recovering" a cell include the following:
(1) a method for "sorting" a cell expressing a desired marker molecule with a cell sorter or the like;
(2) a method of "recovering", "selecting", "separating", "isolating" or "enriching" a cell/colony expressing a desired marker molecule visually or based on a result of gene expression analysis.

Examples of the marker molecule include a surface marker (cell surface antigen) and a reporter protein of a lineage marker gene.

In one embodiment, the present invention relates to a method for producing a colony-forming PDGFR-positive cell, comprising any one of steps 1) to 4) below:
1) collecting a vertebral bone marrow from a subject and culturing the vertebral bone marrow on a solid phase;
2) collecting a vertebral bone marrow from a subject, culturing the vertebral bone marrow on a solid phase, and then selectively recovering a cell having one or more characteristics selected from $P\alpha^+$, $Prx1^{lin-}$, and $Sox1^{lin-}$;
3) collecting a vertebral bone marrow from a subject, and selectively recovering a cell having one or more characteristics selected from $P\alpha^+$, $P0^{lin+}$, $Prx1^{lin-}$, and $Sox1^{lin-}$ from the vertebral bone marrow;
4) collecting a vertebral bone marrow from a subject, selectively recovering a cell having one or more characteristics selected from $P\alpha^+$, $P0^{lin+}$, $Prx1^{lin-}$, and $Sox1^{lin-}$ from the vertebral bone marrow, and culturing the cell on a solid phase.

In one embodiment, the present invention relates to a method for producing a colony-forming PDGFR-positive cell, comprising any one of steps 1) to 4) below:
1) culturing a vertebral bone marrow collected from a subject on a solid phase;
2) culturing a vertebral bone marrow collected from a subject on a solid phase, and then selectively recovering a cell having one or more characteristics selected from $P\alpha^+$, $P0^{lin+}$, $Prx1^{lin-}$, and $Sox1^{lin-}$;
3) selectively recovering a cell having one or more characteristics selected from $P\alpha^+$, $P0^{lin+}$, $Prx1^{lin-}$, and $Sox1^{lin-}$ from a vertebral bone marrow collected from a subject;
4) selectively recovering a cell having one or more characteristics selected from $P\alpha^+$, $P0^{lin+}$, $Prx1^{lin-}$, and $Sox1^{lin-}$ from a vertebral bone marrow collected from a subject, and culturing the cell on a solid phase.

In one embodiment, in step 2), 3), or 4) of the method for producing the colony-forming PDGFR-positive cell, a cell having one or more characteristics selected from $P\alpha^+$, $P0^{lin+}$, $Prx1^{lin-}$, $Sox1^{lin-}$, and $LepR^{lin-}$ may be selectively recovered.

Examples of the cells to be selectively recovered in step 2), 3) or 4) of the method for producing a colony-forming PDGFR-positive cell include the followings:
Cells being $P0^{lin+}$
Cells being $Prx1^{lin-}$
Cells being $Sox1^{lin-}$ Cells being P0$^{lin+}$, and Prx1$^{lin-}$
Cells being P0$^{lin+}$, and Sox1$^{lin-}$
Cells being Prx1$^{lin-}$, and Sox1$^{lin-}$
Cells being P0$^{lin+}$, Prx1$^{lin-}$, and Sox1$^{lin-}$
Cells being Pα$^+$, and P0$^{lin+}$
Cells being Pα$^+$, and Prx1$^{lin-}$
Cells being Pα$^+$, and Sox1$^{lin-}$
Cells being Pα$^+$, P0$^{lin+}$, and Prx1$^{lin-}$
Cells being Pα$^+$, P0$^{lin+}$, and Sox1$^{lin-}$
Cells being Pα$^+$, Prx1$^{lin-}$, and Sox1$^{lin-}$
Cells being Pα$^+$, P0$^{lin+}$, Prx1$^{lin-}$, and Sox1$^{lin-}$
Cells being LepR$^{lin-}$
Cells being P0$^{lin+}$, and LepR$^{lin-}$
Cells being Prx1$^{lin-}$, and LepR$^{lin-}$
Cells being Sox1$^{lin-}$, and LepR$^{lin-}$
Cells being P0$^{lin+}$, Prx1$^{lin-}$, and LepR$^{lin-}$
Cells being P0$^{lin+}$, Sox1$^{lin-}$, and LepR$^{lin-}$
Cells being Prx1$^{lin-}$, Sox1$^{lin-}$, and LepR$^{lin-}$
Cells being P0$^{lin+}$, Prx1$^{lin-}$, Sox1$^{lin-}$, and LepR$^{lin-}$
Cells being Pα$^+$, P0$^{lin+}$, and LepR$^{lin-}$
Cells being Pα$^+$, Prx1$^{lin-}$, and LepR$^{lin-}$
Cells being Pα$^+$, Sox1$^{lin-}$, and LepR$^{lin-}$
Cells being Pα$^+$, P0$^{lin+}$, Prx1$^{lin-}$, and LepR$^{lin-}$
Cells being Pα$^+$, P0$^{lin+}$, Sox1$^{lin-}$, and LepR$^{lin-}$
Cells being Pα$^+$, Prx1$^{lin-}$, Sox1$^{lin-}$, and LepR$^{lin-}$
Cells being Pα$^+$, P0$^{lin+}$, Prx1$^{lin-}$, Sox1$^{lin-}$, and LepR$^{lin-}$.

The vertebra that may be used as a source for colony-forming PDGFR-positive cells include cervical, thoracic, and lumbar vertebrae. In one aspect, the vertebra used as a source for a colony-forming PDGFR-positive cell is cervical vertebra.

In addition, the present inventors have confirmed in experiments conducted so far that colonies obtained by culturing vertebral bone marrow on a solid phase are all PDGFR-positive.

As used herein, the "bone marrow" collected from a subject means a bone marrow tissue containing various bone marrow cells.

In one aspect, the present invention relates to a method for screening for a substance having inducing activity of a multipotent stem cell, using a cell in peripheral blood induced by a necrotic tissue injury as an indicator.

The present inventors have found that iCFPα cells in peripheral blood are increased by a necrotic tissue injury (for example, a skin flap), and that Pα$^+$P0$^{lin+}$Prx1$^{lin-}$ cells (i.e., a cell population containing iCFPα cells) in peripheral blood are increased by administering the HA1-44 peptide. Thus, using increase of iCFPα cells in peripheral blood as an indicator, a substance having an effect of increasing the amount of presence of multipotent stem cells (e.g., MSC) having proliferative ability (colony-forming ability) and multi-lineage differentiation potency in peripheral blood (hereinafter, the substance is also referred to as a multipotent stem cell mobilizing substance, or a multipotent stem cell inducer) can be screened.

In one embodiment, the present invention relates to a method for screening for a multipotent stem cell inducer, comprising the steps of:
1) collecting peripheral blood from a subject, and counting a cell having one or more characteristics selected from Pα$^+$, Pα$^{lin+}$, P0$^{lin+}$, Prx1$^{lin-}$, Sox1$^{lin-}$, LepR$^{lin-}$, CD34$^+$, and Sca1$^-$ contained in the peripheral blood;
2) collecting peripheral blood from a subject to which a test substance has been administered, and counting a cell having one or more characteristics selected from Pα$^+$, Pα$^{lin+}$, P0$^{lin+}$, Prx1$^{lin-}$, Sox1$^{lin-}$, LepR$^{lin-}$, CD34$^+$, and Sca1$^-$ contained in the peripheral blood; and
3) selecting the test substance as a candidate for a substance having multipotent stem cell-inducing activity when the number of cells counted in step 2) is larger than the number of cells counted in step 1).

In one embodiment, the present invention relates to a method for screening for a multipotent stem cell inducer, comprising the steps of:
1) counting a cell having one or more characteristics selected from Pα$^+$, Pα$^{lin+}$, P0$^{lin+}$, Prx1$^{lin-}$, Sox1$^{lin-}$, LepR$^{lin-}$, CD34$^+$, and Sca1$^-$ contained in peripheral blood collected from a subject;
2) counting a cell having one or more characteristics selected from Pα$^+$, Pα$^{lin+}$, P0$^{lin+}$, Prx1$^{lin-}$, Sox1$^{lin-}$, LepR$^{lin-}$, CD34$^+$, and Sca1$^-$ contained in peripheral blood collected from a subject to which a test substance has been administered; and
3) selecting the test substance as a candidate for a substance having multipotent stem cell-inducing activity when the number of cells counted in step 2) is larger than the number of cells counted in step 1).

For the characteristics of the cells to be counted in the screening method described above, surface markers (Pα, CD34, Sca1) can be detected using antibodies or the like. Alternatively, when an experimental animal in which a reporter gene is incorporated downstream of a promoter of the surface marker gene is used, the product of the reporter gene (such as fluorescent protein) can be detected as an indicator. Lineage markers (Pα, P0, Prx1, Sox1, LepR) can be detected by using a transgenic animal having a DNA structure/construct (such as Cre-loxP system) that allows lineage tracing of a gene of interest.

Examples of the cells to be counted in steps 1) and 2) of the screening method described above include the followings:
being Pα$^+$;
being CD34$^+$;
being Sca1$^-$;
being CD34$^+$, and Sca1$^-$;
Cells being and CD34$^+$, and having one or more characteristics selected from Pα$^{lin+}$, P0$^{lin+}$, Prx1$^{lin-}$, Sox1$^{lin-}$, and LepR$^{lin-}$
Cells being Sca1$^-$, and having one or more characteristics selected from Pα$^{lin+}$, P0$^{lin+}$, Prx1$^{lin-}$, Sox1$^{lin-}$, and LepR$^{lin-}$
Cells being CD34$^+$, and Sca1$^-$, and having one or more characteristics selected from Pα$^{lin+}$, P0$^{lin+}$, Prx1$^{lin-}$, Sox1$^{lin-}$, and LepR$^{lin-}$
Cells having one or more characteristics selected from Pα$^{lin+}$, P0$^{lin+}$, Prx1$^{lin-}$, Sox1$^{lin-}$, and LepR$^{lin-}$
Cells being P0$^{lin+}$, and Prx1$^{lin-}$
Cells being P0$^{lin+}$, Prx1$^{lin-}$, and Sox1$^{lin-}$
Cells being P0$^{lin+}$, Prx1$^{lin-}$, and LepR$^{lin-}$
Cells being P0$^{lin+}$, Prx1$^{lin-}$, Sox1$^{lin-}$, and LepR$^{lin-}$
Cells being Pα$^{lin+}$, P0$^{lin+}$, and Prx1$^{lin-}$
Cells being Pα$^{lin+}$, P0$^{lin+}$, Prx1$^{lin-}$, and Sox1$^{lin-}$
Cells being Pα$^{lin+}$, P0$^{lin+}$, Prx1$^{lin-}$, and LepR$^{lin-}$
Cells being Pα$^{lin+}$, P0$^{lin+}$, Prx1$^{lin-}$, Sox1$^{lin-}$, and LepR$^{lin-}$
Cells being Pα$^{lin+}$, P0$^{lin+}$, Prx1$^{lin-}$, Sox1$^{lin-}$, LepR$^{lin-}$, and CD34$^+$
Cells being Pα$^{lin+}$, P0$^{lin+}$, Prx1$^{lin-}$, Sox1$^{lin-}$, LepR$^{lin-}$, and Sca1$^-$
Cells being Pα$^{lin+}$, P0$^{lin+}$, Prx1$^{lin-}$, Sox1$^{lin-}$, LepR$^{lin-}$, CD34$^+$, and Sca1$^-$
Cells being Pα$^+$, and CD34$^+$ Cells being Pα⁺, and Sca1⁻

Cells being Pα⁺, CD34⁺, and Sca1⁻

Cells being Pα⁺, and CD34⁺, and having one or more characteristics selected from Pα$^{lin+}$, P0$^{lin+}$, Prx1$^{lin-}$, Sox1$^{lin-}$, and LepR$^{lin-}$ Cells being Pα⁺, and Sca1⁻, and having one or more characteristics selected from Pα$^{lin+}$, P0$^{lin+}$, Prx1$^{lin-}$, Sox1$^{lin-}$, and LepR$^{lin-}$ Cells being Pα⁺, CD34⁺, and Sca1⁻, and having one or more characteristics selected from Pα$^{lin+}$, P0$^{lin+}$, Prx1$^{lin-}$, Sox1$^{lin-}$, and LepR$^{lin-}$ Cells being Pα⁺, and having one or more characteristics selected from Pα$^{lin+}$, P0$^{lin+}$, Prx1$^{lin-}$, Sox1$^{lin-}$, and LepR$^{lin-}$ Cells being Pα$^{lin+}$, P0$^{lin+}$, and Prx1$^{lin-}$ Cells being Pα$^{lin+}$, P0$^{lin+}$, Prx1$^{lin-}$, and Sox1$^{lin-}$ Cells being Pα$^{lin+}$, P0$^{lin+}$, Prx1$^{lin-}$, and LepR$^{lin-}$ Cells being Pα$^{lin+}$, P0$^{lin+}$, Prx1$^{lin-}$, Sox1$^{lin-}$, and LepR$^{lin-}$ Cells being Pα⁺, Pα$^{lin+}$, P0$^{lin+}$, and Prx1$^{lin-}$ Cells being Pα⁺, Pα$^{lin+}$, P0$^{lin+}$, Prx1$^{lin-}$, and Sox1$^{lin-}$ Cells being Pα⁺, Pα$^{lin+}$, P0$^{lin+}$, Prx1$^{lin-}$, and LepR$^{lin-}$ Cells being Pα⁺, Pα$^{lin+}$, P0$^{lin+}$, Prx1$^{lin-}$, Sox1$^{lin-}$, and LepR$^{lin-}$ Cells being Pα⁺, Pα$^{lin+}$, P0$^{lin+}$, Prx1$^{lin-}$, Sox1$^{lin-}$, LepR$^{lin-}$, and CD34⁺

Cells being Pα⁺, Pα$^{lin+}$, P0$^{lin+}$, Prx1$^{lin-}$, Sox1$^{lin-}$, LepR$^{lin-}$, and Sca1⁻

Cells being Pα⁺, Pα$^{lin+}$, P0$^{lin+}$, Prx1$^{lin-}$, Sox1$^{lin-}$, LepR$^{lin-}$, and CD34⁺, and Sca1⁻.

In one aspect, the present invention relates to a method for screening for a substance having inducing activity of a multipotent stem cell, using the HA1-44 peptide as a positive control, and using the reaction of a multipotent stem cell that contributes to tissue regeneration in vivo as an indicator.

In one embodiment, the present invention relates to a method for screening for a multipotent stem cell inducer, comprising the steps of:

1) collecting peripheral blood from a subject, and culturing the peripheral blood on a solid phase to obtain an adhesive cell population;
2) performing an exhaustive gene expression analysis on the cell population obtained in step 1 on a colony or single-cell basis;
3) administering a peptide consisting of an amino acid sequence of SEQ ID NO: 1 (HA1-44 peptide) to a subject, collecting peripheral blood, and culturing the peripheral blood on a solid phase to obtain an adhesive cell population;
4) performing an exhaustive gene expression analysis on the cell population obtained in step 3 on a colony or single-cell basis;
5) administering a test substance to a subject, collecting peripheral blood, and culturing the peripheral blood on a solid phase to obtain an adhesive cell population;
6) performing an exhaustive gene expression analysis on the cell population obtained in step 5 on a colony or single-cell basis;
7) pooling gene expression data obtained in steps 2 and 4, and performing a clustering analysis;
8) pooling gene expression data obtained in steps 2 and 6, and performing a clustering analysis; and
9) comparing an analysis result of step 7 to an analysis result of step 8, and selecting the test substance as a candidate for a substance having multipotent stem cell-inducing activity when the cell population obtained in step 5 (test substance administration group) has the same cluster configuration as the cell population obtained in step 3 (HA1-44 peptide administration group).

In other embodiments, the test substance is administered in place of the HA1-44 peptide in step 3, and the HA1-44 peptide is administered in place of the test substance in step 5. That is, either the HA1-44 peptide or the test substance may be administered to the subject first. Subjects in steps 1, 3 and 5 may be the same individual or another individual. For example, the method may be performed by preparing three animals of the same strain, and administering no substance (or administering solvent only) to one, administering an HA1-44 peptide to another one, and administering a test substance to the remaining one, and then collecting peripheral blood from each individual to obtain an adhesive cell population, and perform an exhaustive gene expression analysis and a clustering analysis. The subject in step 1 may be a subject to which only the solvent has been administered which is the same as the solvent used in administering the HA1-44 peptide and the test substance in steps 3 and 5, respectively.

In another embodiment, a variant or modified of the HA1-44 peptide or a tagged HA1-44 peptide is used instead of the HA1-44 peptide. The variant has an amino acid sequence in which several, e.g., 1 to 5, preferably 1 to 4, 1 to 3, more preferably 1 to 2, even more preferably 1 amino acid is substituted, inserted, deleted and/or added in the amino acid sequence of the HA1-44 peptide. For example, the variant is a peptide having an amino acid sequence which has a 50% or more, preferably 60% or more, further preferably 70% or more, more preferably 80% or more, more preferably 85% or more, and particularly preferably 90% or more (e.g., 91%, 92%, 93%, 94%, 95%, 96%, 97%, or 98%) homology to the amino acid sequence of the HA1-44 peptide when performing a local alignment. The homology of amino acid sequences can be measured, for example, using FASTA, BLAST, DNASIS (manufactured by Hitachi Software Engineering Co., Ltd.), or GENETYX (manufactured by GENETYX CORPORATION). Alternatively, the sequences can be simply compared and calculated. The modified has an amino acid sequence in which an amino acid residue of several, e.g., 1 to 5, preferably 1 to 4, 1 to 3, further preferably 1 to 2, more preferably 1 amino acid in the amino acid sequence of the HA1-44 peptide is modified. When the tagged HA1-44 peptide is used, examples of the tag include, but are not limited to, an His$_6$-tag, a FLAG tag, an myc tag, and a GST tag. The tag may be added to either the N-terminus or the C-terminus of the amino acid sequence.

In the screening method, the exhaustive gene expression analysis may be RNA sequencing (RNA-seq). In the screening method, clustering analysis may be performed using an iterative clustering and guide-gene selection (ICGS) algorithm.

In another embodiment, the present invention relates to a method for screening for a multipotent stem cell inducer, comprising the steps of:

1) culturing peripheral blood collected from a subject on a solid phase to obtain an adhesive cell population;
2) performing an exhaustive gene expression analysis on the cell population obtained in step 1) on a colony or single-cell basis;
3) culturing peripheral blood collected from a subject to which a peptide consisting of an amino acid sequence of SEQ ID NO: 1 (HA1-44 peptide) has been administered on a solid phase to obtain an adhesive cell population;

4) performing an exhaustive gene expression analysis on the cell population obtained in step 3) on a colony or single-cell basis;
5) culturing peripheral blood collected from a subject to which a test substance has been administered on a solid phase to obtain an adhesive cell population;
6) performing an exhaustive gene expression analysis on the cell population obtained in step 5) on a colony or single-cell basis;
7) pooling gene expression data obtained in steps 2) and 4), and performing a clustering analysis;
8) pooling gene expression data obtained in steps 2) and 6), and performing a clustering analysis; and
9) comparing an analysis result of step 7) to an analysis result of step 8), and selecting the test substance as a candidate for a substance having multipotent stem cell-inducing activity when the cell population obtained in step 5) has the same cluster configuration as the cell population obtained in step 3).

In another embodiment, the present invention relates to a method for screening for a multipotent stem cell inducer, comprising the steps of:
1) collecting peripheral blood from a subject, and culturing the peripheral blood on a solid phase to obtain an adhesive cell population;
2) counting the number of colonies obtained in step 1);
3) administering a test substance to a subject, collecting peripheral blood, and culturing the peripheral blood on a solid phase to obtain an adhesive cell population;
4) counting the number of colonies obtained in step 3); and
5) selecting the test substance as a candidate for a substance having multipotent stem cell-inducing activity when the number of colonies counted in step 4) is larger than the number of colonies counted in step 2).

The subject in step 1) may be a subject to which only the solvent has been administered which is the same as the solvent used in administering the test substance in step 3).

The colony counted in steps 2) and 4) may be a colony having one or more characteristics selected from $P\alpha^+$, $P\alpha^{lin+}$, $P0^{lin+}$, $Prx1^{lin-}$, $Sox1^{lin-}$, $LepR^{lin-}$, $CD34^+$, and $Sca1^-$.

In another embodiment, the present invention relates to a method for screening for a multipotent stem cell inducer, comprising the steps of:
1) culturing peripheral blood collected from a subject on a solid phase to obtain an adhesive cell population;
2) counting the number of colonies obtained in step 1);
3) culturing peripheral blood collected from a subject to which a test substance has been administered on a solid phase to obtain an adhesive cell population;
4) counting the number of colonies obtained in step 3); and
5) selecting the test substance as a candidate for a substance having multipotent stem cell-inducing activity when the number of colonies counted in step 4) is larger than the number of colonies counted in step 2).

The subject in step 1) may be a subject to which only the solvent has been administered which is the same as the solvent used in administering the test substance in step 3).

The colony counted in steps 2) and 4) may be a colony having one or more characteristics selected from $P\alpha^+$, $P\alpha^{lin+}$, $P0^{lin+}$, $Prx1^{lin-}$, $Sox1^{lin-}$, $LepR^{lin-}$, $CD34^+$, and $Sca1^-$.

In another embodiment, the present invention relates to a method for screening for a multipotent stem cell inducer, comprising the steps of:
1) collecting a bone marrow from a vertebra of a subject, and obtaining a PDGFRα-positive cell population by culturing on a solid phase or cell-sorting;
2) performing an exhaustive gene expression analysis on the cell population obtained in step 1 on a colony or single-cell basis;
3) administering a test substance to a subject, collecting a bone marrow from vertebra, and obtaining a PDGFRα-positive cell population by culturing on a solid phase or cell-sorting;
4) performing an exhaustive gene expression analysis on the cell population obtained in step 3 on a colony or single-cell basis;
5) pooling gene expression data obtained in steps 2 and 4, and performing a pathway analysis; and
6) selecting the test substance as a candidate for a substance having multipotent stem cell-inducing activity when, as a result of the analysis of step 5, (i) a pathway associated with EIF2 signaling, regulation of eIF4 and p70S6K signaling, and/or mTOR signaling is activated or (ii) expression of a cell death-related gene is suppressed, in the cell population obtained in step 3 (test substance administration group) compared to the cell population obtained in step 1 (untreated group).

The subject in step 1 may be a subject to which only the solvent has been administered which is the same as the solvent used in administering the test substance in step 3.

In the screening method, the exhaustive gene expression analysis may be RNA sequencing (RNA-seq). In the screening method, the pathway analysis may be performed using an Ingenuity Pathway Analysis (IPA) software (https://www.qiagenbioinformatics.com).

In another embodiment, the present invention relates to a method for screening for a multipotent stem cell inducer, comprising the steps of:
1) obtaining a PDGFRα-positive cell population by culturing on a solid phase or cell-sorting from a bone marrow collected from a vertebra of a subject;
2) performing an exhaustive gene expression analysis on the cell population obtained in step 1) on a colony or single-cell basis;
3) obtaining a PDGFRα-positive cell population by culturing on a solid phase or cell-sorting from a bone marrow collected from a vertebra of a subject to which a test substance has been administered;
4) performing an exhaustive gene expression analysis on the cell population obtained in step 3) on a colony or single-cell basis;
5) pooling gene expression data obtained in steps 2) and 4), and performing a pathway analysis; and
6) selecting the test substance as a candidate for a substance having multipotent stem cell-inducing activity when, as a result of the analysis of step 5), (i) a pathway associated with EIF2 signaling, regulation of eIF4 and p70S6K signaling, and/or mTOR signaling is activated or (ii) expression of a cell death-related gene is suppressed, in the cell population obtained in step 3) compared to the cell population obtained in step 1).

In the screening method, the exhaustive gene expression analysis may be RNA sequencing (RNA-seq). In the screening method, the pathway analysis may be performed using Ingenuity Pathway Analysis (IPA) software (https://www.qiagenbioinformatics.com).

In other aspects, the present invention relates to a cell or cell population in peripheral blood, induced by an MSC in-blood-mobilizing substance. The present invention also relates to a cell or cell population in the vertebral bone marrow induced by the HA1-44 peptide.

As used herein, the "MSC in-blood-mobilizing substance" means a substance having the activity of a mobilizing mesenchymal stem cell (MSC) into peripheral blood or increasing the amount of MSC present in peripheral blood. Examples of the MSC in-blood-mobilizing substance include, but are not limited to, an HMGB1 protein, an HMGB2 protein, and an HMGB3 protein (e.g., those described in WO 2008/053892 and WO 2009/133939), an S100A8 protein and an S100A9 protein (e.g., those described in WO 2009/133940 and WO 2011/052668), and various HMGB1 peptides (e.g., a peptide consisting of amino acid residues 1-44 of the HMGB1 protein (the HA1-44 peptide in the present application)) described in International Application WO 2012/147470 by the present inventors.

In one embodiment, the present invention relates to a cell population obtained by administering an MSC in-blood-mobilizing substance to a subject, collecting peripheral blood from the subject, and culturing the collected peripheral blood on a solid phase. In one embodiment, the MSC in-blood-mobilizing substance may be an HA1-44 peptide.

In other embodiments, the present invention relates to a cell population obtained by 1) administering an HA1-44 peptide to a subject, 2) collecting a vertebral bone marrow from the subject, and 3) culturing the collected bone marrow on a solid phase, or sorting a PDGFRα-positive cell from the collected bone marrow.

In another aspect, the present invention relates to a method for producing the cell or cell population described above.

In one embodiment, the present invention relates to a method for producing a cell, comprising a step of administering an MSC in-blood-mobilizing substance to a subject, collecting peripheral blood from the subject, and culturing the collected peripheral blood on a solid phase. In other embodiments, the present invention relates to a method for producing a cell, comprising a step of culturing peripheral blood collected from a subject to which an MSC in-blood-mobilizing substance has been administered on a solid phase. In one embodiment of these production methods, the MSC in-blood-mobilizing substance may be an HA1-44 peptide.

In other embodiments, the present invention relates to a method for producing a cell, comprising the steps of 1) administering an HA1-44 peptide to a subject, 2) collecting a vertebral bone marrow from the subject, and 3) culturing the collected bone marrow on a solid phase, or sorting a PDGFRα-positive cell from the collected bone marrow.

In yet another aspect, the present invention relates to a method for obtaining, isolating, and/or enriching a cell having a high tissue regeneration promoting ability similar to a PDGFRα-positive cell in a vertebral bone marrow from a biological tissue containing a mesenchymal stem cell (MSC). In yet another aspect, the present invention relates to a cell or cell population obtained by the method for obtaining, isolating and/or enriching described above.

In one embodiment, the present invention relates to a method for producing a cell population, comprising the steps of:
1) culturing a cell population from a biological tissue containing a mesenchymal stem cell (MSC) on a solid phase;
2) subcloning a colony obtained in step 1);
3) culturing a portion of cells obtained by the subcloning in a differentiation-inducing medium into bone, cartilage, and/or fat, and measuring an expression level of a differentiation marker of bone, cartilage, and/or fat; and
4) selecting a cell clone showing a high expression level compared to the expression level of a differentiation marker of bone, cartilage, and/or fat in case that MSC obtained by culturing a femur bone marrow on a solid phase are cultured in a differentiation-inducing medium into bone, cartilage, and/or fat.

In other embodiments, the present invention relates to a method for producing a cell population, comprising the steps of:
1) culturing a cell population derived from a biological tissue containing MSC on a solid phase; and
2) selecting a colony having one or more characteristics selected from P$\alpha^+$, P$\alpha^{lin+}$, P0$^{lin+}$, Prx1$^{lin-}$, Sox1$^{lin-}$, LepR$^{lin-}$, CD34$^+$, and Sca1$^-$. In one embodiment, step 2 may be a step of selecting a Prx1 lineage-negative colony.

In another embodiment, the present invention relates to a method for producing a cell population, comprising a step of selectively recovering a cell having one or more characteristics selected from P$\alpha^+$, P$\alpha^{lin+}$, P0$^{lin+}$, Prx1$^{lin-}$, Sox1$^{lin-}$, LepR$^{lin-}$, CD34$^+$, and Sca1$^-$, from a cell population derived from a biological tissue containing MSC.

In other embodiments, the present invention relates to a method for producing a cell population, comprising the steps of:
1) selectively recovering a cell having one or more characteristics selected from P$\alpha^+$, P$\alpha^{lin+}$, P0$^{lin+}$, Prx1$^{lin-}$, Sox1$^{lin-}$, LepR$^{lin-}$, CD34$^+$, and Sca1$^-$, from a cell population derived from a biological tissue containing MSC; and
2) culturing the cell recovered in step 1) on a solid phase.

In the method for producing a cell population of the present application, the biological tissue containing MSC includes, but are not limited to, bone marrow, umbilical cord, umbilical cord blood, placenta, adipose tissue, dental cord, periosteum, synovial membrane, ovary membrane, and peripheral blood. Examples of the bone marrow includes, but are not limited to, bone marrows of femur, vertebra, sternum, ilium, and skull.

In yet another aspect, the present invention relates to a composition for use in promoting tissue regeneration, containing an ectomesenchymal stem cell. In one embodiment, the present invention relates to a composition for use in promoting tissue regeneration, containing a colony-forming PDGFR-positive cell having characteristic i) and characteristics ii) and/or iii) below:
i) having differentiation potency into an osteoblast, an adipocyte and a chondrocyte;
ii) having differentiation potency into an epidermal cell;
iii) being P0 lineage-positive.

In one embodiment, the composition is a composition for use in promoting regeneration of a tissue derived from mesoderm or ectoderm. Examples of the tissue derived from mesoderm include, but are not limited to, bone, cartilage, muscle, and vascular endothelium. Examples of the tissue derived from ectoderm include, but are not limited to, an epithelial tissue (e.g., epidermis), and a neural tissue.

The composition for use in promoting tissue regeneration of the present invention may contain a pharmaceutically acceptable carrier, a diluent and/or an excipient. In the composition for use in promoting tissue regeneration of the present invention, the amount of ectomesenchymal stem cells contained, the dosage form of the composition, the frequency of administration, or the like can be appropriately selected depending on the condition such as the type of tissue to be regenerated and/or the condition of the subject to be administered.

In yet another aspect, the present invention relates to a method for promoting tissue regeneration in a subject, comprising administering an ectomesenchymal stem cell. In one embodiment, the present invention relates to a method for promoting tissue regeneration in a subject, comprising administering to the subject a colony-forming PDGFR-positive cell having characteristic i) and characteristics ii) and/or iii) below:
  i) having differentiation potency into an osteoblast, an adipocyte and a chondrocyte;
  ii) having differentiation potency into an epidermal cell;
  iii) being P0 lineage-positive.

The method for administering the cell can be appropriately selected depending on the condition such as the type of tissue to have regeneration promotion and/or the condition of the subject to be administered. Examples of the method for administering the cell include, but are not limited to, intradermal administration, subcutaneous administration, intramuscular administration, intravenous administration, nasal administration, oral administration, and suppositories.

In yet another aspect, the present invention relates to an ectomesenchymal stem cell for use in promoting tissue regeneration in a subject.

In yet another aspect, the present invention relates to a use of an ectomesenchymal stem cell for the manufacture of a medicament for promoting tissue regeneration in a subject.

It is believed that iCFPα cells in peripheral blood can be beneficial biomarkers for assessing EMSC-mediated tissue regenerative activity, in cases where necrotic tissue injury is generated. Accordingly, the present application provides a method for determining an expected tissue regeneration promoting effect in a subject to which an MSC in-blood-mobilizing substance has been administered, using an iCFPα cell in peripheral blood as an indicator.

In one embodiment, the present invention relates to a method for determining a tissue regeneration-promoting effect of an MSC in-blood-mobilizing substance, comprising the steps of:
  1) counting a cell having one or more characteristics selected from P$\alpha^+$, P$\alpha^{lin+}$, P0$^{lin+}$, Prx1$^{lin-}$, Sox1$^{lin-}$, LepR$^{lin-}$, CD34$^+$, and Sca1$^-$ contained in peripheral blood collected from a subject before administering an MSC in-blood-mobilizing substance; and
  2) counting a cell having one or more characteristics selected from P$\alpha^+$, P$\alpha^{lin+}$, P0$^{lin+}$, Prx1$^{lin-}$, Sox1$^{lin-}$, LepR$^{lin-}$, CD34$^+$, and Sca1$^-$ contained in peripheral blood collected from the subject after administering an MSC in-blood-mobilizing substance,
  wherein tissue regeneration is suggested to be promoted in the subject when the number of cells counted in step 2) is larger than the number of cells counted in step 1).

In the present application, the "subject" may be either a human or a non-human animal. In one aspect, the subject is a non-human animal. Examples of the non-human animal include, but are not limited to, mouse, rat, monkey, pig, dog, rabbit, hamster, guinea pig, horse, and sheep.

The timing of collecting peripheral blood from a subject is not particularly limited with respect to a method for producing a cell (or cell population), a method for screening, and a method for determining a tissue regeneration promoting effect of an MSC in-blood-mobilizing substance, provided by the present application. When artificially creating a necrotic tissue injury or administering an MSC in-blood-mobilizing substance, a method in which peripheral blood is collected, for example, 2 to 24 hours after creating the necrotic tissue injury or administering the MSC in-blood-mobilizing substance can be included. In one aspect, the timing of collecting peripheral blood from the subject may be 2, 3, 4, 5, 6, 7, 8, 9, 10, 11, 12, 13, 14, 15, 16, 17, 18, 19, 20, 21, 22, 23, or 24 hours after creating the necrotic tissue injury or administering the MSC in-blood-mobilizing substance. In another aspect, the timing of collecting peripheral blood from the subject may be 4 to 24 hours, 8 to 24 hours, 8 to 16 hours, or 10 to 14 hours after creating the necrotic tissue injury or administering the MSC in-blood-mobilizing substance.

In one aspect of the cell, the method for producing a cell (or cell population), the composition comprising the cell, and the screening methods provided herein, the PDGFR-positive cell is a PDGFRα-positive cell.

It should be noted that all the prior art literature cited herein is incorporated herein by reference. This application also claims priority based on U.S. Provisional Patent Application No. 62/593,310, filed on Dec. 1, 2017 to the United States Patent and Trademark Office, the contents of which are incorporated herein by reference.

Hereinafter, the present invention will be described in further detail. Note that the present invention is described in further detail below, but the present invention is not limited to the aspects described below.

EXAMPLES

Materials and Methods

1. Mouse

Pα-H2B-GFP mice capable of confirming PDGFRα expression with GFP fluorescence (The Jackson Laboratory, Stock No: 007669) and various cell lineage tracing mice utilizing the Cre-loxP system were used for experiments.

The cell lineage tracing mice utilizing the Cre-loxP system can be made by crossing a Cre driver mouse with a Cre reporter mouse. The Cre driver mouse is a transgenic mouse having a DNA structure in which a coding sequence of Cre recombinase is introduced downstream of a promoter sequence of a desired gene. The Cre reporter mouse is a transgenic mouse into which a DNA sequence having the structure "promoter (such as a CAG promoter)-loxP-stop cassette-loxP-desired reporter gene (EYFP or tdTomato in the Examples of the present application)" is introduced at a locus such as ROSA26.

In the Examples herein, the following mice were prepared as Cre driver mice.
  Pα-Cre mouse (The Jackson Laboratory, Stock No: 013148)
  P0-Cre mouse (The Jackson Laboratory, Stock No: 017927)
  Prx1-Cre mouse (The Jackson Laboratory, Stock No: 005584)
  Sox1-Cre mouse (RIKEN BioResource Research Center, Accession No. CDB0525K)
  LepR-Cre mouse (The Jackson Laboratory, Stock No: 008320)
  Krt5-Cre mouse (MGI ID: 1926815, K5 Cre transgenic mouse described in Proc Natl Acad Sci USA. 1997 Jul. 8; 94(14):7400-5)

The following mice were prepared as Cre reporter mice.
  Rosa26-EYFP mouse (The Jackson Laboratory, Stock No: 006148)
  Rosa26-tdTomato mouse (The Jackson Laboratory, Stock No: 007909)

The following cell lineage tracing mice were generated by crossing the six driver mice described each with the Rosa26-tdTomato reporter mouse.

Pα-Cre::Rosa26-tdTomato mouse
P0-Cre::Rosa26-tdTomato mouse
Prx1-Cre::Rosa26-tdTomato mouse
Sox1-Cre::Rosa26-tdTomato mouse
LepR-Cre::Rosa26-tdTomato mouse
Krt5-Cre::Rosa26-tdTomato mouse Furthermore, Pα-Cre::Rosa26-EYFP mouse was also generated by crossing the Pα-Cre driver mouse with the Rosa26-EYFP reporter mouse.

Pα-H2B-GFP mouse is a mouse in which a sequence encoding a fusion protein of histone H2B and eGFP has been knocked in downstream of a promoter of the PDGFRα gene. The Pα-H2B-GFP mouse was crossed with the Prx1-Cre::Rosa26-tdTomato mouse to produce Pα-H2B-GFP::Prx1-Cre::Rosa26-tdTomato mouse.

2. Creation of Skin Flap

In the examples of the present application, a skin flap was created as a method for causing a necrotic tissue injury. Specifically, the method for creating the skin flap was as follows.

Male mice (20-25 g) of 8-10 week old were shaved on the back under 1.5-2.0% (v/v) isoflurane inhalation anesthesia. A skin flap of 2.0 cm wide×4.0 cm long across the center of the back was created with a razor so that the skin continuity was maintained only on the tail side (which led to an ischemic state of the tip part away from the root of the flap, resulting in causing a necrotic injury to skin tissue). The affected area after the skin flap creation was protected with a bandage of sufficient size. Cardiac blood collection, separation of vertebra and femoral bone marrow cells, and creation of frozen sections of vertebra and femur were performed 12 hours after the skin flap creation for each.

3. Creation of Parabiosis

A parabiosis model was created using a 6-week old male wild-type mouse and a 6-week old male cell lineage tracing mouse with reference to Kamran P et al. J Vis Exp. 2013 Oct. 6; (80). Two mice were simultaneously subjected to general anesthetic induction with isoflurane, and positioned on a heat pad. The body side surfaces opposite to each other of the two mice were shaved, and the skin was removed approximately 5 mm wide from the elbow joint to the knee joint. The dorsal skin was continuously sutured with 5-0 VICRYL. The elbow joints and knee joints each opposite to each other were sutured with 3-0 VICRYL. The abdominal skin was also continuously sutured with 5-0 VICRYL. The mice were left on the heat pad until awakened from anesthesia. To avoid restricting activity, up to one pair were raised per cage, and scattered food was offered.

4. Tissue Staining and Observation

After vertebral and femoral bones were collected, fixation with 4% paraformaldehyde, deashing with 0.5 M EDTA solution, and replacement with 30% sucrose solution were performed, then a frozen block was created using a frozen embedding agent for Kawamoto method, Super Cryoembedding Medium (SCEM) (Leica). The block was sliced with Cryofilm type 2C(9) (Leica) at a thickness of 10 μm, and immunostaining was performed with each antibody (with a primary antibody at 4° C. overnight, and with a secondary antibody at 4° C. for 1 hour). Confocal microscopy was used for tissue observation.

5. Acquisition and Culture of Cells in Peripheral Blood, Vertebra and Femur

The following method was used to recover cells from peripheral blood. Approximately 800 to 1000 μL of peripheral blood was collected from the heart under general anesthesia (using a 1 mL syringe containing heparin). To remove red blood cells, Hetasep (STEMCELL Technologies, Inc., Cat No. ST-07906) at equal amount of the collected blood was added, the mixture was centrifuged at 100 G for 2 minutes, and incubated at room temperature for 15 minutes, then the supernatant was recovered. The supernatant was subjected to the next experiment as a sample containing nuclear cells in peripheral blood.

The following method was used to recover cells from bone marrow. The vertebrae and femur collected under general anesthesia were immersed in 0.2% Collagenase A solution (Sigma-Aldrich Corp., Cat #10103578001) and incubated at 37° C. for 1 hour. Bone marrow cells were extruded in a breast bowl, recovered by pipetting and passed through a 40 μm cell strainer. The supernatant was centrifuged at 300 G for 5 minutes for removal, and hemolyzed with RBC Lysis buffer (BioLegend, Inc., cat #420301) to remove red blood cells, then the resultant was subjected to the following experiments as bone marrow cells.

6. Colony Assay of Peripheral Blood

The supernatant obtained by the above procedure (sample containing nucleated cells in peripheral blood) was seeded in a 6-well plate coated with collagen I (Corning Incorporated, Cat No. 356400), and cultured for 10 days under a condition of 37° C., 5% CO2, 5% O2 using a medium containing 1% L-glutamine (NACALAI TESQUE, INC.), 10 μM ROCK inhibitor (Y27632, Tocris Bioscience) and 1% penicillin/streptomycin (NACALAI TESQUE, INC.) in an expansion medium prepared using a MesenCult Expansion Kit (STEMCELL Technologies, Inc., Cat No. ST-05513) according to the manual of the kit (all concentrations described are final concentrations). The medium was replaced with a fresh medium twice a week during the culture period. On day 10 of the culture, cells on plates were stained with a Differential Quik Stain Kit (Sysmex Corporation, Cat No. 16920), and the number of colonies containing not fewer than 50 cells was counted.

7. Differentiation Induction Into Osteoblast/Adipocyte/Chondrocyte

Viable cells of passages 3-5 were seeded in a 12-well plate at 50,000 cells/well, and cultured with 10% FBS/DMEM until subconfluency. Subsequently, fat differentiation induction was performed for 14 days using 10% FBS/DMEM containing 100 nM dexamethasone (Sigma-Aldrich Corp.), 0.5 mM isobutylmethylxanthine (Sigma-Aldrich Corp.), 50 mM indomethacin (Wako Pure Chemical Industries, Ltd.) and 10 μg/ml insulin (Sigma-Aldrich Corp.) for differentiation into adipocytes.

Osteoblast differentiation induction was performed for 21 days using 10% FBS/DMEM including 1 nM dexamethasone, 20 mM β-glycerol phosphate (Wako Pure Chemical Industries, Ltd.) and 50 μg/ml ascorbate-2-phosphate (Sigma-Aldrich Corp.) for differentiation into osteoblasts. After each differentiation induction, fixation with 4% PFA was performed, then adipocytes were stained with oil red-0 and osteoblasts were ALP stained with an ALP activity assay kit (TAKARA BIO Inc., Kusatsu, Japan), and observed with microscope.

In cartilage differentiation induction, 300,000 cells were first centrifuged in a 15 ml tube at 300 g, for 5 minutes. Cartilage differentiation induction was performed for 21 days using 10% FBS/DMEM containing 40 ng/ml proline (Sigma-Aldrich Corp.), 50 μg/ml ascorbic acid 2-phosphate, ×100 ITS mix (BD Biosciences), 2 μg/ml fluocinolone (Tokyo Chemical Industry Co., Ltd., Tokyo, Japan), 5 ng/ml transforming growth factor-b3 (R&D Systems, Minneapolis, MN), and 100 nM dexamethasone (Sigma-Aldrich Corp.). The completed chondropellets were paraffin-embedded, thinly sliced at a thickness of 6 μm, and stained with toluidine blue.

8. Differentiation Induction into Keratinocytes

—Animal

Krt5-Cre::Rosa26-tdTomato mice were raised until they were 8-10 weeks old, and used for experiments.

—Collection of Materials

A skin flap was created on the back of the mouse the day before the collection of materials, and 12 hours after the creation, peripheral blood was collected by cardiac blood collection under anesthesia. Peripheral blood was also collected in the same way from the mouse in which no skin flap was created. Femurs and vertebra were collected after blood collection.

—Cell Conditioning

Red blood cells were removed from the peripheral blood with HetaSep, and one portion of blood corresponding to one mouse was seeded into one well of a 6-well plate coated with collagen I and cultured under a condition of 5% $O_2$, 5% $CO_2$, and 37° C. The medium used was MesenCult or 20% FBS/MEMα (both containing Rock inhibitor and 1% Penicillin-Streptomycin).

After both bone ends were cut out, the collected femur was divided into longitudinal halves. The collected vertebra was divided into longitudinal halves. Both were then treated with 0.2% Collagenase A/DMEM (10 mM HEPES, 1% Penicillin-Streptomycin) (37° C. water bath, for 1 hour). After Collagenase A treatment, the bone marrow cells were recovered in a breast bowl, dispersed into single cells with 40 um cell strainer, hemolytized with 1×RBC Lysis solution, then seeded, and cultured under a condition of 5% $O_2$, 5% $CO_2$, and 37° C. The medium used was MesenCult or 20% FBS/MEMα (both containing Rock, inhibitor and 1% Penicillin-Streptomycin).

—Differentiation Induction

After confirmation of colony formation, medium containing 1 uM retinoic acid (Sigma-Aldrich Corp.) and 25 ng/mL BMP4 (R&D Systems) was added to the well and cultured at 5% $CO_2$, 37° C. to induce differentiation into keratinocytes. An all-in-one microscope (KEYENCE CORPORATION) was used to observe Tomato-positive/negative cells.

9. Transcriptome Analysis (RNA-seq of Cell Populations)

RNA was extracted from the cell population, and an RNA-seq library was created according to Smart-seq2 protocol (Nature Protocols 9, 171-181 (2014) doi: 10.1038/nprot.2014.006). The obtained library was sequenced with Nextseq 500 (Illumina, Inc.) using a nextseq high output kit (37 bp pair end reads). Using bcl2fastq v2.17.1.14 of Illumina, Inc. with default parameters and optional-no-lane-splitting, conversion of base calls to fastq format and demultiplex were performed. Reads were trimmed using TrimGalore (http://www.bioinformatics.babraham.ac.uk/projects/trimg alore/), and mapping and counting (quantification) were performed using RSEM (Li et al., BMC Bioinformatics 12, 323 (2011); version STAR-2.5.2b). Differential expression analysis among samples was performed using DESeq2 (Love et al., Genome Biol. 15, 550 (2014)). Differentially Expressed Genes (DEGs) were uploaded to the Ingenuity Pathway Analysis (IPA) software (https://www.qiagenbioinformatics.com) to extract the most relevant biological pathways and functions to DEGs. Clustering analysis was performed using ICGS algorithm of AltAnalyzev.2.1.0-Py based on log 2 converted values of 1-added TPM (Transcripts Per kilobase Million) counts obtained with RSEM (log 2(TPM+1)).

10. Transcriptome Analysis (Single-Cell RNA-seq)

Single cell suspension was prepared, and cell viability was evaluated with an automated cell counter TC20 (Bio-Rad). A single-cell RNA-seq library was created using ddSEQ Single-Cell Isolator and SureCell WTA 3' Library prep kit according to the manufacturer's protocol. The obtained library was sequenced with Nextseq 500 (Illumina, Inc.) using a Nextseq high output kit (Read 1: 68 bp, Read 2: 75 bp). Using bcl2fastq v2.17.1.14 of Illumina, Inc. with default parameters and optional-no-lane-splitting, conversion of base calls to fastq format and demultiplex were performed. Any synthetic and sequencing errors that may occur in the cell barcode region were corrected with Edit distance (ED)<2. Reads were analyzed (by mapping and quantification) using Drop-Seq Tools v1.12 (STAR version: STAR-2.5.2b) to generate a digital expression matrix. The resulting matrix was standardized with voom (limma 3.32.10). Clustering analysis with ICGS algorithm was performed using AltAnalyze v.2.1.0-Py with default settings based on the standardized matrix. Based on the standardized matrix, dimensional compression with tSNE algorithm (using Rtsne), and clustering analysis using hclust (method=ward.D2) were also performed, and the results were plotted with ggplot2 or plot.ly. DESingle was used for Differential expression analysis.

11. FACS Analysis

FACS analysis was performed on bone marrow cells collected from vertebra and femur with fluorescently labeled antibodies against various surface molecules. A series of processes including fluorescence detection, sorting, and the like were performed using BD FACS Aria III system, and analysis of the obtained data was performed with FlowJo software Ver. 6.3.3 (Tree Star, Ashland, OR).

12. Parabiosis and Cartilage Defect Models

A parabiosis model was created using a 6-week old male wild-type mouse and a 6-week old male P0-Cre::Rosa26-tdTomato mouse using the method described in 3 above. After completion of the blood chimera at 4 weeks after operation, a 0.5×0.5×0.5 mm cartilage defect was created in the knee joint of the wild-type mouse using a 0.5 mm-diameter hand-turned drill (manufactured by MEISINGER USA, L.L.C.). Shortly after the cartilage defect was created, 100 μg of HA1-44 peptide diluted with 100 μL of saline was administered from the tail vein and subsequently administered at the same dose twice a week until 4 weeks after operation. To the control group, 100 μL of saline was administered to each mouse from the tail vein on the same schedule as in the HA1-44 peptide administration group. A knee joint was collected 12 weeks after knee cartilage defect creation, then fixation with 4% paraformaldehyde (overnight), deashing with 0.5 M EDTA solution (3 days), and 30% sucrose replacement (1 day) were performed to create a frozen block. It was sliced at a thickness of 10 μm using a cryostat, and the distribution of Tomato-positive cells was analyzed by confocal microscopy. A cartilage defect was also created in the knee joint using an 8-week old male wild-type mouse in the same way as described above, and the HA1-44 peptide was administered at the same dose and schedule as described above, then the knee joint was collected 2, 4, 8 and 12 weeks after knee cartilage defect creation to stain the tissue sections with safranin 0.

Abbreviation

Abbreviations for markers (XX, YY are the desired gene/protein name)

XX$^+$: XX-positive

XX$^-$: XX-negative

YY$^{lin+}$: YY lineage-positive

YY$^{lin-}$: YY lineage negative

PDGFR: platelet-derived growth factor receptor

Pα: platelet-derived growth factor receptor alpha (PDGFRα)

Pα cell: PDGFRα-positive cell

MSC: mesenchymal stem cell

EMSC: ectomesenchymal stem cell

CFPα cells: colony-forming Pα cells iCFPα cells: necrotic injury-induced colony-forming Pα cells CFU: colony-forming unit LepR: Leptin receptor Example 1

Properties of iCFPα Cells in Peripheral Blood

Figure 2:
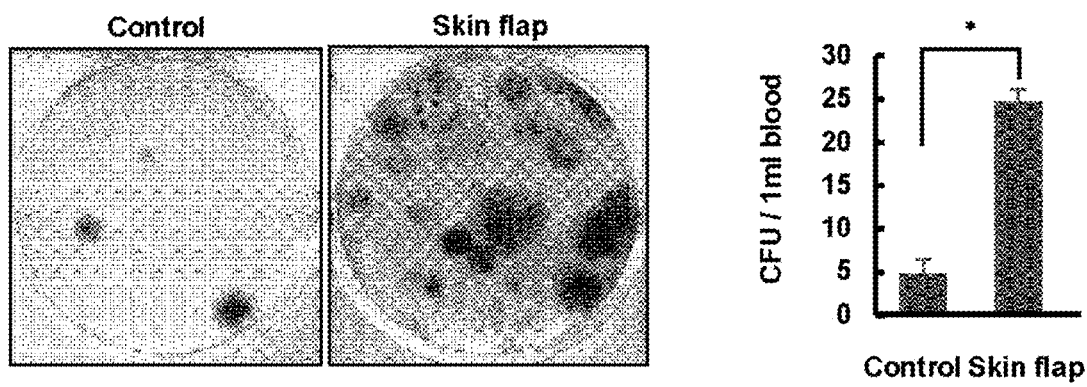
FIG. 2 is photographs of a colony obtained by culturing peripheral blood of mice, and a graph showing CFU activity converted per mL of peripheral blood.

A skin flap was created on the back of Pα-H2B-GFP mice, and 12 hours later, peripheral blood was collected, and the number of Pα cells contained in the peripheral blood was examined. As a result, Pα cells were significantly increased in the skin flap group compared to the control group in which no skin flap was created. The increase of Pα cells was correlated with HMGE1 concentration increase in peripheral blood (FIG. 1). A colony assay was also performed by culturing the peripheral blood of Pα-H2B-GFP mice. As the result, the skin flap group had significantly more colonies (all Pα-positive cells) than the control group, showing higher CFU activity (FIG. 2). Such results indicate that a necrotic tissue injury causes an increase of colony-forming Pα cells in peripheral blood.

Figure 3:
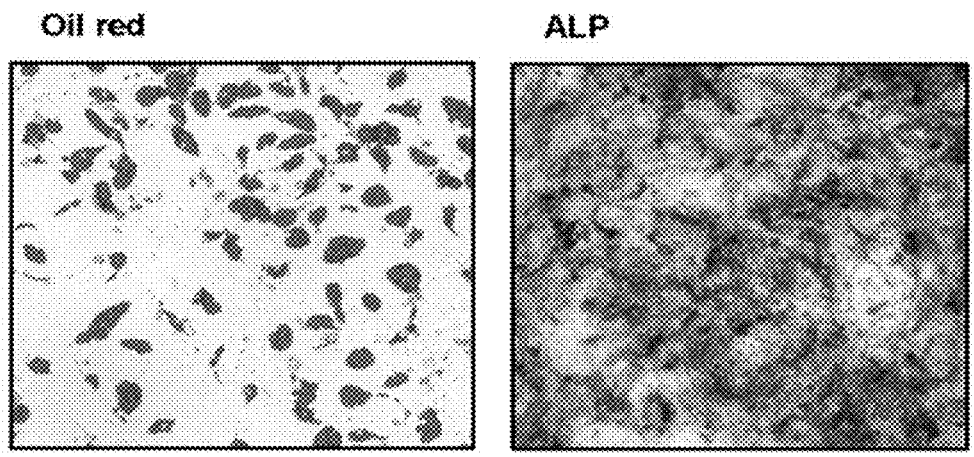
FIG. 3 is photographs showing results of differentiation induction of iCFP$\alpha$ cells obtained from mouse peripheral blood into osteoblasts, adipocytes, chondrocytes, and keratin-5 expressing cells. Osteoblasts were detected by ALP staining, adipocytes were detected by Oil Red-O staining, chondrocytes were detected by Toluidine blue staining, and keratin-5 expressing cells were detected by fluorescence of reporter protein tdTomato.

Furthermore, colony-forming Pα cells (i.e., iCFPα cells) obtained by culturing the peripheral blood of mice in which a skin flap was created exhibited differentiation potency into osteoblasts, adipocytes and chondrocytes, and further exhibited differentiation potency into cells expressing Keratin 5 (Krt5, K5) under a differentiation-inducing condition into keratinocytes (FIG. 3).

Figure 4:
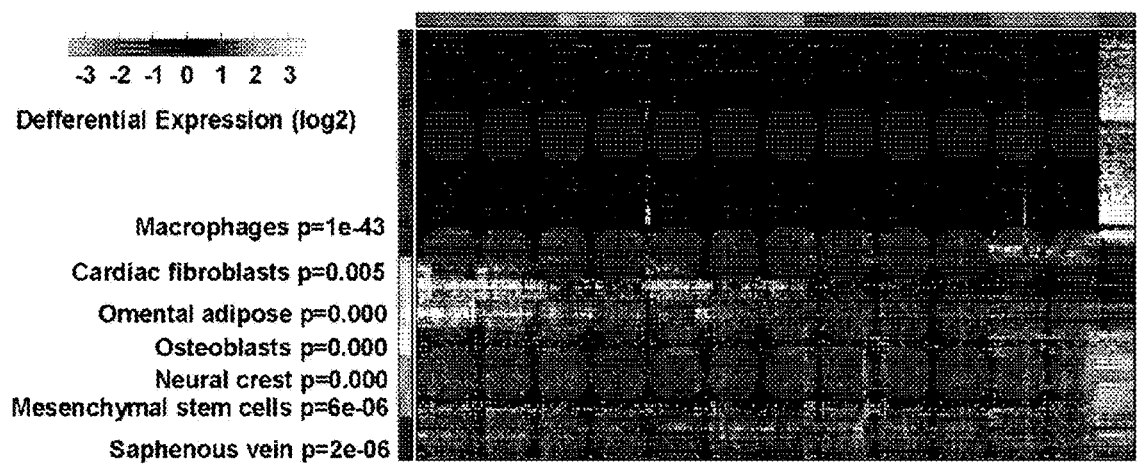
FIG. 4 is a diagram showing the results of performing single-cell transcriptome analysis on iCFP$\alpha$ cells and performing clustering analysis based on the obtained data. The cell types shown on the left are predicted cell types based on gene expression profiles (such as high expression of a particular gene set).
Figure 5:
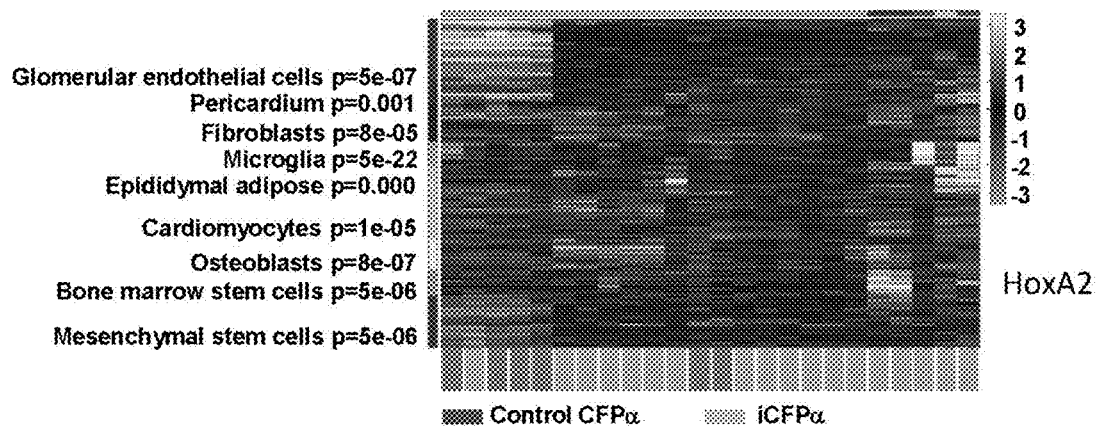
FIG. 5 is a diagram showing the results of performing transcriptome analysis on iCFP$\alpha$ cells on a colony basis and performing clustering analysis. The cell types shown on the left are predicted cell types based on gene expression profiles (such as high expression of a particular gene set). In the diagram, one column corresponds to one colony.

Single-cell transcriptome analysis was performed on CFPα cells derived from peripheral blood after skin flap creation (iCFPα cells). As the result, most cells showed high expression of gene groups corresponding to cell types including MSC (FIG. 4). Cells expressing genes characteristic of epidermal cells such as Krt8 and Krt18 were also included. Furthermore, transcriptome analysis on a colony basis was performed on CFPα cells derived from peripheral blood in the control and the skin flap groups, and clustering analysis with the ICGS algorithm was performed. As the result, in clusters where CFPα cells after skin flap creation accounted for majority, expression of gene groups characteristic of cell types including bone marrow stem cells and MSC was high. Especially, expression of HoxA2 gene was characteristically high (FIG. 5).

Example 2

Surface Markers of iCFPα Cells in Peripheral Blood

Figure 6:
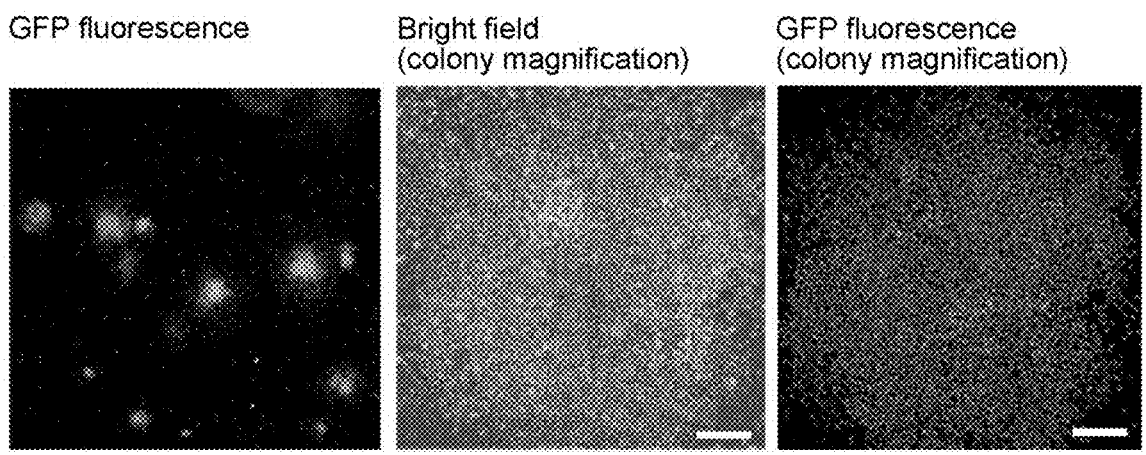
FIG. 6 is a photograph of colony-forming cells obtained by culturing peripheral blood of P$\alpha$-H2B-GFP mice.

In both the control group and the skin flap group, all colonies obtained by culturing peripheral blood were Pα-positive (FIG. 6). Furthermore, a single cell transcriptome analysis of peripheral blood CFPα cells (iCFPα cells) in the skin flap group resulted in CD34-positive and Sca1-negative.

Example 3

Cell Lineage Markers of iCFPα Cells in Peripheral Blood

Figure 7:
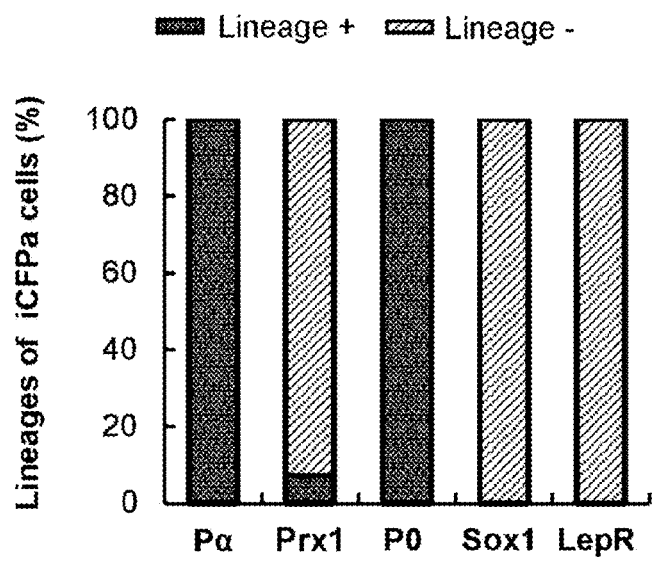
FIG. 7 is a graph showing the results of examining negative/positive rates of P$\alpha$ lineage, P0 lineage, Prx1 lineage, Sox1 lineage, and LepR lineage for iCFP$\alpha$ cells.

Peripheral blood-derived CFPα cells of skin-flap-created mouse (iCFPα cells) were lineage-traced for Pα lineage, P0 lineage, Prx1 lineage, Sox1 lineage, and LepR lineages using a transgenic mouse utilizing a Cre-loxP system. As a result, all iCFPα cells were Pα lineage-positive, P0 lineage-positive, Sox1 lineage-negative, and LepR lineage-negative (FIG. 7). For Prx1-lineage, 93% of iCFPα cells were negative (FIG. 7).

Figure 8:
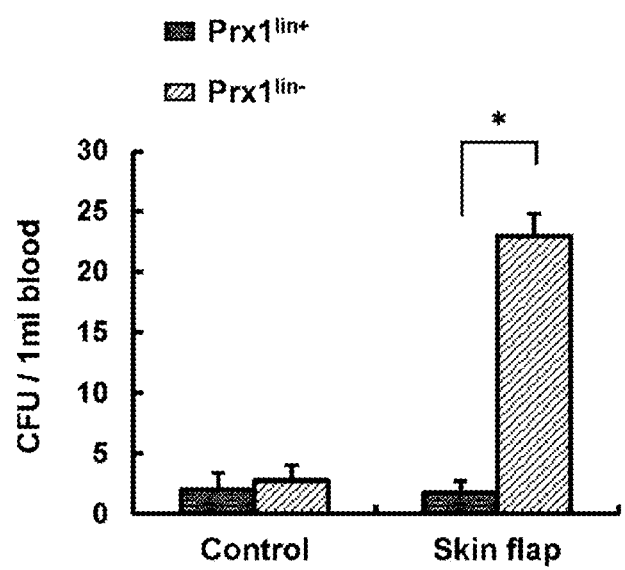
FIG. 8 is a graph showing the results of CFU activity of colony-forming cells obtained from peripheral blood assessed by Prx1 lineage for each of the skin flap-created mouse and the skin flap-not created mouse.

Although a small amount of Prx1 lineage-positive and negative colony-forming cells are present in blood even at normal state, only Prx1 lineage-negative cells were increased by a skin flap (FIG. 8). Thus, iCFPα cells can be defined as Prx1 lineage-negative.

It is believed that iCFPα cells in peripheral blood are derived from ectoderm, because they were P0$^{lin+}$ and Prx1$^{lin-}$. Furthermore, considering that they were Sox1$^{lin-}$ and that HoxA2 gene was highly expressed, it is suggested that they are cells whose embryological origin is cranial neural fold.

Example 4

Exploration of Ectodermal Derived Mesenchymal Cell

Figure 9:
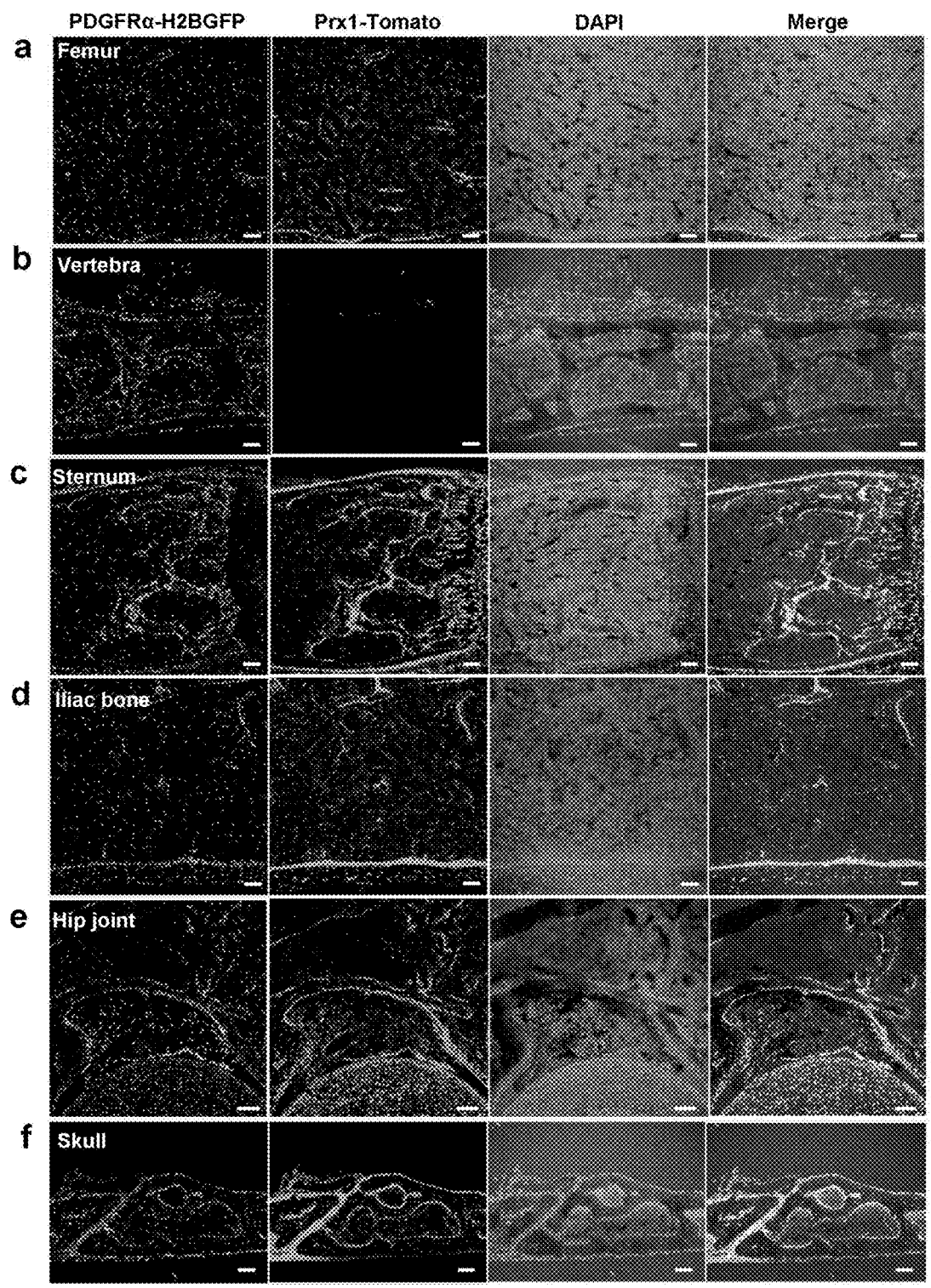
FIG. 9 is photographs showing the results of detecting P$\alpha$ expression and Prx1 lineage for cells present in bone marrow tissue of the femur, vertebra, sternum, ilium, hip joint (femoral head and lumbar lid) and skull of P$\alpha$-H2B-GFP::Prx1-Cre::Rosa26-tdTomato mice.
Figure 10:
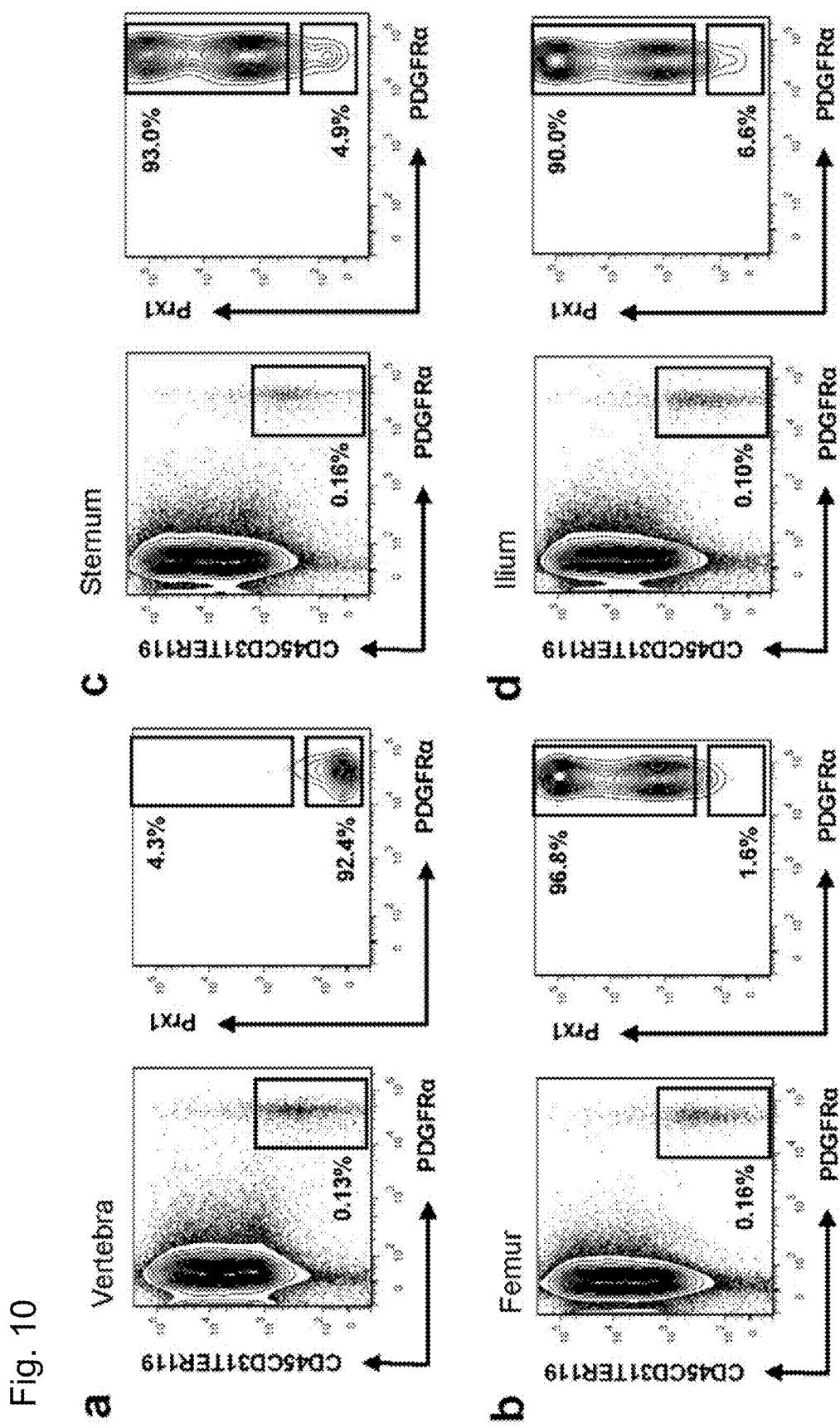
FIG. 10 is a diagram showing the results of FACS analysis on bone marrow cells in the femur, vertebra, sternum and ilium of P$\alpha$-H2B-GFP::Prx1-Cre::Rosa26-tdTomato mice.

Upon examination of bone marrow tissue of the femur, vertebra, sternum, ilium, hip joint (femoral head and lumbar lid), and skull collected from Pα-H2B-GFP::Prx1-Cre::Rosa26-tdTomato mouse, Pα$^{+}$ and Prx1$^{lin-}$ cells were specifically present in the vertebra (within the scope of this investigation) (FIGS. 9 and 10).

Example 5

Lineage Markers of CFPα Cells in Vertebra and Femur

Figure 11:
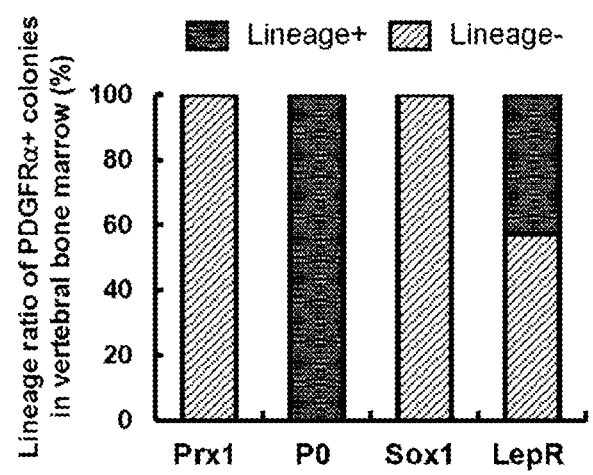
FIG. 11 is a graph showing the results of examining P0 lineage, Prx1 lineage, Sox1 lineage and LepR lineage for CFP$\alpha$ cells derived from vertebral bone marrow.
Figure 12:
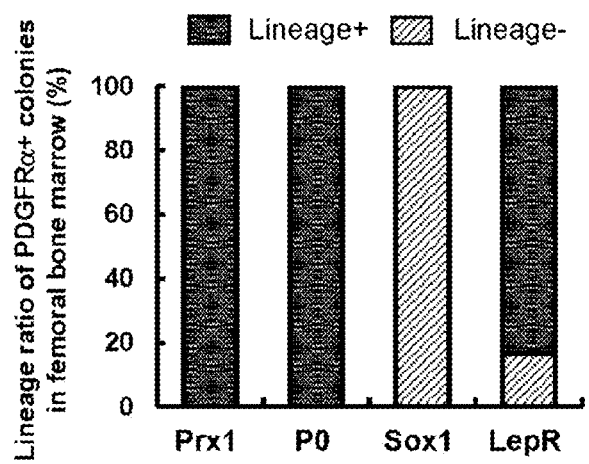
FIG. 12 is a graph showing the results of examining P0 lineage, Prx1 lineage, Sox1 lineage and LepR lineage for CFP$\alpha$ cells derived from femoral bone marrow.
Figure 13:
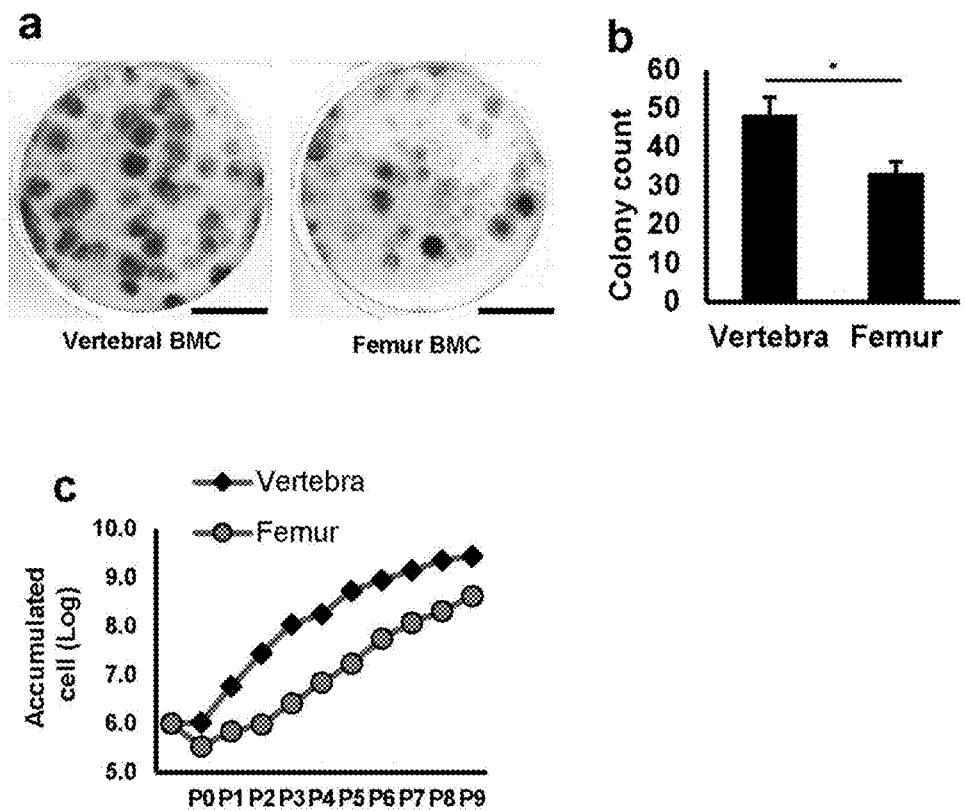
FIG. 13 shows (a) photographs of colonies, (b) colony numbers, and (c) growth curves for vertebral and femoral bone marrow-derived CFP$\alpha$ cells. The transverse axis of (c) indicates the passage number (P0=primary culture).
Figure 14:
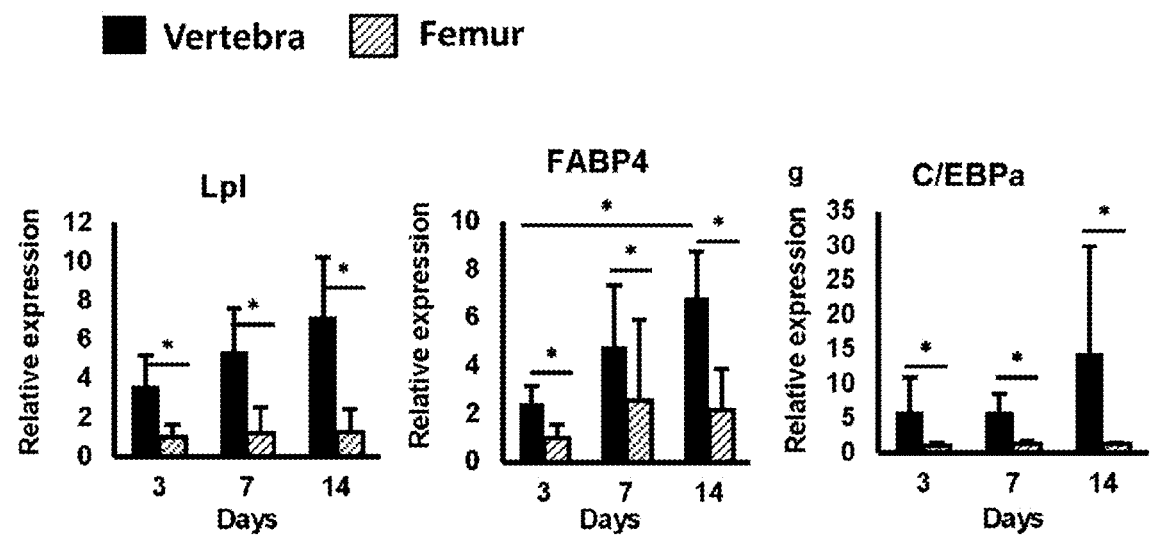
FIG. 14 is graphs showing the results of culturing vertebral and femoral bone marrow-derived CFP$\alpha$ cells under a differentiation-inducing condition into adipocytes, and examining the expression of differentiation markers of adipocytes.
Figure 15:
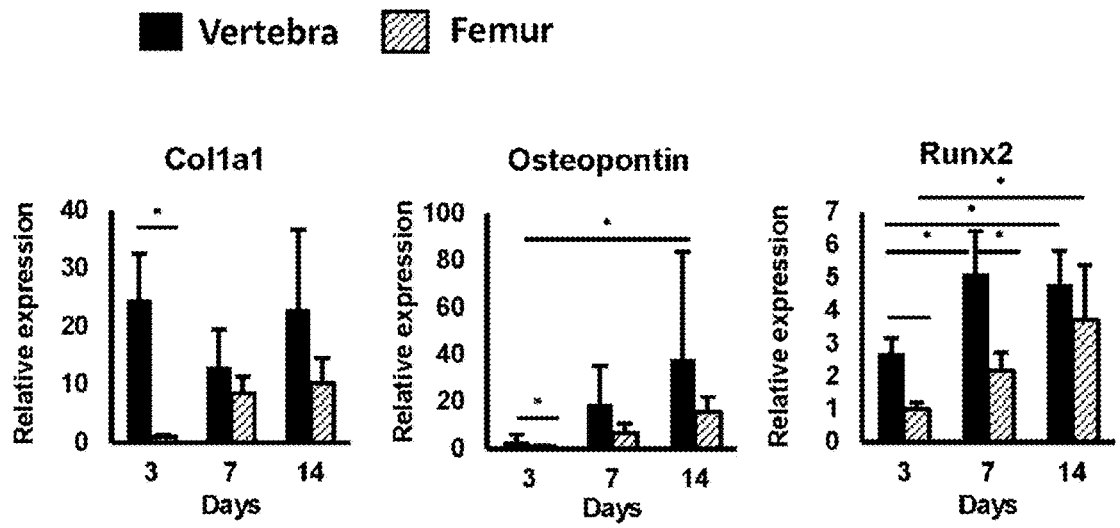
FIG. 15 is graphs showing the results of culturing vertebral and femoral bone marrow-derived CFP$\alpha$ cells under a differentiation-inducing condition into osteoblasts, and examining the expression of differentiation markers of osteoblasts.
Figure 16:
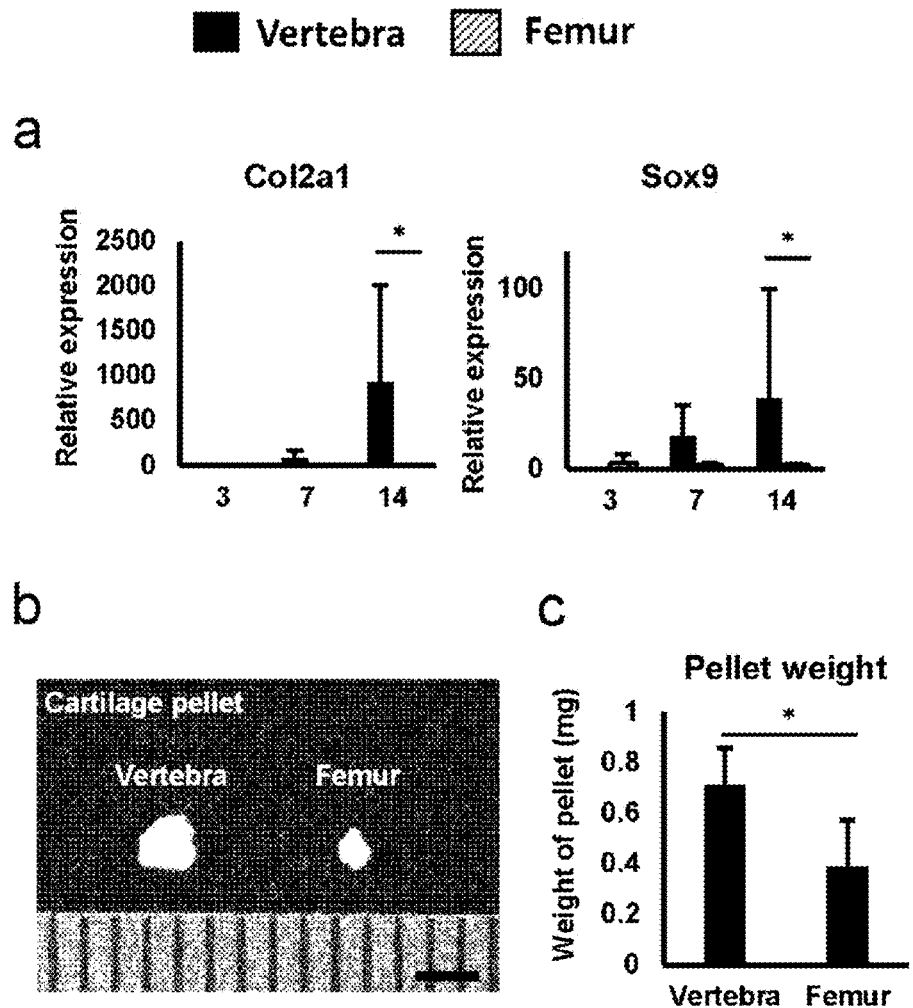
FIG. 16 is (a) graphs showing the results of culturing vertebral and femoral bone marrow-derived CFP$\alpha$ cells under a differentiation-inducing condition into chondrocytes, and examining the expression of differentiation markers of chondrocytes, and diagrams showing (b) photographs of formed chondropellets and (c) the weight of chondropellets.

For CFPα cells obtained by culturing vertebral and femoral bone marrow, P0 lineage, Prx1 lineage, Sox1 lineage, and LepR lineage were examined using a cell lineage tracing mouse. As the result, CFPα cells in the vertebra were P0$^{lin+}$, Prx1$^{lin-}$, and Sox1$^{lin-}$, and about 60% of them were negative for LepR$^{lin}$ (FIG. 11). CFPα cells in the femur were P0$^{lin+}$, Prx1$^{lin+}$, and Sox1$^{lin-}$, and about 80% of them were positive for LepR$^{lin}$ (FIG. 12). Such results suggest that a source of iCFPα cells (Pα$^{lin+}$, P0$^{lin+}$, Sox1$^{lin-}$, LepR$^{lin-}$) in peripheral blood is present in vertebra.

Example 6

Properties of CFPα Cells in Vertebra and Femur

Figure 17:
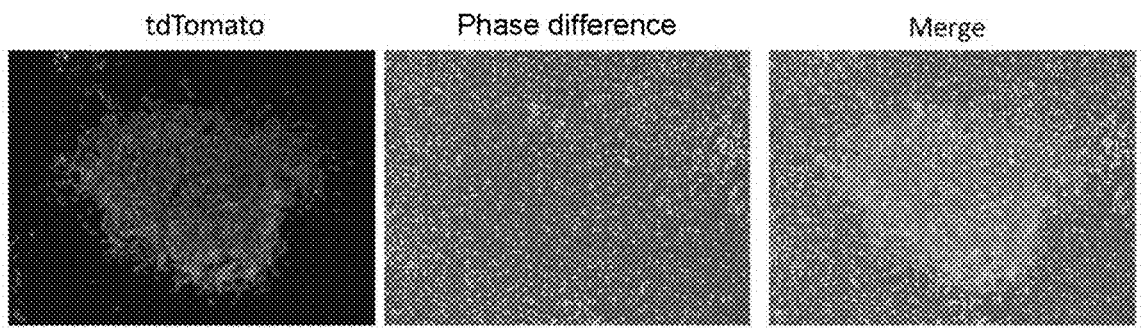
FIG. 17 is photographs of K5-expressing cells obtained by culturing vertebral bone marrow-derived CFP$\alpha$ cells under a differentiation-inducing condition into keratinocytes.
Figure 18:
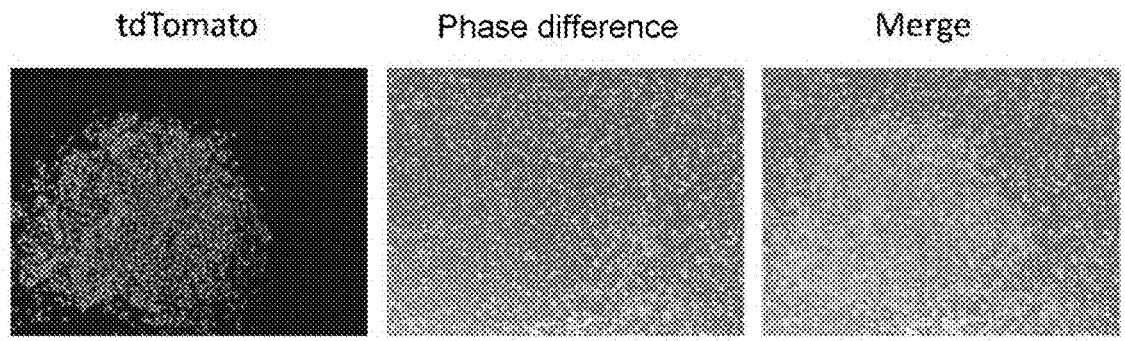
FIG. 18 is photographs of K5-expressing cells obtained by culturing femoral bone marrow-derived CFP$\alpha$ cells under a differentiation-inducing condition into keratinocytes.

Colony-forming ability and differentiation potency into osteoblasts, adipocytes and chondrocytes were compared between CFPα cells obtained by culturing vertebral bone marrow and those obtained by culturing femoral bone marrows. As the result, vertebral CFPα cells showed higher abilities in both colony-forming ability and differentiation potency (FIGS. 13 to 16). Furthermore, differentiation induction of CFPα cells of vertebra and femur was performed with all-transletinoic acid (ATRA) and BMP-4. As the result, a colony expressing Keratin 5 was observed (FIGS. 17 and 18), confirming that CFPα cells in vertebrae and femur include cells having differentiation potency into K5-positive cells.

Example 7

Transcriptome Analysis of Pα Cells in Vertebra and Femur

Figure 19:
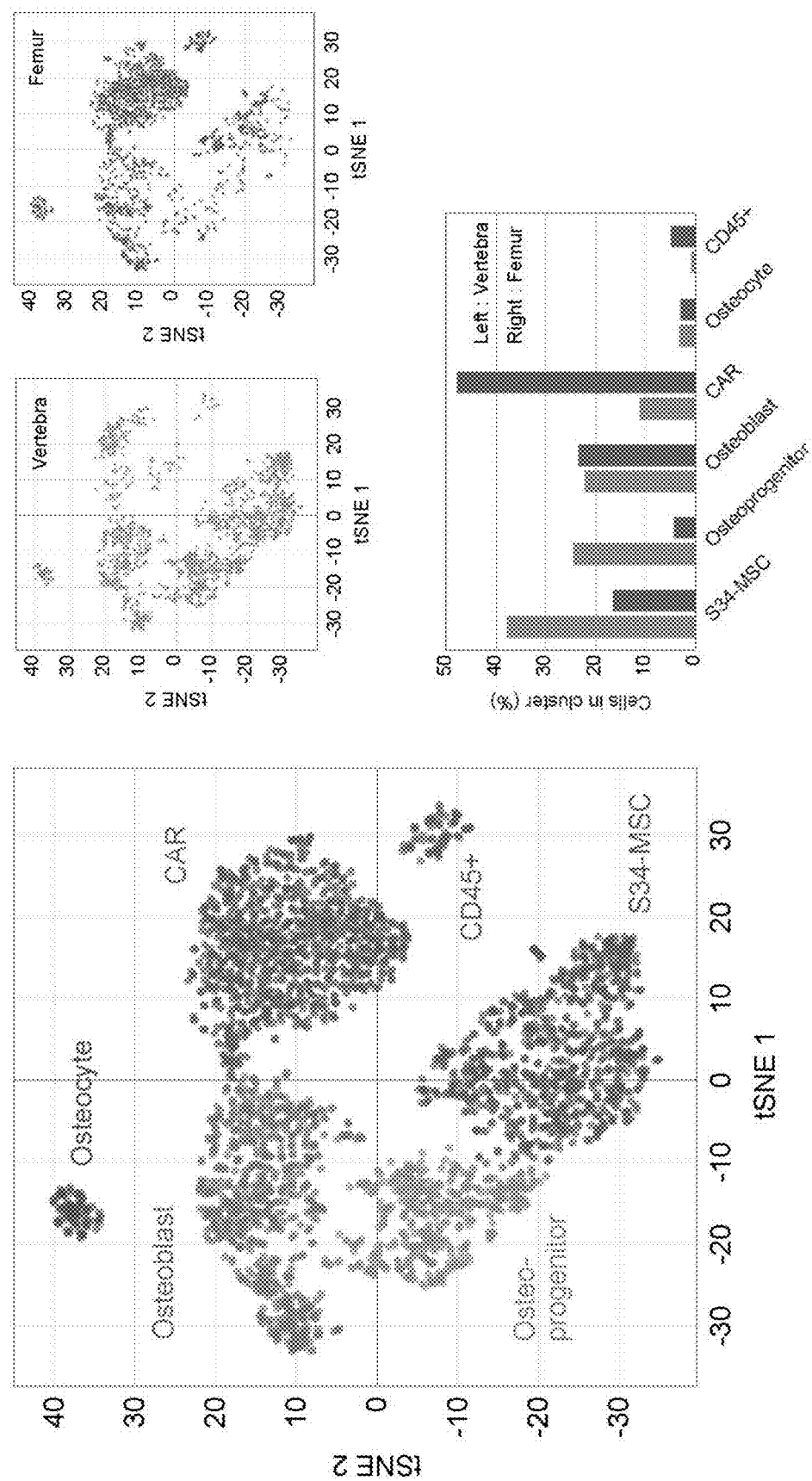
FIG. 19 is diagrams showing the results of performing single-cell transcriptome analysis on P$\alpha$ cells in vertebral and femoral bone marrows and performing clustering analysis based on the obtained data.

Pα cells were sorted from vertebral and femoral bone marrow cells, and single-cell transcriptome analysis was performed. As the result of clustering analysis, Pα cells in the bone marrow were divided into six clusters (FIG. 19). The six clusters were defined as (1) S34-MSC (Sca1 and CD34-expressing), (2) osteoprogenitor (Osteomodulin and Wnt16-expressing), (3) osteoblast (osterix and osteocalcin-expressing), (4) osteocyte (PHEX and DMP1-expressing), (5) CAR cell (CXCL12 and LepR-expressing), and (6) CD45-expressing cell, based on the genes specifically expressed by the cells of each cluster. Comparing between vertebra and femur, it can be seen that the vertebra has more S34-MSC cluster cells and fewer CAR cluster cells, whereas the femur has more CAR cluster cells and fewer S34-MSC cluster cells.

Figure 20:
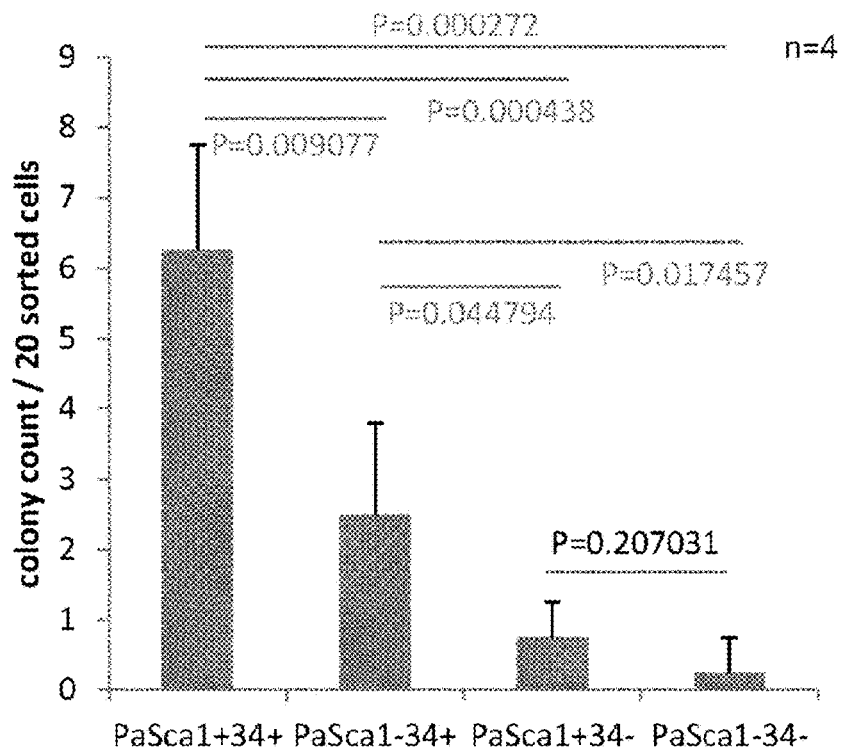
FIG. 20 is a graph showing the results of separating P$\alpha$ cells in vertebral bone marrow into four populations with FACS using Sca1 and CD34 expressions as indicators, and performing a CFU assay on the four populations.

In addition, cells of Sca1$^+$CD34$^+$, Sca1$^+$CD34$^-$, and Sca1$^-$CD34$^+$ were included in the S34-MSC cluster. Pα cells of vertebra were then separated by FACS using Sca1 and CD34 expressions as indicators, and a CFU assay was performed. As the result, CFU activity was high in the order of Sca1$^+$CD34$^+$ cells>Sca1$^+$CD34$^-$ cells and Sca1$^-$CD34$^+$ cells>Sca1$^-$CD34$^-$ cells (FIG. 20).

Example 8

Correspondence Between Pα Cells in Peripheral Blood and Pα Cells of Vertebra

Figure 21:
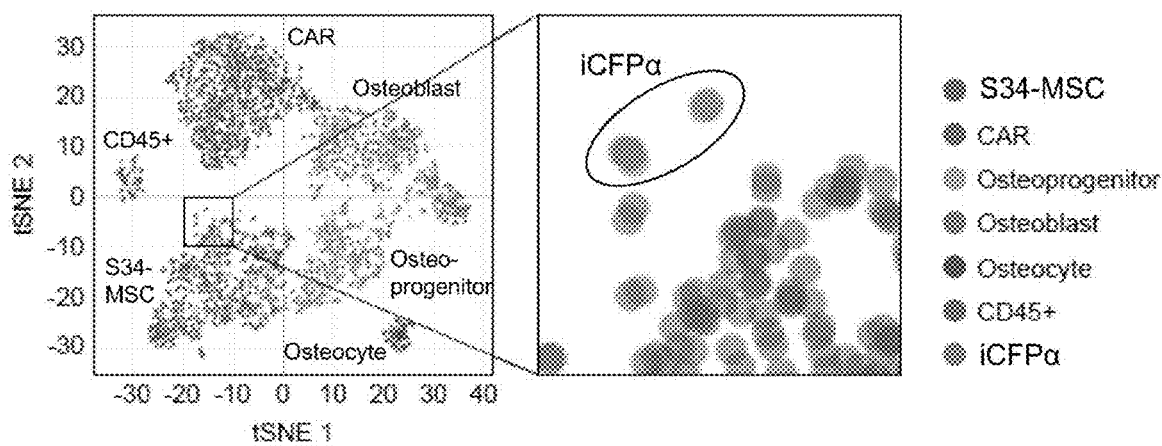
FIG. 21 is a diagram showing the results of subjecting iCFP$\alpha$ cells in peripheral blood to clustering analysis with vertebral and femoral P$\alpha$ cells.

Clustering analysis was performed with Pα cells of vertebra and femur, based on transcriptome analysis data of iCFPα cells in peripheral blood. As the result, iCFPα cells in peripheral blood were located near the S34-MSC cluster (FIG. 21). Furthermore, the peripheral blood iCFPα cell was CD34$^+$Sca1$^-$. Considering this result in conjunction with lineage markers, it is suggested that peripheral blood iCFPα cells correspond to CD34$^+$Sca1$^-$ cells included in the S34-MSC cluster of vertebra.

Example 9

Sca1$^+$CD34$^+$ Cells in Bone Marrow

Figure 22:
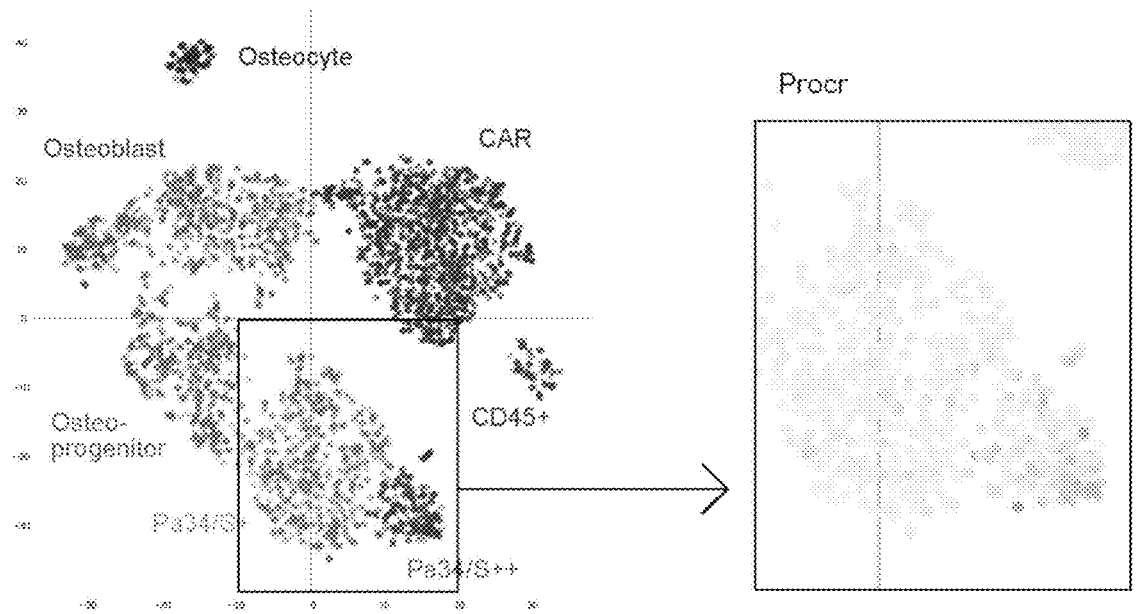
FIG. 22 is a diagram showing the expression of Procr in cells of the S34-MSC cluster in bone marrow.
Figure 23:
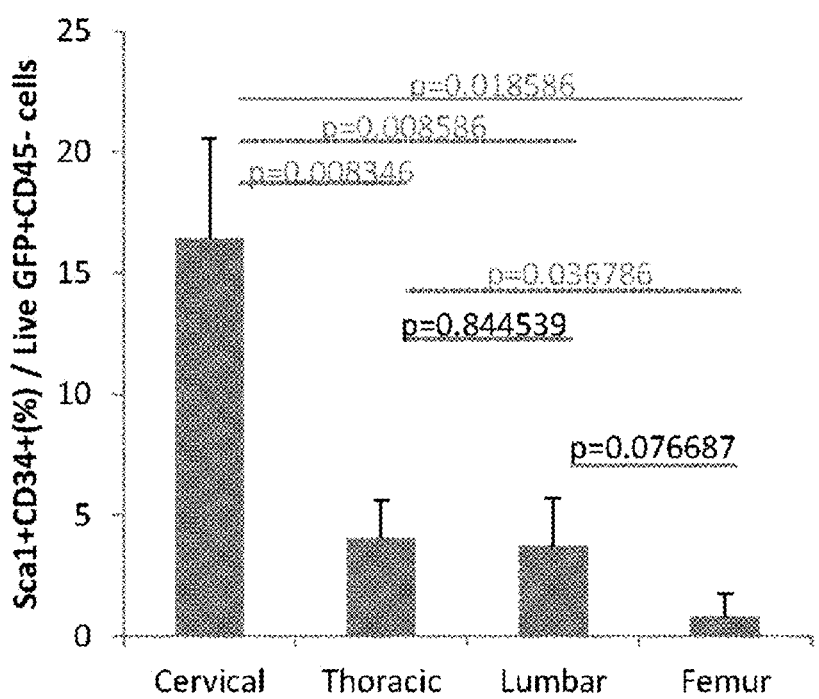
FIG. 23 is a graph showing the amount of Sca1$^+$CD34$^+$ cells present in the bone marrow of cervical vertebra, thoracic vertebra, lumbar vertebra and femur of P$\alpha$-H2B-GFP mice (as a percentage relative to PDGFR$\alpha^+$CD45$^-$ live cells).

Sca1$^+$CD34$^+$ cells contained in the S34-MSC cluster of bone marrow specifically expressed Procr (FIG. 22). Thus, Procr can be a marker for Sca1$^+$CD34$^+$ cells that are considered to be the most proliferative and the most hierarchical cell among bone marrow Pα cells. Furthermore, an examination of the amount of Sca1$^+$CD34$^+$ cells present in cervical vertebra, thoracic vertebra, lumbar vertebra and femur showed that amount was high in the order of cervical vertebra>thoracic vertebra>lumbar vertebra>femur (FIG. 23).

Example 10

Figure 24:
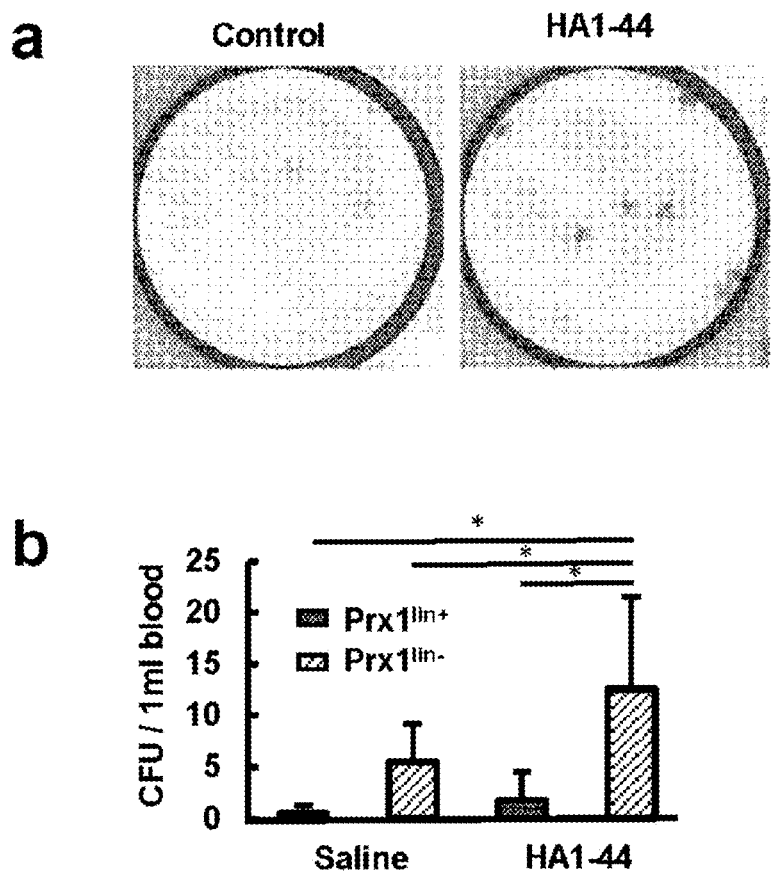
FIG. 24 is (a) photographs of colony-forming cells obtained by culturing peripheral blood, and (b) a graph showing CFU activity of the cells converted per mL of peripheral blood.

Contribution of Circulating Cells in Blood Induced by HMGB1 Administration to Tissue-Regeneration The present inventors have previously identified a peptide (HA1-44 peptide) consisting of the amino acid sequence of positions 1-44 (SEQ ID NO: 1) at the N-terminus of HMGB1 protein as a domain having the activity of mobilizing bone marrow-derived Pα-positive mesenchymal stem cells into peripheral blood. Now, the present inventors have obtained the following experimental results concerning cells in peripheral blood induced by administration of the HA1-44 peptide.
(1) Culturing peripheral blood of the lineage tracing mice administered the HA1-44 peptides resulted in more colonies than peripheral blood in the control group (saline administration). All of the colonies were Pα-positive, and the majority of which were Prx1 lineage-negative (FIG. 24).

Figure 25:
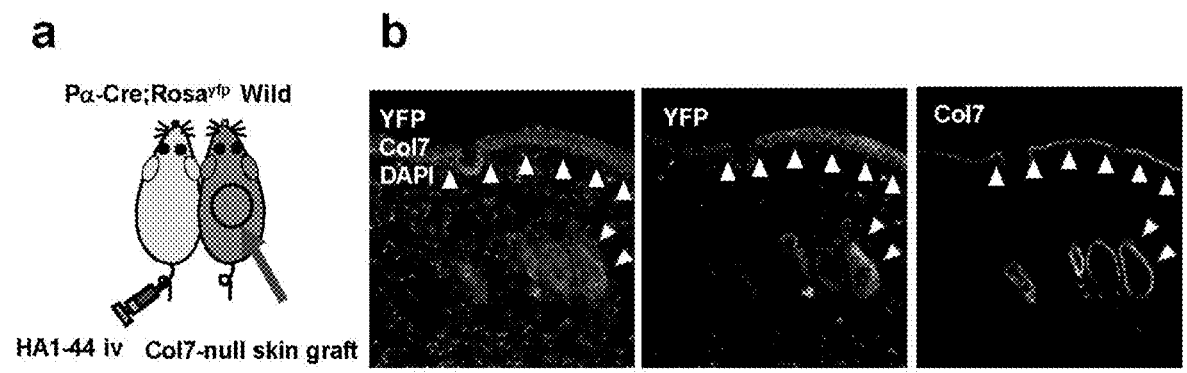
FIG. 25 is (a) a diagram showing a schematic of the parabiosis model, and (b) photographs showing the observation results of grafted skin tissue after administration of the HA1-44 peptide. Pα cells were detected with YFP fluorescence, and type 7 collagen was detected with antibodies.
Figure 26:
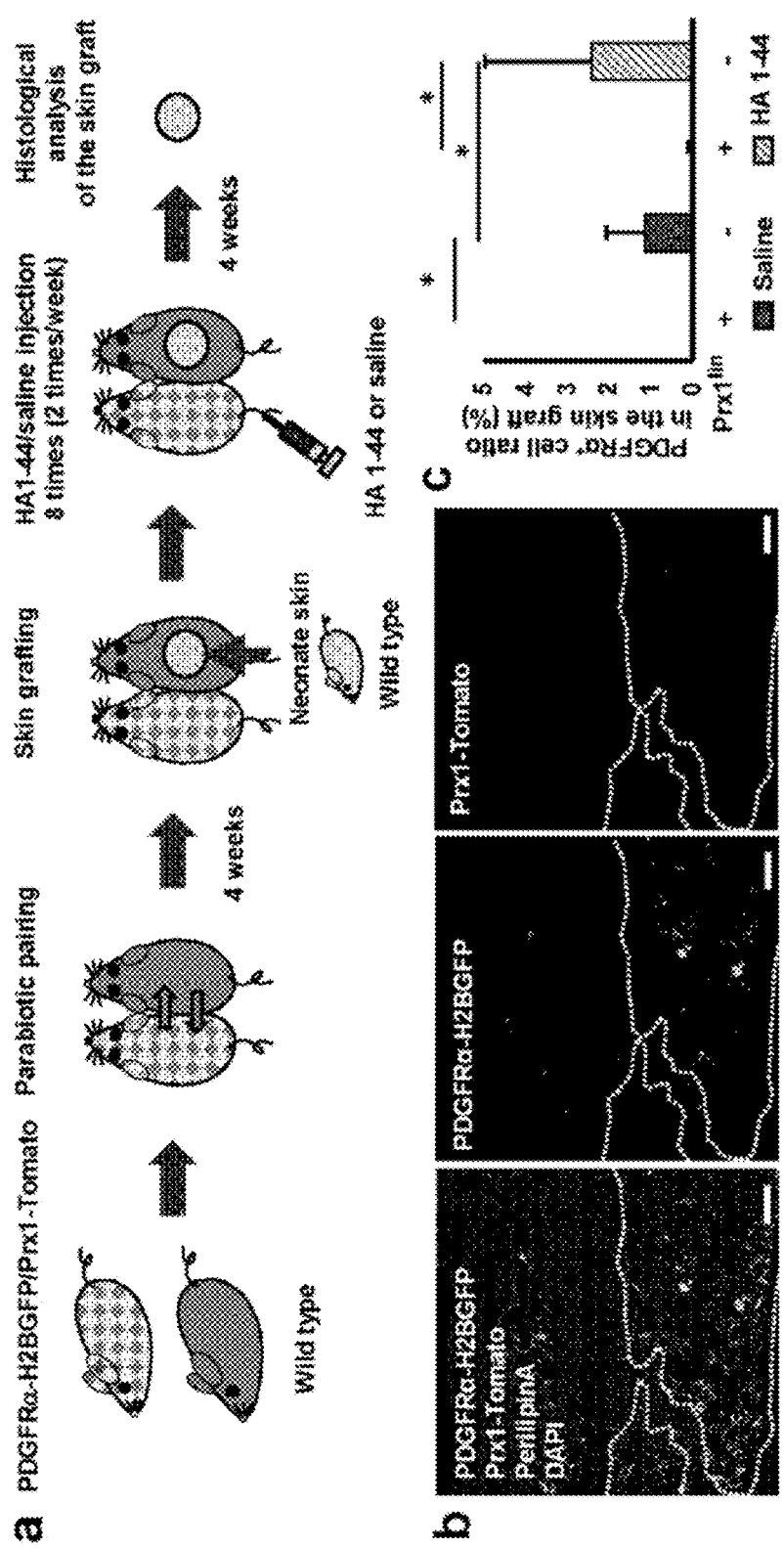
FIG. 26 is (a) a diagram showing a schematic of a parabiosis model, (b) photographs showing observation results of grafted skin tissue after HA1-44 peptide administration, and (c) a graph showing a percentage of PDGFRα$^+$ cells in the grafted skin tissue. PDGFRα expression was detected by fluorescence of GFP, and Prx1 lineage was detected by fluorescence of a reporter protein tdTomato.
Figure 28:
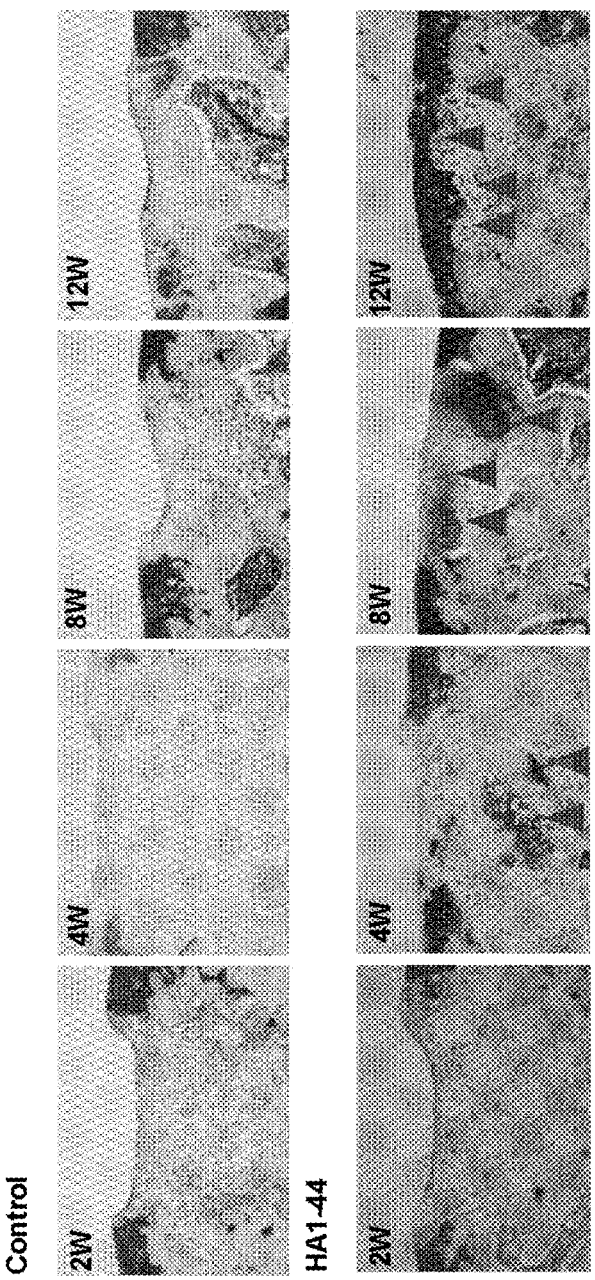
FIG. 28 is photographs showing tissue observation results (safranin O staining) of knee cartilage injury sites in the control group (saline administration) and the HA1-44 peptide administration group at 2, 4, 8 and 12 weeks after knee cartilage defect creation. The arrowheads indicate the part where regeneration of the hyaline cartilage was observed.

(2) A parabiosis model of Pα-Cre::Rosa26-EYFP mouse and wild-type (WT) mouse was created, and a skin of epidermolysis bullosa mouse was grafted into the wild-type mouse, then HA1-44 peptide was administered to Pα-Cre::Rosa26-EYFP mouse. As the result, the presence of Pα$^{lin+}$ cells expressing type 7 collagen was confirmed in a regenerated epithelial tissue in the skin graft (FIG. 25).
(3) A parabiosis model of Pα-H2B-GFP::Prx1-Cre::Rosa26-tdTomato mouse and a wild-type mouse was created, and a skin of a wild-type neonate mouse was grafted on the back of the wild-type mouse, then the HA1-44 peptide was administered to the Pα-H2B-GFP::Prx1-Cre::Rosa26-tdTomato mouse. As the result, the presence of Pα+ and Prx1$^{lin-}$ cells in the skin graft was confirmed (FIG. 26).
(4) A parabiosis model of P0-Cre::Rosa26-tdTomato mouse and a wild-type mouse was created, and a cartilage injury was created to the knee joint of the wild-type mouse, then the HA1-44 peptide was administered to the P0-Cre::Rosa26-tdTomato mouse. As the result, the accumulation of P0$^{lin+}$ cells was confirmed at the cartilage injury site in the HA1-44 peptide administration group, whereas no accumulation of P0$^{lin+}$ cells was seen in the control group (saline administration) (FIG. 27). Furthermore, a cartilage injury was created to the knee joint of a wild-type mouse alone that was not a parabiosis model, then the HA1-44 peptide or saline was administered. As the result, hyaline cartilage was regenerated at the cartilage injury site in the HA1-44 peptide administration group, whereas only fibrous cartilage was seen at the cartilage injury site in the saline administration group (FIG. 28).

From the above results, it is believed that Pα cells (Pα$^+$P0$^{lin+}$Prx1$^{lin-}$ cells) in peripheral blood induced by the HA1-44 peptide are the same as iCFPα cells induced by a necrotic tissue injury, or include at least iCFPα cells, which serve to repair injury of tissues such as epidermis and cartilage.

Example 11

Change in Cells Induced by HMGB1 Administration (1) Peripheral blood was collected from the mouse administered with the HA1-44 peptides and from the mouse administered with saline, and cultured on a plastic plate to obtain a colony of adhesive cells. Transcriptome analysis was performed on the cells on a colony basis, and clustering was performed with an ICGS algorithm based on the obtained data. The obtained results are shown in FIG. 29. In addition, FIG. 30 is a simplified representation of the results of the clustering. In the screening method of the present application, a substance having a result similar to the HA1-44 peptide, for example, a substance to have a result in which a cluster characterized by predicted cell types (or expression of a gene set corresponding to predicted cell types) similar to FIG. 30 is formed, and the number of colonies belonging to each cluster is "cluster 1: saline group test substance group, cluster 2: saline group<test substance group, cluster 3: saline group>test substance group, cluster 4: saline group>test substance group" can be evaluated as a candidate for a substance having multipotent stem cell-inducing activity.

Figure 31:
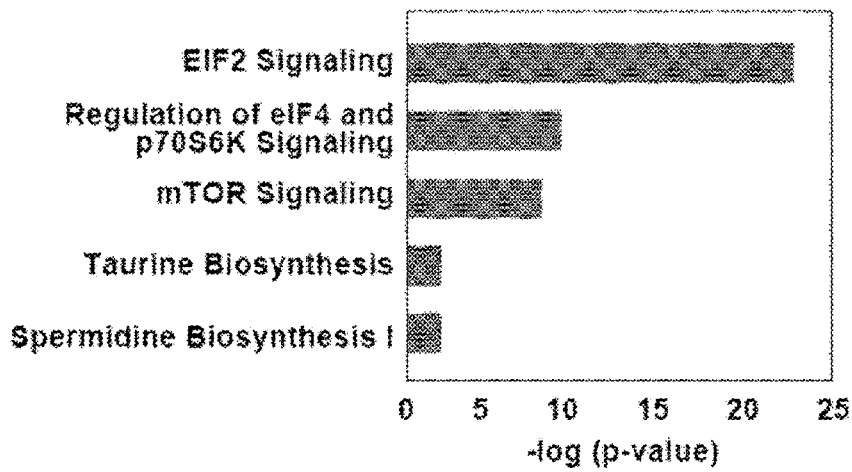
FIG. 31 is a graph showing the results of a pathway analysis performed based on transcriptome analysis data of vertebral Pα cells of mice in the HA1-44 peptide administration group and the saline administration group.
Figure 32:
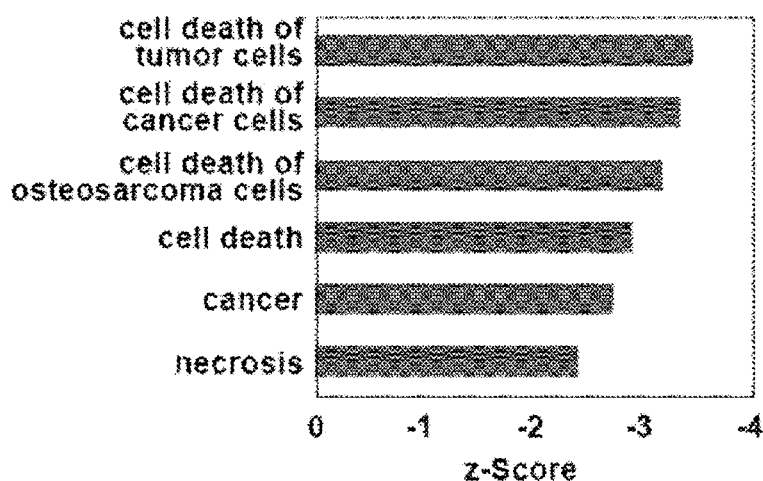
FIG. 32 is a graph showing the results of a pathway analysis (function analysis) performed based on transcriptome analysis data of vertebra Pα cells of mice in the HA1-44 peptide administration group and the saline administration group.

(2) Transcriptome analysis was performed on Pα cells of vertebra collected from the mouse administered with HA1-44 peptide and the mouse administered with saline, and pathway analysis was performed with IPA based on the obtained data. As the result, pathways associated with EIF2 signaling, regulation of eIF4 and p70S6K signaling, and mTOR signaling were activated in vertebral Pα cells in the HA1-44 peptide administration group compared to those in the control group (FIG. 31). Furthermore, expression of cell death-related genes was suppressed in vertebral Pα cells in the HA1-44 peptide administration group compared to those in the control group (FIG. 32).

Example 12

Activity of HMGB1 Peptide in Human

Figure 33:
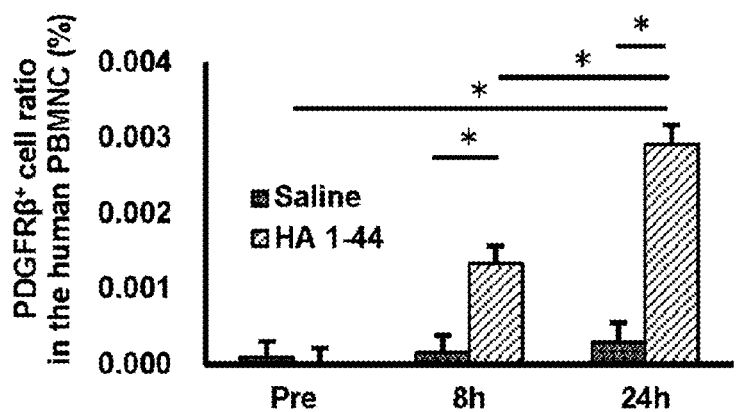
FIG. 33 is a graph showing the percentages of CD45-negative, TER-119-negative, and PDGFRβ-positive cells in human peripheral blood mononuclear cell fractions collected before, 8 hours after, and 24 hours after administration of the HA1-44 peptide.

In Phase I clinical studies, intravenous administration of the HA1-44 peptide showed an increase of CD45-negative, TER-119-negative, and PDGFRβ-positive cells in circulating blood (FIG. 33). Since PDGFRβ is a marker of human mesenchymal stem cells, it is believed that a marker (including a combination of multiple markers) defining iCFPα cells and vertebral CFPα cells in peripheral blood described herein, in which the term "PDGFRα" is replaced with the term "PDGFRβ", will also be a marker (including a combination of multiple markers) defining EMSC (colony-forming PDGFR-positive cells in peripheral blood or in vertebra) in humans.

INDUSTRIAL APPLICABILITY

An ectomesenchymal stem cell in peripheral blood according to the present invention has superior proliferative ability and multi-lineage differentiation potency than a bone marrow-derived mesenchymal stem cell conventionally used in regenerative medicine, and can be used in a cell transplantation therapy or the like as a therapeutic cell obtainable by peripheral blood collection method that is less invasive than bone marrow aspiration. Furthermore, the characteristics (markers, or the like) of ectomesenchymal stem cells in peripheral blood that contribute to the regeneration of injured tissues have been revealed. Thus, a substance having an activity to induce multipotent stem cells in vivo can be efficiently screened using the cell as an indicator.

animal selected from the group consisting of mouse, rat, monkey, pig, dog, rabbit, hamster, guinea pig, horse, and sheep;

2) collecting peripheral blood from a subject having a necrotic tissue injury, and selectively recovering a cell that is PDGFRα-positive and Prx1 lineage-negative from the peripheral blood, wherein the subject is a transgenic animal selected from the group consisting of mouse, rat, monkey, pig, dog, rabbit, hamster, guinea pig, horse, and sheep;

3) collecting peripheral blood from a subject having a necrotic tissue injury, and selectively recovering a cell that is PDGFRα-positive, CD34-positive and Sca1-negative from the peripheral blood, wherein the subject is selected from the group consisting of mouse, rat, and hamster;

4) collecting peripheral blood from a subject having a necrotic tissue injury, and selectively recovering a cell that is PDGFRα-positive, Prx1 lineage-negative, CD34-positive and Sca1-negative from the peripheral blood, wherein the subject is a transgenic animal selected from the group consisting of mouse, rat, and hamster;

5) collecting peripheral blood from a subject having a necrotic tissue injury, and selectively recovering a cell that is PDGFRα-positive and CD34-positive from the peripheral blood, wherein the subject is selected from the group consisting of human, mouse, rat, monkey, pig, dog, rabbit, hamster, guinea pig, horse, and sheep;

6) collecting peripheral blood from a subject having a necrotic tissue injury, selectively recovering a cell that is PDGFRα-positive and Prx1 lineage-negative from the peripheral blood, and culturing the cell to obtain a colony-forming cell, wherein the subject is a transgenic animal selected from the group consisting of mouse, rat, monkey, pig, dog, rabbit, hamster, guinea pig, horse, and sheep;

The invention claimed is:

1. A method for producing an ectomesenchymal stem cell or a cell population containing the ectomesenchymal stem cell, comprising any one of steps 1) to 9) below:

1) collecting peripheral blood from a subject having a necrotic tissue injury, culturing the peripheral blood to obtain a colony-forming cell, and then selectively recovering a cell that is PDGFRα-positive and Prx1 lineage-negative, wherein the subject is a transgenic 7) collecting peripheral blood from a subject having a necrotic tissue injury, selectively recovering a cell that is PDGFRα-positive, CD34-positive and Sca1-negative from the peripheral blood, and culturing the cell to obtain a colony-forming cell, wherein the subject is selected from the group consisting of mouse, rat, and hamster;

8) collecting peripheral blood from a subject having a necrotic tissue injury, selectively recovering a cell that is PDGFRα-positive, Prx1 lineage-negative, CD34-positive and Sca1-negative from the peripheral blood, and culturing the cell to obtain a colony-forming cell, wherein the subject is a transgenic animal selected from the group consisting of mouse, rat, and hamster; or 9) collecting peripheral blood from a subject having a necrotic tissue injury, selectively recovering a cell that is PDGFRα-positive and CD34-positive from the peripheral blood, and culturing the cell to obtain a colony-forming cell, wherein the subject is selected from the group consisting of human, mouse, rat, monkey, pig, dog, rabbit, hamster, guinea pig, horse, and sheep.

2. A method for producing an ectomesenchymal stem cell, comprising any one of steps 1) to 6) below:
1) collecting a vertebral bone marrow from a subject, culturing the vertebral bone marrow to obtain a colony-forming cell, and then selectively recovering a cell that is PDGFRα-positive, CD34-positive and Sca1-negative, wherein the subject is selected from the group consisting of mouse, rat, and hamster;
2) collecting a vertebral bone marrow from a subject, culturing the vertebral bone marrow to obtain a colony-forming cell, and then selectively recovering a cell that is PDGFRα-positive and CD34-positive, wherein the subject is selected from the group consisting of human, mouse, rat, monkey, pig, dog, rabbit, hamster, guinea pig, horse, and sheep;
3) collecting a vertebral bone marrow from a subject, and selectively recovering a cell that is PDGFRα-positive, CD34-positive and Sca1-negative from the vertebral bone marrow, wherein the subject is selected from the group consisting of mouse, rat, and hamster;
4) collecting a vertebral bone marrow from a subject, and selectively recovering a cell that is PDGFRα-positive and CD34-positive from the vertebral bone marrow, wherein the subject is selected from the group consisting of human, mouse, rat, monkey, pig, dog, rabbit, hamster, guinea pig, horse, and sheep;
5) collecting a vertebral bone marrow from a subject, selectively recovering a cell that is PDGFRα-positive, CD34-positive and Sca1-negative from the vertebral bone marrow, and culturing the cell to obtain a colony-forming cell, wherein the subject is selected from the group consisting of mouse, rat, and hamster; or
6) collecting a vertebral bone marrow from a subject, selectively recovering a cell that is PDGFRα-positive and CD34-positive from the vertebral bone marrow, and culturing the cell to obtain a colony-forming cell, wherein the subject is selected from the group consisting of human, mouse, rat, monkey, pig, dog, rabbit, hamster, guinea pig, horse, and sheep.

3. A method for producing an ectomesenchymal stem cell, comprising:
1) the steps of culturing a cell population derived from a biological tissue of a subject to obtain a colony-forming cell, and then selecting a colony that is PDGFRα-positive and Prx1 lineage-negative,
wherein the biological tissue is peripheral blood or a bone marrow of femur, vertebra, sternum or ilium, the subject is a transgenic animal selected from the group consisting of mouse, rat, monkey, pig, dog, rabbit, hamster, guinea pig, horse and sheep, and the selected colony comprises ectomesenchymal stem cell; or
2) the steps of culturing a cell population derived from a biological tissue of a subject to obtain a colony-forming cell, and then selecting a colony that is PDGFRα-positive, Prx1 lineage-negative, CD34-positive and Sca1-negative,
wherein the biological tissue is peripheral blood or a bone marrow of femur, vertebra, sternum or ilium, the subject is a transgenic animal selected from the group consisting of mouse, rat, and hamster, and the selected colony comprises ectomesenchymal stem cell.

4. A method for producing a cell population containing an ectomesenchymal stem cell, comprising a step of:
1) selectively recovering a cell that is PDGFRα-positive and Prx1 lineage-negative from a cell population derived from a biological tissue of a subject, wherein the biological tissue is peripheral blood or a bone marrow of femur, vertebra, sternum or ilium, the subject is a transgenic animal selected from the group consisting of mouse, rat, monkey, pig, dog, rabbit, hamster, guinea pig, horse and sheep, and the selectively recovered cell comprises ectomesenchymal stem cell; or
2) selectively recovering a cell that is PDGFRα-positive, Prx1 lineage-negative, CD34-positive and Sca1-negative from a cell population derived from a biological tissue of a subject, wherein the biological tissue is peripheral blood or a bone marrow of femur, vertebra, sternum or ilium, the subject is a transgenic animal selected from the group consisting of mouse, rat, and hamster, and the selectively recovered cell comprises ectomesenchymal stem cell.

5. A method for producing an ectomesenchymal stem cell, comprising:
1) the steps of selectively recovering a cell that is PDGFRα-positive and Prx1 lineage-negative from a cell population derived from a biological tissue of a subject, and culturing the selectively recovered cell to obtain a colony-forming cell,
wherein the biological tissue is peripheral blood or a bone marrow of femur, vertebra, sternum or ilium, the subject is a transgenic animal selected from the group consisting of mouse, rat, monkey, pig, dog, rabbit, hamster, guinea pig, horse and sheep, and the colony-forming cell comprises ectomesenchymal stem cell; or
2) the steps of selectively recovering a cell that is PDGFRα-positive, Prx1 lineage-negative, CD34-positive and Sca1-negative from a cell population derived from a biological tissue of a subject, and culturing the selectively recovered cell to obtain a colony-forming cell,
wherein the biological tissue is peripheral blood or a bone marrow of femur, vertebra, sternum or ilium, the subject is a transgenic animal selected from the group consisting of mouse, rat, and hamster, and the colony-forming cell comprises ectomesenchymal stem cell.

6. A method for producing an ectomesenchymal stem cell, comprising:
1) the steps of collecting a vertebral bone marrow from a subject and selectively recovering a cell having any one of characteristics (a) and (b) below from the vertebral bone marrow:
(a) being PDGFRα-positive, CD34-positive, and Sca1-negative;
(b) being PDGFRα-positive, CD34-positive, and Sca1-positive,
wherein the subject is selected from the group consisting of mouse, rat, and hamster; or 2) the steps of collecting a vertebral bone marrow from a subject and selectively recovering a cell that is PDGFRα-positive and CD34-positive from the vertebral bone marrow, wherein the subject is selected from the group consisting of human, mouse, rat, monkey, pig, dog, rabbit, hamster, guinea pig, horse, and sheep.

7. A method for producing an ectomesenchymal stem cell, comprising:
1) the steps of collecting a vertebral bone marrow from a subject and selectively recovering a cell having any one of characteristics (a) and (b) below from the vertebral bone marrow:
   (a) being PDGFRα-positive and Procr-positive;
   (b) being PDGFRα-positive, Procr-positive and CD34-positive,
wherein the subject is selected from the group consisting of human, mouse, rat, monkey, pig, dog, rabbit, hamster, guinea pig, horse, and sheep; or 2) the steps of collecting a vertebral bone marrow from a subject and selectively recovering a cell having any one of characteristics (c) and (d) below from the vertebral bone marrow:
   (c) being PDGFRα-positive, Procr-positive and Sca1-positive;
   (d) being PDGFRα-positive, Procr-positive, CD34-positive and Sca1-positive,
wherein the subject is selected from the group consisting of mouse, rat, and hamster.

8. The method of claim 1, further comprising a step of removing red blood cells prior to the culturing step of step 1), 6), 7), 8) or 9).

9. The method of claim 2, further comprising a step of removing red blood cells prior to the culturing step of step 1), 2), 5) or 6).

* * * * *

SEQUENCE LISTING

```
<160> NUMBER OF SEQ ID NOS: 1

<210> SEQ ID NO 1
<211> LENGTH: 44
<212> TYPE: PRT
<213> ORGANISM: Artificial sequence
<220> FEATURE:
<223> OTHER INFORMATION: An artificially synthesized peptide sequence

<400> SEQUENCE: 1

Met Gly Lys Gly Asp Pro Lys Lys Pro Arg Gly Lys Met Ser Ser Tyr
1               5                   10                  15

Ala Phe Val Gln Thr Cys Arg Glu Glu His Lys Lys Lys His Pro
            20                  25                  30

Asp Ala Ser Val Asn Phe Ser Glu Phe Ser Lys Lys
        35                  40
```